United States Patent
Yonekubo et al.

(10) Patent No.: US 7,750,145 B2
(45) Date of Patent: Jul. 6, 2010

(54) 1-SUBSTITUTED-3-β-D-GLUCOPYRANOSYLATED NITROGENOUS HETERO-CYCLIC COMPOUNDS AND MEDICINES CONTAINING THE SAME

(75) Inventors: Shigeru Yonekubo, Azumino (JP); Nobuhiko Fushimi, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 459 days.

(21) Appl. No.: 11/719,201

(22) PCT Filed: Nov. 17, 2005

(86) PCT No.: PCT/JP2005/021104

§ 371 (c)(1),
(2), (4) Date: May 11, 2007

(87) PCT Pub. No.: WO2006/054629

PCT Pub. Date: May 26, 2006

(65) Prior Publication Data

US 2009/0074738 A1   Mar. 19, 2009

(30) Foreign Application Priority Data

Nov. 18, 2004   (JP) ............... 2004-334165

(51) Int. Cl.
    C07H 7/06      (2006.01)
    A01N 43/04     (2006.01)
    A61K 31/70     (2006.01)
(52) U.S. Cl. ............ 536/29.2; 514/23; 536/1.11; 536/18.7
(58) Field of Classification Search .......... None
     See application file for complete search history.

(56) References Cited

U.S. PATENT DOCUMENTS

| | | | |
|---|---|---|---|
| 6,815,428 B2 | 11/2004 | Ohsumi et al. | |
| 7,094,763 B2 * | 8/2006 | Rybczynski et al. | 514/23 |
| 2003/0087843 A1 | 5/2003 | Hess et al. | |
| 2004/0006025 A1 | 1/2004 | Ohsumi et al. | |
| 2005/0043249 A1 | 2/2005 | Ohsumi et al. | |

FOREIGN PATENT DOCUMENTS

EP   1544208 A1   6/2005
EP   1609785 A1   12/2005
EP   1724278 A1   11/2006
WO   WO 2003/020737 A1   3/2003

OTHER PUBLICATIONS

Byrn et al., Solid-State Chemistry of Drugs, 2d, Chapter 11 Hydrates and Solvates, 233-247, 1999.*
Morissette et al., "High Throughput crystallization: polymorphs, salts, co-crystals, and solvates of pharmaceutical solids", Advanced Drug Delivery Reviews, 56 (2004) 275-300.*
Stella et al., "Prodrugs as therapeutics", Expert Opin Ther Patents, 2004, 14(3) 277-280.*
Adachi et al. "T-1095, a Renal Na+-Glucose Transporter Inhibitor, Improves Hyperglycemia in Streptozotocin-Induced Diabetic Rats", Metabolism, vol. 49 (8), Aug. 2000, pp. 990-995.*

* cited by examiner

*Primary Examiner*—Traviss C McIntosh, III
(74) *Attorney, Agent, or Firm*—Sughrue Mion, PLLC

(57) ABSTRACT

A compound having an SGLT1 and/or SGLT2 inhibitory activity which is usable as an agent for the prevention or treatment of diabetes, postprandial hyperglycemia, impaired glucose tolerance, diabetic complications, obesity, etc. It is a 1-substituted-3-(β-D-glycopyranosyl) nitrogen-containing heterocyclic compound represented by the general formula (I), a prodrug thereof, or a pharmaceutically acceptable salt thereof, or a hydrate or a solvate thereof; an SGLT inhibitor containing the same; a pharmaceutical composition containing the same and a combination pharmacy of them. In the formula, A represents an alkylene group or alkenylene group; B represents a single bond, —O—, —S— or —NH—; C represents an optionally substituted aryl or heteroaryl group; Q independently represents a carbon atom which a hydrogen atom or a substituent binds to, or a nitrogen atom.

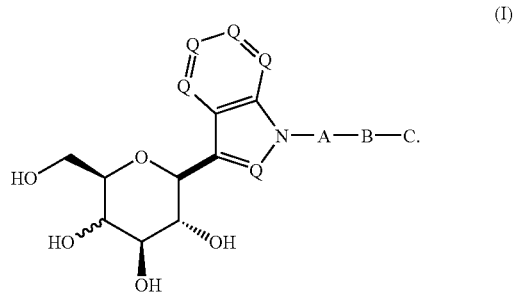

10 Claims, No Drawings

1-SUBSTITUTED-3-β-D-GLUCOPYRANOSYLATED NITROGENOUS HETERO-CYCLIC COMPOUNDS AND MEDICINES CONTAINING THE SAME

TECHNICAL FIELD

The present invention relates to a 1-substituted-3-(β-D-glycopyranosyl) nitrogen-containing heterocyclic compound. More particularly, the present invention relates to a 1-substituted-3-(β-D-glycopyranosyl) nitrogen-containing heterocyclic compound which can be used as an agent for the prevention or treatment of a disease associated with hyperglycemia such as diabetes, impaired glucose tolerance, diabetic complications or obesity, a prodrug thereof, a pharmaceutically acceptable salt thereof, a hydrate or a solvate thereof, a pharmaceutical composition comprising the same, and a combination of the same and another pharmaceutical composition.

BACKGROUND ART

It is known that a sodium-dependent glucose transporter, herein after referred to as "SGLT", which is a co-transporter of monosaccharide and sodium has some subtypes. Namely, a sodium-dependent glucose transporter 1, herein after referred to as "SGLT1", exists mainly in the small intestine and the S3 segment of the kidney's proximal tubule, and a sodium-dependent glucose transporter 2, herein after referred to as "SGLT2", exists mainly in the S1 segment of the kidney's proximal tubule.

Among them, SGLT1 which exists in the small intestine participates in glucose and galactose absorption from the digestive tract (Non-patent references 1 and 2). In diabetic patients, carbohydrate digestion and absorption increase. Actually, it is confirmed that SGLT1 and its mRNA highly increase in the small intestine (see Non-patent reference 3). Therefore, inhibiting SGLT1 can control increase of blood sugar level by suppression of glucose and galactose absorption in the small intestine (see Patent reference 1).

On the other hand, SGLT2 participates in reabsorption of glucose filtrated through the glomerulus (see Non-patent reference 4). Therefore, inhibiting SGLT2 can normalize blood sugar level by suppression of glucose reabsorption (see Patent reference 5).

As compounds inhibiting SGLT1, pyrazole derivatives (see Patent references 1 and 2), benzylphenol derivatives (see Patent reference 3) and the like are known. And as compounds inhibiting SGLT2, glucopyranosyloxypyrazole derivatives (see Patent reference 4), glucopyranosyloxybenzylbenzene derivatives (see Patent reference 5) and the like are known. Both of the above-mentioned SGLT1 inhibitors and SGLT2 inhibitors are O-glucoside derivatives wherein a glucopyranosyl group binds to an aryl group or a heteroaryl group through an oxygen atom.

Recently, it was reported that regarding fluoroglycoside heterocyclic derivatives (see Patent reference 6) and C-glucoside derivatives whose glucopyranosyl group binds to a carbon atom in a ring of a nitrogen-containing heterocyclic compound (see Patent reference 7), they show an SGLT inhibitory activity. However, in these reports, nothing was described or suggested concerning a compound which has a substituent such as an aryl group on a nitrogen atom at 1-position of a fused cyclic nitrogen-containing heterocyclic compound and a glycopyranosyl group such as a glycopuranosyl group, a galactopyranosyl group or the like at 3-position of the same.

[Non-patent reference 1] Yoshikatsu Kanai, Kidney and Dialysis, 1998.12, Vol. 45, extra edition, pp. 232-237;

[Non-patent reference 2] E. Turk and 4 persons, Nature, 1991.3, Vol. 350, pp. 354-356;

[Non-patent reference 3] J. Dyer and 4 persons, American Journal of Physiology, 2002.2, Vol. 282, No. 2, pp. G241-G248;

[Non-patent reference 4] Yoshikatsu Kanai and 4 persons, J. Clin. Invest., 1994.1, Vol. 93, pp. 397-404;

[Patent reference 1] International Publication No. WO04/014932 pamphlet;

[Patent reference 2] International Publication No. WO04/018491 pamphlet;

[Patent reference 3] Japanese patent publication No. JP2004-196788;

[Patent reference 4] International publication No. WO01/16147 pamphlet;

[Patent reference 5] International publication No. WO01/68660 pamphlet;

[Patent reference 6] International publication No. WO04/052903 pamphlet;

[Patent reference 7] International publication No. WO04/080990 pamphlet.

DISCLOSURE OF THE INVENTION

Objects to be Solved by the Invention

The present invention aims to provide a compound which has an SGLT1 and/or SGLT2 inhibitory activity.

The present inventors have studied earnestly on compounds having an inhibitory activity against SGLT1 and/or SGLT2. As a result, it was found that certain 1-substituted-3-(β-D-glycopyranosyl) nitrogen-containing heterocyclic compound represented by the following general formula (I) has an excellent inhibitory activity against SGLT1 and/or SGLT2, thereby forming the basis of the present invention.

That is, the gist of the present invention resides in a 1-substituted-3-(β-D-glycopyranosyl) nitrogen-containing heterocyclic compound represented by the following general formula (I) or a prodrug thereof, a pharmaceutically acceptable salt thereof, or a hydrate or a solvate thereof; an SGLT inhibitor comprising the same; a pharmaceutical composition comprising the same; and a combination of the same and another pharmaceutical composition.

[Chem. 1]

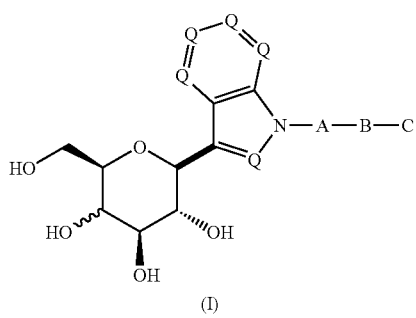

(I)

wherein A represents an alkylene group or an alkenylene group; B represents a single bond, —O—, —S— or —NH—;

C represents an optionally substituted aryl or a heteroaryl group; Q independently represents a carbon atom which a hydrogen atom or a substituent binds to, or a nitrogen atom.

EFFECTS OF THE INVENTION

Since a 1-substituted-3-(β-D-glycopyranosyl) nitrogen-containing heterocyclic compound (I) of the present invention or a prodrug thereof, a pharmaceutically acceptable salt thereof, or a hydrate or a solvate thereof has an excellent inhibitory activity against SGLT1 and/or SGLT2, it can control the increase of blood sugar level and normalize blood sugar level.

BEST MODE TO PUT THE INVENTION TO PRACTICE

Meanings of terms used in this description are as follows.

The term "nitrogen-containing heterocyclic compound" means a heterocyclic compound having any nitrogen atoms as a hetero atom.

The term "halogen atom" means a fluorine atom, a chlorine atom, a bromine atom or an iodine atom.

The term "alkyl" means optionally branched lower alkyl having 1 to 6 carbon atoms.

The term "alkenyl" means optionally branched lower alkenyl having 2 to 6 carbon atoms.

The term "alkynyl" means optionally branched lower alkynyl having 2 to 6 carbon atoms.

The term "alkylene" means optionally branched lower alkylene having 1 to 6 carbon atoms.

The term "alkenylene" means optionally branched lower alkenylene having 2 to 6 carbon atoms.

The term "alkoxy" means optionally branched lower alkoxy having 1 to 6 carbon atoms.

The term "(di)alkylamino" means monoalkylamino or dialkylamino whose two alkyls may be different.

The term "aryl" means phenyl or naphthyl.

The term "heteroaryl" means monocyclic or fused cyclic heteroaryl having 1 or more hetero atoms selected from a group consisting of an oxygen atom, a nitrogen atom and a sulfur atom.

The term "(hetero)aryl" means aryl or heteroaryl.

The term "cycloalkyl" means cycloalkyl having 3 to 7 carbon atoms.

The term "heterocycloalkyl" means 3 to 7-membered heterocycloalkyl having 1 or more hetero atoms selected from a group consisting of an oxygen atom, a nitrogen atom and a sulfur atom.

The term "(hetero)cycloalkyl" means cycloalkyl or heterocycloalkyl.

The term "alicyclic amine" means a heterocycloalkyl having a nitrogen atom at the binding position.

The term "acyl" means optionally branched aliphatic carboxyl acyl having 2 to 7 carbon atoms, (hetero)-cycloalkyl-carboxyl acyl or (hetero)arylcarboxyl acyl.

In the general formula (I), as the glycopyranosyl group, a glucopyranosyl group or a galactopyranosyl group, especially a glucopyranosyl group, is preferable.

As A, an alkylene group, especially a methylene group, is preferable.

As B, a single bond is preferable.

As the heteroaryl group in C, for example, a 5-membered monocyclic heteroaryl group such as a furyl group, a thienyl group, a pyrrolyl group, an oxazolyl group, a thiazolyl group, an imidazolyl group and the like, and a 6-membered monocyclic heteroaryl group such as a pyridyl group, a pyrimidinyl group, a pyridazinyl group, a pyrazinyl group and the like; and a fused cyclic heteroaryl group such as an indolyl group, an isoindolyl group, a quinolyl group, an isoquinolyl group, a benzofuranyl group, a benzothienyl group, a thieno[2,3-b]thienyl group, a thieno[3,2-b]thienyl group and the like can be illustrated.

As C, an aryl group, especially a phenyl group is preferable.

As a substituent which the (hetero)aryl group may have, for example, a halogen atom, a hydroxy group and a cyano group; an alkyl group, an alkoxyalkyl group, an alkenyl group, an alkynyl group, an alkoxy group, an acyloxy group, an alkylthio group, an alkylsulfinyl group and an alkylsulfonyl group, each of which may have any substituent α (to be described below, the same herein after); a (hetero)aryl group and a (hetero)cycloalkyl group, each of which may have any substituent α and optionally bind to a (hetero)aryl group via an alkylene group, —O—, —NH— or —S—; a —U—V—W—N($R^4$)—Y—Z group, a —U—V—COO—Y—$R^B$ group and the like can be illustrated. Further, as a (hetero)aryl group has substituents, they may be different. Among them, as a substituent which the (hetero)aryl group may have, a halogen atom, a hydroxy group and a cyano group; an alkyl group, an alkoxy group and an alkylthio group, each of which may have any substituent α; a —U—V—W—N($R^4$)—Y—Z group or a —U—V—COO—Y—$R^B$ group is preferable.

In the —U—V—W—N($R^4$)—Y—Z group or —U—V—COO—Y—$R^B$ group, U means a single bond, —O— or —S—. As U, a single bond or —O— is preferable.

V means a single bond, or an alkylene or alkenylene group, each of which may have a hydroxy group, an alkylene group which may have a hydroxy group is preferable.

W means a single bond, —CO—, —$SO_2$— or —C(=NH)—. As W, a single bond or —CO— is preferable.

$R^A$ means a hydrogen atom, or an alkyl group, a (hetero)aryl group or a (hetero) cycloalkyl group, each of which may have any substituent α. As $R^A$, a hydrogen atom or an alkyl group which may have any substituent α is preferable.

Y means a single bond or an alkylene group which may have an oxo group.

Z means a hydrogen atom; a formyl group; or an alkyl group, a (hetero)aryl group or a (hetero) cycloalkyl group, each of which may have any substituent α; an acyl group which may have any substituent α; an alkoxy group or an arylalkoxycarbonyl group, each of which may have any substituent α; —CON($R^1$)($R^2$), —CSN($R^1$)($R^2$), —$SO_2$N($R^1$)($R^2$) or —C(=N$R^1$)N($R^2$)($R^3$); one to three amino acid residues, wherein the terminal carboxyl group is an alkoxycarbonyl group optionally having a hydroxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an amino group or a (di)alkylamino group; or a carboxamide group; or an aliphatic, (hetero)cycloalkyl or (hetero)aryl carboxylic acid residue having an alicyclic amine, each of which may have an alkyl group, a (hetero) cycloalkyl group, an alkoxycarbonyl group or an acyl group, each of which may have a hydroxy group an amino group or a (di) alkylamino group.

$R^1$, $R^2$ and $R^3$ independently mean a hydrogen atom, a nitro group, a cyano group, a sulfamoyl group, an acyl group, an alkoxycarbonyl group, an aryl group, an alkylsulfonyl group or an alkyl group optionally having any substituent α. A hydrogen atom or an alkyl group optionally having any substituent α is independently preferable.

$R^A$ and a part of a group forming Z, each of which binds to a nitrogen atom, may bind together to form an alicyclic amine optionally having any substituent α.

$R^B$ means a hydrogen atom; an alkoxyalkyl group having a carboxy group or an alkoxycarbonyl group; an alkyl group, a (hetero)aryl group or a (hetero)cycloalkyl group, each of which may have any substituent α; one to three amino acid residues, wherein the terminal carboxyl group may be an alkoxycarbonyl group optionally having a hydroxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an amino group or a (di)alkylamino group; or a carboxamide group; or an aliphatic, (hetero)cycloalkyl or (hetero)aryl carboxylic acid residue having an alicyclic amine, which may have an alkyl group, a (hetero) cycloalkyl group, an alkoxycarbonyl group or an acyl group, each of which may have a hydroxy group an amino group or a (di)alkylamino group.

As the alicyclic amine, for example, pyrrolidine, piperidine, piperazine, morpholine and the like can be illustrated.

As the amino acid, for example, a natural amino acid and a synthetic amino acid may be employed. As the synthetic amino acid, a homoamino acid such as 2-methylalanine, a noramino acid such as norvaline and the like can be illustrated.

When U is —O— or —S—, V and W are not a single bond at the same time.

In case that any of Q is a carbon atom, as the substituent optionally bound thereto, for example, a halogen atom, a hydroxy group, an amino group, a carboxyl group, a cyano group, a (di)alkylamino group or a cycloalkyloxy group; and an alkyl group, an alkoxy group, a cycloalkyl group and an alkoxycarbonyl group, each of which may have any substituent α are illustrated. Among them, a halogen atom or an alkyl group, especially a fluorine atom, a chlorine atom or a methyl group, is preferable.

The number of nitrogen atoms in Q is preferably 0 to 2 in total, and more preferably 0, that is, all of Q are more preferably a carbon atom which a hydrogen atom or a substituent binds to.

The substituent α means a group selected from a group consisting of a halogen atom, a hydroxy group, an acyloxy group, an alkoxycarbonyloxy group, an amino group, a cyano group, a carboxyl group, a carbamoyl group, an alkoxy group, a (di)alkylamino group, an alkoxycarbonyl group, a hydroxyalkoxycarbonyl group, a (hetero)aryl group and a (hetero) cycloalkyl group in case that any groups have substituents, these substituents may be the same or different.

As a 1-substituted-3-(β-D-glycopyranosyl) nitrogen-containing heterocyclic compound (I) of the present invention, a 1-substituted-3-(β-D-glucopyranosyl)indole compound represented by the following general formula (II)

[Chem. 2]

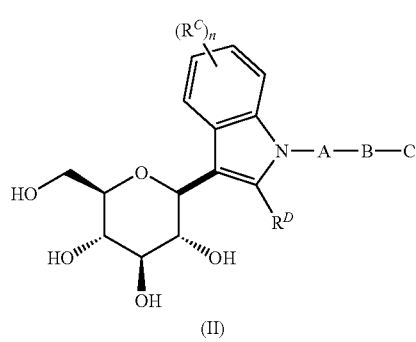

(II)

wherein A to C have the same meanings as defined above, $R^C$ independently represents a halogen atom or an alkyl group, $R^D$ represents a hydrogen atom, a halogen atom or an alkyl group, and n represents an integral number from 0 to 4 is preferable.

In a 1-substituted-3-(β-D-glucopyranosyl)indole compound represented by the general formula (II), as A, a methylene group is preferable, and as B, a single bond is preferable. And as C, a phenyl group substituted by a group selected from a group consisting of a methyl group, an ethyl group, a methoxy group, an ethoxy group, an isopropoxy group, a difluoromethoxy group, a hydroxy group, a 2-hydroxyethyl and a 3-hydroxypropyl group at p-position, and optionally substituted by a fluorine atom at o-position or m-position is preferable. As a halogen atom of $R^C$, a fluorine atom or a chlorine atom is preferable, as an alkyl group, a methyl group is preferable. As $R^D$, a hydrogen atom is preferable.

An example of the processes for preparing a 1-substituted-3-(β-D-glycopyranosyl) nitrogen-containing heterocyclic compound (I) of the present invention is shown below.

[Chem. 3]

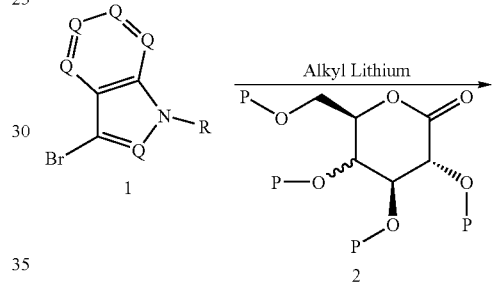

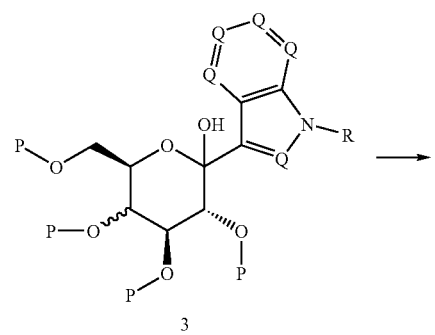

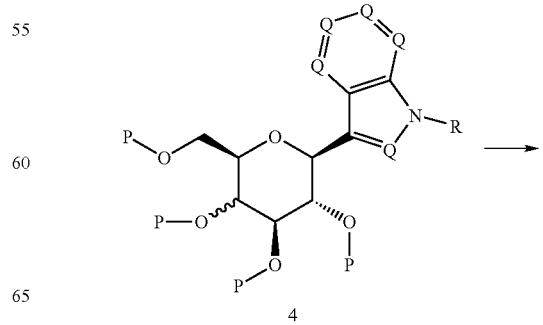

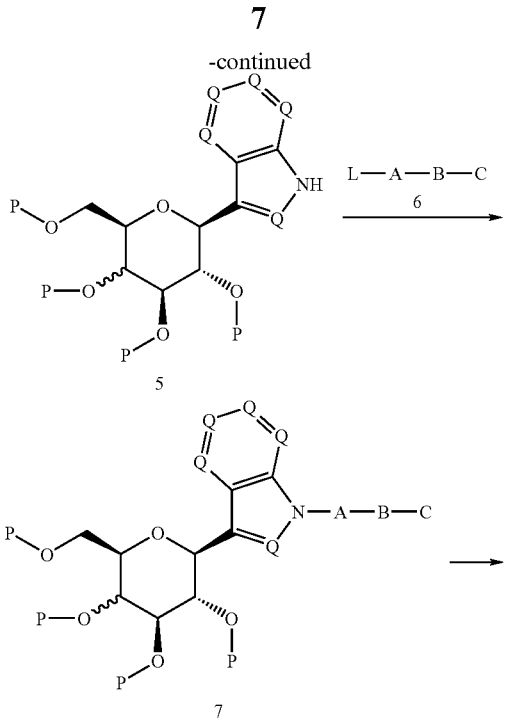

wherein Q and A to C have the same meanings as defined above, P represents a hydroxy-protective group, R represents a NH-protective group and L represents a leaving group.

After treating a 3-bromo nitrogen-containing heterocyclic compound wherein a NH group of indole at 1-position is protected (1) with an alkyllithium, a hemiacetal (3) is prepared by allowing the mixture to react with a hydroxy-protected D-glycono-1,5-lactone (2). A 1-protected-3-(β-D-glycopyranosyl) nitrogen-containing heterocyclic compound (4) is prepared by reductive removal of the obtained glycoside-hydroxy group. And after a 3-(β-D-glycopyranosyl) nitrogen-containing heterocyclic compound (5) is prepared by removing the protective group at 1-position of the obtained nitrogen-containing heterocyclic compound (4), a 1-substituted-3-(β-D-glycopyranosyl) nitrogen-containing heterocyclic compound in which hydroxy groups are protected (7) is prepared by allowing the obtained (5) to react with an alkylating agent (6). A 1-substituted-3-(β-D-glycopyranosyl) nitrogen-containing heterocyclic compound (I) can be prepared by removing the hydroxy-protective groups at the end.

A 3-bromo nitrogen-containing heterocyclic compound (1) can be prepared by allowing a nitrogen-containing heterocyclic compound wherein a NH group of indole at 1-position is protected to react with a brominating reagent such as bromine, N-bromosuccinimide or the like. As the protective group of NH group, for example, a sulfonyl group such as a tosyl group or the like can be illustrated. And nitrogen-containing heterocyclic compound used in the reaction can be commercially available or can be easily prepared by known processes.

The D-glycono-1,5-lactone wherein a hydroxy group is protected (2) can be also commercially available or can be easily prepared by known processes. As the hydroxy-protective group, any protective group commonly used in the field of sugar chemistry may be employed. For example, an optionally substituted benzyl group such as a benzyl group, a p-methoxybenzyl group or the like can be illustrated.

The reaction of the 3-bromo nitrogen-containing heterocyclic compound (1) and an alkyllithium, and the next reaction with a D-glycono-1,5-lactone wherein a hydroxy group is protected (2) may be conducted by mixing in a suitable solvent at from −78° C. to a boiling point of the solvent for from 10 minutes to 1 day.

As the alkyllithium, for example, n-butyllithium or the like can be illustrated. As the reaction solvent, for example, an ether such as tetra hydrofuran, diethylether and the like; a saturated carbohydrate such as n-hexane and the like; a mixed solvent thereof and the like can be illustrated.

By mixing a hemiacetal (3) and a reducing agent in a suitable solvent in the presence of an acid at from −20° C. to a boiling point of the solvent for from 1 hour to 3 days, a glycoside-hydroxy group can be removed reductively.

As the reducing agent, for example, a trialkylsilane such as triethylsilane, triisopropylsilane and the like can be illustrated. As the acid, for example, a Lewis acid such as boron trifluoride diethyl ether complex or the like, and an organic acid such as trifluoroacetic acid or the like can be illustrated. As the reaction solvent, for example, an ether such as tetra hydrofuran and the like; a halogenated hydrocarbon such as methylene chloride and the like; an aprotic polar solvent such as acetonitrile; a mixed solvent thereof and the like can be illustrated.

In case that a protective group of a NH group of indole is a tosyl group, the tosyl group can be removed by mixing the nitrogen-containing heterocyclic compound (4) in a suitable solvent in the presence of a base at from room temperature to a boiling point of the solvent for from 1 hour to 3 days.

As the reaction solvent, for example, water; an alcohol such as methanol, ethanol and the like; an ether such as tetra hydrofuran, 1,4-dioxane and the like; a mixed solvent thereof and the like can be illustrated. And as the base, for example, an alkali metal hydroxide such as sodium hydroxide, potassium hydroxide and the like can be illustrated.

The 3-(β-D-glycopyranosyl) nitrogen-containing heterocyclic compound (5) can be alkylated by mixing with an alkylating agent (6) in a suitable solvent in the presence of a base at from −78° C. to a boiling point of the solvent for from 1 hour to 1 day.

An alkylating agent can be commercially available or can be easily prepared by known processes. As a leaving group of an alkylating agent, for example, a chlorine atom, a bromine atom, an iodine atom, a mesyloxy group, a tosyloxy group and the like can be illustrated.

As the reaction solvent, for example, an ether such as tetra hydrofuran and the like; an aprotic polar solvent such as N,N-dimethylformamide and the like; a mixed solvent thereof and the like can be illustrated. And as the base, for example, an alkali metal hydride such as sodium hydride and the like, an alkali metal hydroxide such as sodium hydroxide and the like; alkali metal alkoxides such as potassium t-butoxide and the like; and an alkyllithium such as n-butyllithium and the like can be illustrated.

An obtained 1-substituted-3-(β-D-glycopyranosyl) nitrogen-containing heterocyclic compound in which hydroxy groups are protected (7) can be deprotected by a common method in the sugar chemistry. For example, when the protective group is a benzyl group optionally having any substituent, it can be removed, for example, by hydrogenolysis which is performed in an adequate solvent by adding a noble metal catalyst such as palladium-carbon powder and the like and mixing under a hydrogen atmosphere at from atmospheric pressure to medium pressure at from 0° C. to a boiling point of the solvent for from 30 minutes to 1 day.

As the reaction solvent, for example, an alcohol such as methanol, ethanol and the like; an ether such as tetra hydrofuran and the like; a carboxylic ester such as ethyl acetate and the like; a carboxylic acid such as acetic acid and the like; a mixed solvent thereof and the like can be illustrated.

The benzyl group optionally having any substituent can be also removed by adding an acid such as boron trichloride, boron tribromide, boron trifluoride diethyl ether complex or the like, and optionally adding a thiol compound such as ethanethiol or the like, and mixing them in an adequate solvent at from 0° C. to a boiling point of the solvent for from 30 minutes to 1 day.

As the reaction solvent, for example, a halogenated hydrocarbon such as methylene chloride, 1,2-dichloroethane and the like; acetonitrile; a mixed solvent thereof and the like are illustrated.

After the above-mentioned deprotection reaction, a 1-substituted-3-(β-D-glycopyranosyl) nitrogen-containing heterocyclic compound (I) can be obtained by treating the reaction mixture in the usual way and optionally by a conventional purification method.

The 1-substituted-3-(β-D-glycopyranosyl) nitrogen-containing heterocyclic compound (I) can be also prepared according to the above preparation method by subjecting a nitrogen-containing heterocyclic compound which has an A-B-C group (8) successively to bromination, lithiation, reaction with a D-glycono-1,5-lactone wherein a hydroxy group is protected (2), reductive removal of the glycoside-hydroxy group and at the last removing the hydroxy-protective group.

In addition, in case that a nitrogen-containing heterocyclic ring of a nitrogen-containing heterocyclic compound (8) is an indole ring, a 1-substituted-3-(β-D-glycopyranosyl) nitrogen-containing heterocyclic compound (I) can be also prepared by allowing to react with 2,3,4,6-tetra-O-benzyl-α-D-glucopyranosyl trichloroacetimidate (Richard R. Schmit, et al. Liebigs Ann. Chem., 825-831, 1987) in the presence of zinc chloride, and by removing the hydroxy-protective group.

[Chem. 4]

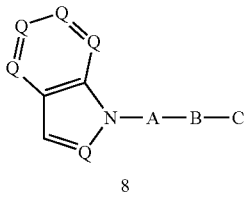

8 wherein Q and A to C have the same meanings as defined above.

In these preparation methods, a nitrogen-containing heterocyclic compound wherein Q is independently a carbon atom which a hydrogen atom or a substituent binds to, that is, an indole compound, may be prepared by known methods such as Fisher's indole synthesis or appropriate chemical modification to a commercially available indole compound. In addition, as a nitrogen-containing heterocyclic compound wherein any of Q is a nitrogen atom, a commercially available compound such as 4-azaindole (APIN Co.), 5-azaindole (APIN Co.), 6-azaindole (ASTATECH Co.) or 7-azaindole (ALDRICH Co.), or a compound prepared by known methods, for example, 4,6-diazaindole (Ektova, L. V. et. al., Khikiko-Farmatsevticheskii Zhurnal, 22(7), 860-3, 1988) or their combination as the occasion can be used.

Further, a substituent which a (hetero) aryl group may have can be introduced to an easily available (hetero)aryl compound by optionally combining conventional halogenation, amination, nitration, sulfonation, diazotization, thiolation, esterification, amidation, oxidation, reduction, dehydrative condensation, hydrolization, coupling and the like (for example, see WO04/014932 and WO04/018491 pamphlets). In addition, when a compound used or generated in the above-mentioned preparation methods has a functional group which changes under the reaction condition or inhibits the reaction progression, the group may be protected by an appropriate protective group used by a skilled person in the art and the protective group may be removed in an appropriate step.

A prodrug of a 1-substituted-3-(β-D-glycopyranosyl) nitrogen-containing heterocyclic compound represented by the general formula (I) of the present invention can be prepared by conventional method using the corresponding reagent to produce a prodrug such as a halide compound or the like, optionally by introducing a group forming a prodrug to one or more groups selected from a group consisting of a carboxyl group, a hydroxy group or an amino group in a compound represented by the above formula (I) by conventional method. As the group forming a prodrug, for example, an alkyl group, a (hetero)arylalkyl group, an acyl group, an alkoxyacyl group, an (alkoxycarbonyl)acyl group, an alkoxycarbonyl group, an aryl(alkoxycarbonyl) group, an alkoxy (alkoxycarbonyl) group, an (acyloxy)methyl group, a 1-(acyloxy)ethyl group, an (alkoxycarbonyloxy)methyl group, a 1-(alkoxycarbonyloxy)ethyl group, a [(cycloalkyloxy)-carbonyloxy]methyl group, a 1-[(cycloalkyloxy)carbonyl-oxy] ethyl group or the like can be illustrated.

As a prodrug, a prodrug wherein a group selected from a group consisting of an acyl group, an alkoxy(acyl) group, an alkoxycarbonyl(acyl) group, an alkoxycarbonyl group, an aryl(alkoxycarbonyl) group, an alkoxy(alkoxycarbonyl) group, an (acyloxy)methyl group, a 1-(acyloxy)ethyl group, an (alkoxycarbonyloxy)methyl group, a 1-(alkoxycarbonyloxy)ethyl group, a [(cycloalkyloxy)carbonyloxy]methyl group and a 1-[(cycloalkyloxy)carbonyloxy]ethyl group is introduced into any one or more hydroxy groups selected from a hydroxy group of a glycopyranosyl group and/or any hydroxy group which exists on a (hetero)aryl group of C as a substituent is preferable.

Furthermore, a prodrug of the 1-substituted-3-(β-D-glycopyranosyl) nitrogen-containing heterocyclic compound represented by the general formula (I) of the present invention includes that to be converted into the compound (I) of the present invention under physiologic conditions described in Iyakuhin No Kaihatsu (Development of Drugs), Vol. 7, "Molecular Design", pp. 163 to 198, by Hirokawa-shoten.

A 1-substituted-3-(β-D-glycopyranosyl) nitrogen-containing heterocyclic compound represented by the general formula (I) or a prodrug thereof can be converted into a pharmaceutically acceptable salt by conventional method. As the salt, for example, a salt with an inorganic acid such as hydrochloric acid, nitric acid and the like; a salt with an organic acid such as acetic acid, methanesulfonic acid and the like and a sodium salt and a potassium salt; and a salt with an organic base such as N,N'-dibenzylethylenediamine, 2-aminoethanol and the like can be illustrated.

Occasionally a 1-substituted-3-(β-D-glycopyranosyl) nitrogen-containing heterocyclic compound represented by the general formula (I) or a prodrug thereof is obtained as a hydrate or a solvate thereof after purification or salt formation process. For the pharmaceutical composition of the present invention, any of the 1-substituted-3-(β-D-glycopyranosyl) nitrogen-containing heterocyclic compound, any of a prodrug thereof, or a pharmaceutically acceptable salt thereof, or a hydrate or a solvate thereof can be employed.

Furthermore, a 1-substituted-3-(β-D-glycopyranosyl) nitrogen-containing heterocyclic compound represented by the general formula (I) or a prodrug thereof sometimes has tautomers, geometrical isomers and/or optical isomers. For the pharmaceutical composition of the present invention, any of the isomers and a mixture thereof can be employed.

A Pharmaceutical composition of the present invention may be prepared by mixing a 1-substituted-3-(β-D-glycopyranosyl) nitrogen-containing heterocyclic compound (I) or a prodrug thereof or a pharmaceutically acceptable salt thereof, or a hydrate or a solvate thereof and a conventional pharmaceutical carrier.

The pharmaceutical carrier may be used optionally in combination according to a dosage form as described below. As the pharmaceutical carrier, additives such as lactose or the like; lubricants such as magnesium stearate or the like; disintegrators such as carboxymethyl cellulose or the like; binders such as hydroxypropylmethylcellulose or the like; surfactants such as macrogol or the like; foamings such as sodium bicarbonate or the like; dissolving aids such as cyclodextrin or the like; acidities such as citric acid or the like; stabilizers such as sodium edeate or the like; pH controls such as phosphoric acid salt or the like can be illustrated.

As the dosage form of the pharmaceutical composition of the present invention, oral administrations such as powders, granules, fine granules, dry syrups, tablets, capsules and the like; parenteral administrations such as injections, poultices, suppositories and the like are illustrated.

As the 1-substituted-3-(β-D-glycopyranosyl) nitrogen-containing heterocyclic compound represented by the general formula (I) shows a potent inhibitory activity against human SGLT1 and/or SGLT2 in human SGLT1 and SGLT2 inhibitory activity confirmatory tests, it can inhibit the postprandial increase of the blood sugar lever increase by inhibiting the absorption of glucose or galactose, and/or normalize the blood glucose level by inhibiting the reabsorption of glucose. Accordingly, the pharmaceutical composition of the present invention can be used as an inhibitor of postprandial hyperglycemia, or as an agent for the prevention or treatment of a disease selected from a group consisting of diabetes, impaired glucose tolerance, diabetic complications (for example, retinopathy, neuropathy, nephropathy, ulcer, macroangiopathy), obesity, hyper-insulinemia, galactosemia, hyperlipidemia, hyper-cholesterolemia, hypertriglyceridemia, lipid metabolism disorder, atherosclerosis, hypertension, metabolic syndrome, congestive heart failure, edema, hyperuricemia and gout, or the inhibition of impaired glucose tolerance advancing into diabetes.

For manufacturing the above agent for the prevention or treatment, the dosage of the compound represented by the general formula (I) of the present invention, or a pharmaceutically acceptable salt thereof, or a hydrate or a solvate thereof is appropriately within the range of from 0.1 to 1,000 mg per day per adult human in case of oral administration and approximately within the range of from 0.01 to 100 mg per day per adult human in the case of parenteral administration in formulation.

Furthermore, a drug of the present invention can be used in combination with other drug(s). Examples of such other drugs include an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroiddehydrogenaze inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, an antidiarrhoics, a cathartics, a hydroxymethylglutaryl coenzyme A reductase inhibitor, a fibrate, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a squalene epoxidase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent, and a urinary alkalinizer.

As an insulin sensitivity enhancer, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, N,N-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for the prevention or treatment of diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for the prevention or treatment of diabetes, impaired glucose tolerance or hyperinsulinemia because of improving the disturbance of insulin signal transduction in peripheral tissues and enhancing glucose uptake into the tissues from the blood, leading to lowering of blood glucose level.

As an amylase inhibitor, for example, RSH-2083 and the like are illustrated.

As an α-glucosidase inhibitor, for example, α-glucosidase inhibitors such as acarbose, voglibose, miglitol, CKD-711, emiglitate, MDL-25, 637, camiglibose and MDL-73,945, AZM-127 and the like are illustrated.

Amylase inhibitors and α-glucosidase inhibitors are used preferably for the prevention or treatment of diabetes, impaired glucose tolerance, diabetic complications, obesity or hyperinsulinemia, and more preferably for the prevention or treatment of impaired glucose tolerance because of inhibiting the gastrointestinal enzymatic digestion of carbohydrates contained in foods, and inhibiting or delaying the absorption of glucose or the like into the body.

As a biguanide, for example, phenformin, buformin hydrochloride, metformin hydrochloride and the like are illustrated. Biguanides are used preferably for the prevention or treatment of diabetes, impaired glucose tolerance, diabetic complications or hyperinsulinemia, and more preferably for the prevention or treatment of diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As an insulin secretion enhancer, for example, tolbutamide, chlorpropamide, tolazamide, acetohexamide, glyclopyamide, glyburide (glibenclamide), gliclazide, 1-butyl-3-metanilyl-urea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. In addition, the insulin secretion enhancers include glucokinase activators such as RO-28-1675. Insulin secretion enhancers are used preferably for the prevention or treatment of diabetes, impaired glucose tolerance or diabetic complications, and more preferably for the prevention or treatment of diabetes or impaired glucose tolerance because of lowering blood glucose level by acting on pancreatic β-cells and enhancing the insulin secretion.

As insulin or an insulin analogue, for example, human insulin, animal-derived insulin, human or animal-derived insulin analogues and the like are illustrated. These preparations are used preferably for the prevention or treatment of diabetes, impaired glucose tolerance or diabetic complications, and more preferably for the prevention or treatment of diabetes or impaired glucose tolerance.

As a glucagon receptor antagonist, for example, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, for example, NVP-DPP728A, TSL-225, P-32/98, MK-0431 and the like are illustrated; as protein tyrosine phosphatase 1B inhibitors, for example, PTP-112, OC-86839, PNU-177496 and the like are illustrated; as glycogen phosphorylase inhibitors, for example, N,N-4201, inglifolib and the like are illustrated; as fructose-bisphosphatase inhibitors, for example, CS-917 and the like are illustrated; as pyruvate dehydrogenase inhibitors, for example, AZD-7545 and the like are illustrated; as hepatic gluconeogenesis inhibitors, for example, FR-225659 and the like are illustrated; as an 11β-hydroxysteroid-dehydrogenaze inhibitor, for example, BVT-3498, HM-2002 and the like are illustrated; as glucagon-like peptide-1 analogues, for example, exendin-4, CJC-1131 and the like are illustrated; as glucagon-like peptide 1 agonists; AZM-134, LY-315902 and the like are illustrated; and as amylin, amylin analogues or amylin agonists, for example, pramlintide acetate and the like are illustrated. These drugs, glucose-6-phosphatase inhibitors, D-chiroinositol, glycogen synthase kinase-3 inhibitors and glucagon-like peptide-1 are used preferably for the prevention or treatment of diabetes, impaired glucose tolerance, diabetic complications or hyperinsulinemia, and more preferably for the prevention or treatment of diabetes or impaired glucose tolerance.

As an aldose reductase inhibitor, for example, ascorbyl gamolenate, tolrestat, epalrestat, ADN-138, BAL-AR18, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are used preferably for the prevention or treatment of diabetic complications because of inhibiting aldose reductase and lowering excessive intracellular accumulation of sorbitol in accelerated polyol pathway which are in continuous hyperglycemic condition in the tissues in diabetic complications.

As an advanced glycation endproduct formation inhibitors, for example, pyridoxamine, OPB-9195, ALT-946, ALT-711, pimagedine hydrochloride and the like are illustrated. Advanced glycation endproducts formation inhibitors are used preferably for the prevention or treatment of diabetic complications because of inhibiting formation of advanced glycation endproducts which are accelerated in continuous hyperglycemic condition in diabetes and declining of cellular damage.

As a protein kinase C inhibitor, for example, LY-333531, midostaurin and the like are illustrated. Protein kinase C inhibitors are used preferably for the prevention or treatment of diabetic complications because of inhibiting of protein kinase C activity which is accelerated in continuous hyperglycemic condition in diabetes.

As a γ-aminobutyric acid receptor antagonist, for example, topiramate and the like are illustrated; as sodium channel antagonists, for example, mexiletine hydrochloride, oxcarbazepine and the like are illustrated; as transcript factor NF-κB inhibitors, for example, dexlipotam and the like are illustrated; as lipid peroxidase inhibitors, for example, tirilazad mesylate and the like are illustrated; as N-acetylated-α-linked-acid-dipeptidase inhibitors, for example, GPI-5693 and the like are illustrated; and as carnitine derivatives, for example, carnitine, levacecamine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are used preferably for the prevention or treatment of diabetic complications.

As an antidiarrhoics or cathartic, for example, polycarbophil calcium, albumin tannate, bismuth subnitrate and the like are illustrated. These drugs are used preferably for the prevention or treatment of diarrhea, constipation or the like accompanying diabetes or the like.

As a hydroxymethylglutaryl coenzyme A reductase inhibitor, for example, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for the prevention or treatment of hyperlipidemia, hypercholesterolemia, hypertriglyceridemia, lipid metabolism disorder or atherosclerosis, and more preferably for the prevention or treatment of hyperlipidemia, hypercholesterolemia or atherosclerosis because of lowering blood cholesterol level by inhibiting hydroxymethylglutaryl coenzyme A reductase.

As a fibrate, for example, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for the prevention or treatment of hyperinsulinemia, hyperlipidemia, hypercholesterolemia, hypertriglyceridemia, lipid metabolism disorder or atherosclerosis, and more preferably for the prevention or treatment of hyperlipidemia, hypertriglyceridemia or atherosclerosis because of activating hepatic lipoprotein lipase and enhancing fatty acid oxidation, leading to lowering of blood triglyceride level.

As a $\beta_3$-adrenoceptor agonist, for example, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178, KTO-7924 and the like are illustrated. $\beta_3$-Adrenoceptor agonists are used preferably for the prevention or treatment of obesity, hyperinsulinemia, hyperlipidemia, hypercholesterolemia, hypertriglyceridemia or lipid metabolism disorder, and more preferably for the prevention or treatment of obesity or hyperinsulinemia because of stimulating $\beta_3$-adrenoceptor in adipose tissue and enhancing the fatty acid oxidation, leading to induction of energy expenditure.

As an acyl-coenzyme A cholesterol acyltransferase inhibitor, for example, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A cholesterol acyltransferase inhibitors are used preferably for the prevention or treatment of hyperlipidemia, hypercholesterolemia, hypertriglyceridemia or lipid metabolism disorder, and more preferably for the prevention or treatment of hyperlipidemia or hypercholesterolemia because of lowering blood cholesterol level by inhibiting acyl-coenzyme A cholesterol acyltransferase.

As a thyroid hormone receptor agonist, for example, sodium liothyronine, sodium levothyroxine, KB-2611 and the like are illustrated; as cholesterol absorption inhibitor, for example, ezetimibe, SCH-48461 and the like are illustrated; as lipase inhibitor, for example, orlistat, ATL-962, AZM-131, RED-103004 and the like are illustrated; as carnitine palmitoyltransferase inhibitor, for example, etomoxir and the like are illustrated; as squalene synthase inhibitor, for example, SDZ-268-198, BMS-188494, A-87049, RPR-101821, ZD-9720, RPR-107393, ER-27856, TAK-475 and the like are illustrated; as nicotinic acid derivative, for example, nicotinic acid, nicotinamide, nicomol, niceritrol, acipimox, nicorandil and the like are illustrated; as bile acid sequestrant, for example, colestyramine, colestilan, colesevelam hydrochloride, GT-102-279 and the like are illustrated; as sodium/bile acid cotransporter inhibitor, for example, 264W94, S-8921, SD-5613 and the like are illustrated; and as cholesterol ester transfer protein inhibitor, for example, PNU-107368E, SC-795, JTT-705, CP-529414 and the like are illustrated. These drugs, probcol, microsomal triglyceride transfer protein inhibitor, lipoxygenase inhibitor, squalene epoxidase inhibitor and low-density lipoprotein receptor enhancer are used preferably for the prevention or treatment of hyperlipidemia, hypercholesterolemia, hypertriglyceridemia or lipid metabolism disorder.

As an appetite suppressant, for example, monoamine reuptake inhibitor, serotonin reuptake inhibitor, serotonin releasing stimulant, serotonin agonist (especially 5HT$_{2C}$-agonist), noradrenaline reuptake inhibitor, noradrenaline releasing stimulant, $\alpha_1$-adrenoceptor agonist, $\beta_2$-adrenoceptor agonist, dopamine agonist, cannabinoid receptor antagonist, $\gamma$-aminobutyric acid receptor antagonist, H$_3$-histamine antagonist, L-histidine, leptin, leptin analogue, leptin receptor agonist, melanocortin receptor agonist (especially, MC3-R agonists, MC4-R agonist), $\alpha$-melanocyte stimulating hormone, cocaine- and amphetamine-regulated transcript, mahogany protein, enterostatin agonist, calcitonin, calcitonin-gene-related peptide, bombesin, cholecystokinin agonist (especially CCK-A agonist), corticotropin-releasing hormone, corticotropin-releasing hormone analogue, corticotropin-releasing hormone agonist, urocortin, somatostatin, somatostatin analogues, somatostatin receptor agonist, pituitary adenylate cyclase-activating peptide, brain-derived neurotrophic factor, ciliary neurotrophic factor, thyrotropin-releasing hormone, neurotensin, sauvagine, neuropeptide Y antagonists, PYY, opioid peptide antagonist, galanin antagonist, melanin-concentrating hormone receptor antagonist, agouti-related protein inhibitor and orexin receptor antagonist are illustrated. Concretely, as monoamine reuptake inhibitor, mazindol and the like are illustrated; as serotonin reuptake inhibitor, dexfenfluramine hydrochloride, fenfluramine, sibutramine hydrochloride, fluvoxamine maleate, sertraline hydrochloride and the like are illustrated; as serotonin agonist, inotriptan, (+)-norfenfluramine and the like are illustrated; as noradrenaline reuptake inhibitor, bupropion, GW-320659 and the like are illustrated; as noradrenaline releasing stimulant, rolipram, YM-992 and the like are illustrated; as $\beta_2$-adrenoceptor agonist, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonist, ER-230, doprexin, bromocriptine mesylate and the like are illustrated; as cannabinoid receptor antagonist, rimonabant and the like are illustrated; as $\gamma$-aminobutyric acid receptor antagonist, topiramate and the like are illustrated; as H$_3$-histamine antagonist, GT-2394 and the like are illustrated; as leptin, leptin analogues or leptin receptor agonist, LY-355101 and the like are illustrated; as cholecystokinin agonist (especially CCK-A agonist), SR-146131, SSR-125180, BP-3.200, A-71623, FPL-15849, GI-248573, GW-7178, GI-181771, GW-7854, A-71378 and the like are illustrated; and as neuropeptide Y antagonist, SR-120819-A, PD-160170, NGD-95-1, BIBP-3226, 1229-U-91, CGP-71683, BIBO-3304, CP-671906-01, J-115814 and the like are illustrated. Appetite suppressant are used preferably for the prevention or treatment of diabetes, impaired glucose tolerance, diabetic complications, obesity, hyperlipidemia, hyper-cholesterolemia, hypertriglyceridemia, lipid metabolism disorder, atherosclerosis, hypertension, congestive heart failure, edema, hyperuricemia or gout, and more preferably for the prevention or treatment of obesity because of stimulating or inhibiting the activities of intracerebral monoamines or bioactive peptides in central appetite regulatory system and suppressing the appetite, leading to reduction of energy intake.

As an angiotensin-converting enzyme inhibitor, for example, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are used preferably for the prevention or treatment of diabetic complications or hypertension.

As a neutral endopeptidase inhibitor, for example, omapatrilat, MDL-100240, fasidotril, sampatrilat, GW-660511X, mixanpril, SA-7060, E-4030, SLV-306, ecadotril and the like are illustrated. Neutral endopeptidase inhibitors are used preferably for the prevention or treatment of diabetic complications or hypertension.

As an angiotensin II receptor antagonist, for example, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are used preferably for the prevention or treatment of diabetic complications or hypertension.

As an endothelin-converting enzyme inhibitor, for example, CGS-31447, CGS-35066, SM-19712 and the like are illustrated; as endothelin receptor antagonists, for example, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are used preferably for the prevention or treatment of diabetic complications or hypertension, and more preferably for the prevention or treatment of hypertension.

As a diuretic agent, for example, chlorthalidone, metolazone, cyclopenthiazide, trichloromethiazide, hydrochlorothiazide, hydroflumethiazide, benzylhydrochlorothiazide, penflutizide, methylclothiazide, indapamide, tripamide, mefruside, azosemide, ethacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are used preferably for the prevention or treatment of diabetic complications, hypertension, congestive heart failure or edema, and more preferably for the prevention or treatment of hypertension, congestive heart failure or edema because of reducing blood pressure or improving edema by increasing urinary excretion.

As a calcium antagonist, for example, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, for example, indapamide, todralazine hydrochloride, hydralazine hydrochloride, cadralazine, budralazine and the like are illustrated; as sympathetic blocking agents, for example, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agent, for example, reserpine and the like are illustrated; and as $\alpha_2$-adrenoceptor agonist, for example, clonidine hydrochloride, methyldopa, CHF-1035, guanabenz acetate, guanfacine hydrochloride, moxonidine, lofexidine, talipexole hydrochloride and the like are illustrated. These drugs are used preferably for the prevention or treatment of hypertension.

As an antiplatelets agent, for example, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are used preferably for the prevention or treatment of atherosclerosis or congestive heart failure.

As a uric acid synthesis inhibitor, for example, allopurinol, oxypurinol, febuxostat and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are used preferably for the prevention or treatment of hyperuricemia or gout.

As the other drug combined with the compound of the present invention in the use for the prevention or treatment of diabetes, for example, the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroid dehydrogenase inhibitor, glucagon-like peptide-1, a glucagon-like peptide-1 analogue, a glucagon-like peptide-1 agonist, amylin, an amylin analogue, an amylin agonist and an appetite suppressant is preferable; the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroid-dehydrogenase inhibitor, glucagon-like peptide-1, a glucagon-like peptide-1 analogue, a glucagon-like peptide-1 agonist, amylin, an amylin analogue and an amylin agonist is more preferable; and the drug selected from at least one member of the group consisting of an insulin sensitivity enhancer, an amylase inhibitor, an α-glucosidase inhibitor, a biguanide, an insulin secretion enhancer and an insulin or insulin analogue is most preferable. Similarly, in the use for the prevention or treatment of diabetic complications, for example, the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, glycogen synthase kinase-3 inhibitors, an 11β-hydroxysteroid dehydrogenase inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an antidiarrhoics, a cathartics, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the drug selected from at least one member of the group consisting of an aldose reductase inhibitor, an angiotensin-converting enzyme inhibitor, a neutral endopeptidase inhibitor and an angiotensin II receptor antagonist is more preferable. Furthermore, in the use for the prevention or treatment of obesity, the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroid-dehydrogenase inhibitor, glucagon-like peptide-1, a glucagon-like peptide-1 analogue, a glucagon-like peptide-1 agonist, amylin, an amylin analogue, an amylin agonist, a $β_3$-adrenoceptor agonist and an appetite suppressant is preferable; and the drug selected from at least one member of the group consisting of an amylase inhibitor, an α-glucosidase inhibitor, a $β_3$-adrenoceptor agonist and an appetite suppressant is more preferable.

EXAMPLES

The present invention is further illustrated in more detail by way of the following Examples and Test Examples. However, the present invention is not limited thereto.

Reference Example 1

3-Bromo-4-methyl-1-(toluene-4-sulfonyl)-1H-indole

To a solution of 4-methyl-1H-indole (2.53 g) in N,N-dimethylformamide (20 mL) was added 55% sodium hydride (0.88 g) under ice-cooling, and the mixture was stirred at the same temperature for 5 minutes. To this mixture was added p-toluenesulfonyl chloride (4.04 g) at the same temperature, and the mixture was stirred at room temperature for 2 hours. The reaction mixture was poured into 1 mol/L hydrochloric acid, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=5/1) to give 4-methyl-1-(toluene-4-sulfonyl)-1H-indole (4.99 g). This material was dissolved in dichloromethane (100 mL). To the solution was added bromine (26% dichloromethane solution, 12.62 g) in a dropwise manner under ice-cooling, and the mixture was stirred at the same temperature for 15 minutes. The solvent was removed under reduced pressure, and the residue was purified by column chromatography on silica gel (eluent: n-hexane/ethyl acetate=5/1). The purified material was crystallized from n-hexane-diethyl ether, and the crystals were collected by filtration. The crystals were washed with n-hexane and dried under reduced pressure to give the title compound (4.8 g).

Reference Examples 2 to 4

Reference Examples 2 to 4 were prepared in a similar manner to that described in Reference Example 1 using the corresponding starting materials.

Reference Example 5

3-(2,3,4,6-Tetra-O-benzyl-β-D-glucopyranosyl)-4-methyl-1H-indole

To a solution of 3-bromo-4-methyl-1-(toluene-4-sulfonyl)-1H-indole (2.03 g) in tetrahydrofuran (20 mL) was added n-butyl lithium (2.71 mol/L n-hexane solution, 2.0 mL) at −78° C., and the mixture was stirred at the same temperature for 30 minutes. To this mixture was added a solution of 2,3,4,6-tetra-O-benzyl-D-glucono-1,5-lactone (2.5 g) in tetrahydrofuran (8 mL) at the same temperature, and the mixture was stirred at the same temperature for 10 minutes, and stirred under ice-cooling for 1 hour. To the reaction mixture was added a saturated aqueous ammonium chloride solution, and the resulting mixture was extracted with diethyl ether. The extract was washed with a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=5/1-3/1) to give the corresponding adduct (2.76 g). This material was dissolved in acetonitrile (33 mL). To the solution was added triethylsilane (1.07 mL). To the mixture was added boron trifluoride diethyl ether complex (0.46 mL) at −15° C., and the mixture was stirred at the same temperature for 15 minutes, and stirred at room temperature for 30 minutes. To the reaction mixture was added 20% aqueous potassium carbonate solution, and the resulting mixture was extracted with diethylether. The extract was washed with water and brine successively, and dried over anhydrous sodium sulfate. The solvent was removed under reduced pressure, and the residue was purified by column chromatography on silica gel (eluent: n-hexane/ethyl acetate=6/1-4/1) to give 3-(2,3,4,6-tetra-O-benzyl-β-D-glucopyranosyl)-4-methyl-1-(toluene-4-sulfonyl)-1H-indole (2.45 g). This material was dissolved in a mixed solvent of ethanol (30 mL) and tetrahydrofuran (15 mL). To the solution was added potassium hydroxide (3.4 g), and the mixture was stirred at 50° C. overnight. The reaction mixture was poured into 1 mol/L hydrochloric acid (70 mL), and the resulting mixture was extracted with ethylacetate. The extract was washed with water and brine successively, and dried over an hydrous sodium sulfate. The solvent was removed under reduced pressure, and the residue was purified by column chromatography on silica gel (eluent: n-hexane/ethyl acetate=4/1-2/1) to give the title compound (1.66 g).

Reference Examples 6 to 8

Reference Examples 6 to 8 were prepared in a similar manner to that described in Reference Example 5 using the corresponding starting materials.

The structures and NMR spectrum data of the compounds of Reference Examples 1 to 8 are described in Table 1.

TABLE 1

| No. | Structure | $^1$H-NMR (CDCl$_3$) δ ppm: |
|---|---|---|
| Reference Example 1 | 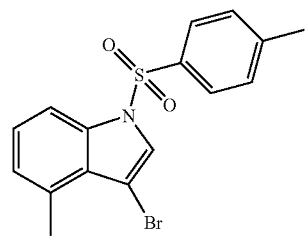 | 2.35 (3H, s), 2.73 (3H, s), 6.99 (1H, d, J = 7.4 Hz), 7.15-7.3 (3H, m), 7.61 (1H, s), 7.7-7.8 (2H, m), 7.85 (1H, d, J = 8.4 Hz). |
| Reference Example 2 | 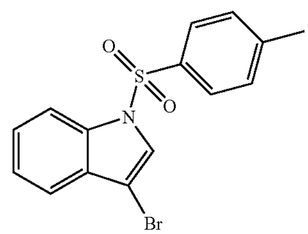 | 2.35 (3H, s), 7.2-7.35 (3H, m), 7.35-7.4 (1H, m), 7.45-7.55 (1H, m), 7.62 (1H, s), 7.7-7.8 (2H, m), 7.95-8.05 (1H, m). |
| Reference Example 3 | 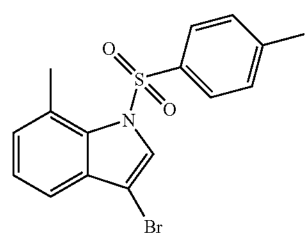 | 2.38 (3H, s), 2.55 (3H, s), 7.08 (1H, d, J = 7.4 Hz), 7.15-7.3 (3H, m), 7.37 (1H, d, J = 7.5 Hz), 7.5-7.6 (2H, m), 7.85 (1H, s). |
| Reference Example 4 | 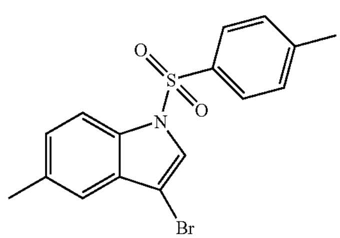 | 2.34 (3H, s), 2.43 (3H, s), 7.15-7.3 (4H, m), 7.56 (1H, s), 7.7-7.8 (2H, m), 7.86 (1H, d, J = 8.5 Hz). |
| Reference Example 5 | 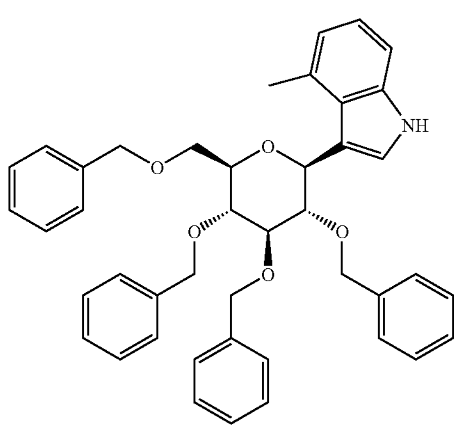 | 2.74 (3H, s), 3.6-3.7 (1H, m), 3.75-3.9 (5H, m), 4.04 (1H, d, J = 10.6 Hz), 4.45 (1H, d, J = 10.6 Hz), 4.51 (1H, d, J = 12.1 Hz), 4.6 (1H, d, J = 12.1 Hz), 4.64 (1H, d, J = 10.8 Hz), 4.81 (1H, d, J = 8.9 Hz), 4.85-4.95 (2H, m), 4.96 (1H, d, J = 10.9 Hz), 6.8-6.95 (3H, m), 7.05-7.4 (21H, m), 8.13 (1H, brs). |

TABLE 1-continued
| No. | Structure | $^1$H-NMR (CDCl$_3$) δ ppm: |
|---|---|---|
| Reference Example 6 | 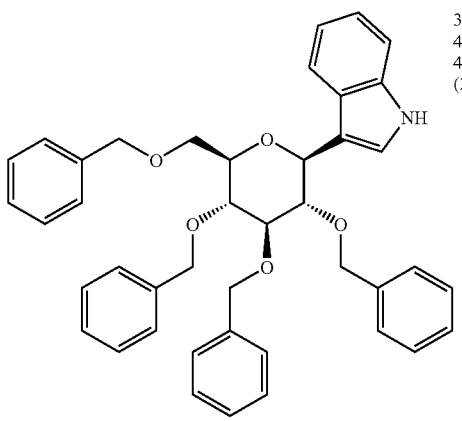 | 3.6-3.7 (1H, m), 3.7-4.0 (6H, m), 4.32 (1H, d, J = 10.4 Hz), 4.5-4.6 (2H, m), 4.6-4.75 (2H, m), 4.85-4.95 (2H, m), 4.96 (1H, d, J = 11.0 Hz), 6.8-6.85 (2H, m), 7.05-7.45 (22H, m), 7.86 (1H, d, J = 7.9 Hz), 8.12 (1H, brs). |
| Reference Example 7 | 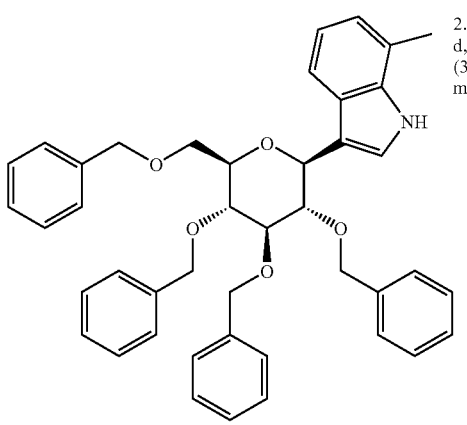 | 2.5 (3H, s), 3.6-3.7 (1H, m), 3.75-3.95 (6H, m), 4.32 (1H, d, J = 10.7 Hz), 4.5-4.6 (2H, m), 4.6-4.75 (2H, m), 4.85-5.0 (3H, m), 6.8-6.9 (2H, m), 6.95-7.2 (5H, m), 7.2-7.4 (16H, m), 7.65-7.75 (1H, m), 8.01 (1H, brs). |
| Reference Example 8 | 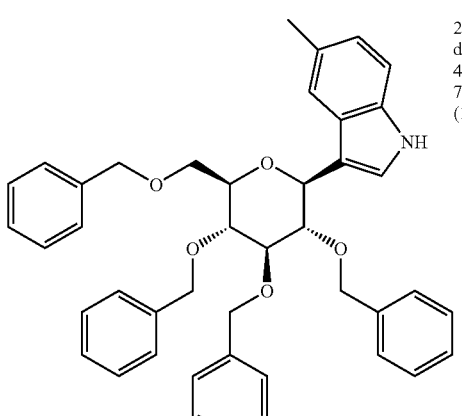 | 2.37 (3H, s), 3.6-3.7 (1H, m), 3.75-4.0 (6H, m), 4.33 (1H, d, J = 10.3 Hz), 4.5-4.6 (2H, m), 4.65-4.75 (2H, m), 4.85-4.95 (2H, m), 4.97 (1H, d, J = 10.9 Hz), 6.8-6.9 (2H, m), 7.02 (1H, dd, J = 8.4, 1.3 Hz), 7.1-7.2 (3H, m), 7.2-7.4 (17H, m), 7.6-7.65 (1H, m), 8.0 (1H, brs). |

Reference Examples 9 to 19

Reference Examples 9 to 19 were prepared in a similar manner to that described in Reference Example 1 using the corresponding starting materials.

Reference Example 20

3-Bromo-7-fluoro-5-methyl-1-(toluene-4-sulfonyl)-1H-indole

To a solution of 3-fluoro-4-nitrotoluene (3.1 g) in tetra hydrofuran (160 mL) was added vinyl magnesium bromide (1.0 mol/L tetra hydrofuran solution, 60.0 mL) at −40° C., and the mixture was stirred at the same temperature for 1 hour. To the mixture was added a saturated aqueous ammonium chloride solution, and the resulting mixture was stirred at room temperature for 1 hour. The mixture was extracted with diethyl ether. The extract was washed with a saturated aqueous ammonium chloride solution, water and brine successively, and dried over anhydrous sodium sulfate. The solvent was removed under reduced pressure, and the residue was purified by column chromatography on amino-propylated silica gel (eluent: n-hexane/ethyl acetate=19/1-4/1) to give 7-fluoro-5-methyl-1H-indole (0.96 g). The title compound was prepared in a similar manner to that described in Reference Example 1 using this material instead of 4-methyl-1H-indole.

Reference Examples 21 to 25

Reference Examples 21 to 25 were prepared in a similar manner to that described in Reference Example 20 using the corresponding starting materials.

The structures and NMR spectrum data of the compounds of Reference Examples 9 to 25 are described in Table 2.

TABLE 2

| No. | Structure | $^1$H-NMR (CDCl$_3$) δ ppm: |
|---|---|---|
| Reference Example 9 | 4-F, 3-Br, 1-Ts indole | 2.37 (3H, s), 6.9-7.0 (1H, m), 7.25-7.35 (3H, m), 7.57 (1H, s), 7.75-7.85 (3H, m) |
| Reference Example 10 | 4-Cl, 3-Br, 1-Ts indole | 2.37 (3H, s), 7.2-7.3 (4H, m), 7.67 (1H, s), 7.7-7.8 (2H, m), 7.9-8.0 (1H, m) |
| Reference Example 11 | 5-F, 3-Br, 1-Ts indole | 2.36 (3H, s), 7.05-7.2 (2H, m), 7.2-7.3 (2H, m), 7.64 (1H, s), 7.7-7.8 (2H, m), 7.9-8.0 (1H, m) |
| Reference Example 12 | 5-Cl, 3-Br, 1-Ts indole | 2.37 (3H, s), 7.2-7.3 (2H, m), 7.33 (1H, dd, J = 8.8, 2.1 Hz), 7.47 (1H, d, J = 2.1 Hz), 7.63 (1H, s), 7.7-7.8 (2H, m), 7.92 (1H, d, J = 8.8 Hz) |

TABLE 2-continued

| No. | Structure | ¹H-NMR (CDCl₃) δ ppm: |
|---|---|---|
| Reference Example 13 | 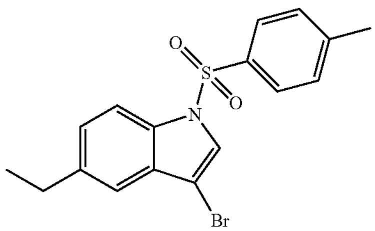 | 1.26 (3H, t, J = 7.6 Hz), 2.35 (3H, s), 2.73 (2H, q, J = 7.6 Hz), 7.15-7.3 (4H, m), 7.57 (1H, s), 7.7-7.8 (2H, m), 7.88 (1H, d, J = 8.6 Hz) |
| Reference Example 14 | 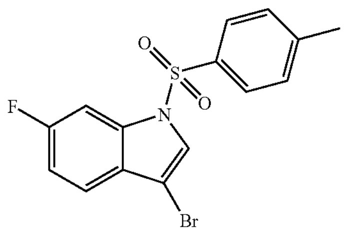 | 2.37 (3H, s), 7.0-7.1 (1H, m), 7.2-7.3 (2H, m), 7.4-7.45 (1H, m), 7.59 (1H, s), 7.7-7.8 (3H, m) |
| Reference Example 15 | 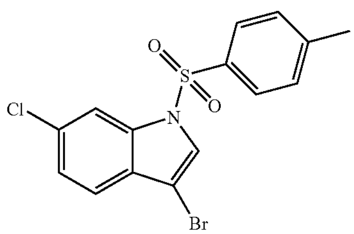 | 2.37 (3H, s), 7.25-7.3 (3H, m), 7.4 (1H, d, J = 8.2 Hz), 7.59 (1H, s), 7.75-7.8 (2H, m), 8.02 (1H, d, J = 1.7 Hz) |
| Reference Example 16 | 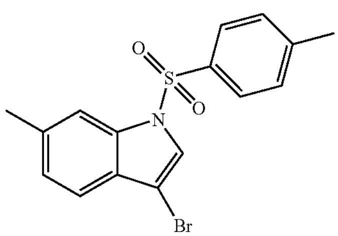 | 2.35 (3H, s), 2.49 (3H, s), 7.1-7.15 (1H, m), 7.2-7.3 (2H, m), 7.3-7.4 (1H, m), 7.53 (1H, s), 7.7-7.85 (3H, m) |
| Reference Example 17 | 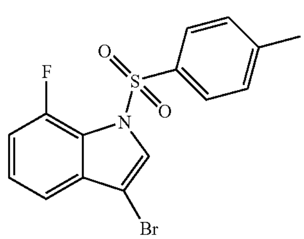 | 2.39 (3H, s), 6.95-7.1 (1H, m), 7.15-7.25 (1H, m), 7.25-7.35 (3H, m), 7.8-7.9 (3H, m) |
| Reference Example 18 | 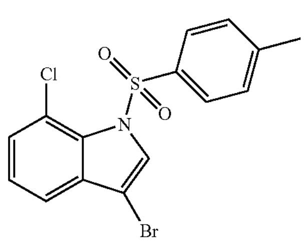 | 2.41 (3H, s), 7.15-7.25 (1H, m), 7.25-7.35 (3H, m), 7.46 (1H, dd, J = 7.9, 1.3 Hz), 7.7-7.75 (2H, m), 7.98 (1H, s) |

TABLE 2-continued

| No. | Structure | $^1$H-NMR (CDCl$_3$) δ ppm: |
|---|---|---|
| Reference Example 19 | 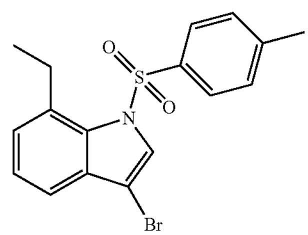 | 1.05-1.15 (3H, m), 2.3-2.4 (3H, m), 3.0-3.1 (2H, m), 7.15-7.3 (4H, m), 7.3-7.45 (1H, m), 7.5-7.6 (2H, m), 7.7-7.85 (1H, m) |
| Reference Example 20 | 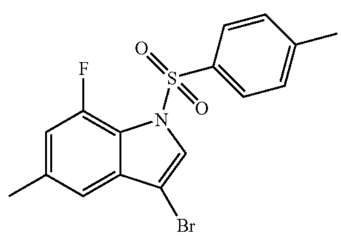 | 2.38 (3H, s), 2.39 (3H, s), 6.8-6.9 (1H, m), 7.05-7.1 (1H, m), 7.25-7.3 (2H, m), 7.75-7.85 (3H, m) |
| Reference Example 21 | 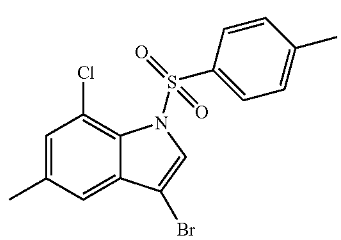 | 2.38 (3H, s), 2.4 (3H, s), 7.1-7.15 (1H, m), 7.2-7.3 (3H, m), 7.65-7.75 (2H, m), 7.91 (1H, s) |
| Reference Example 22 | 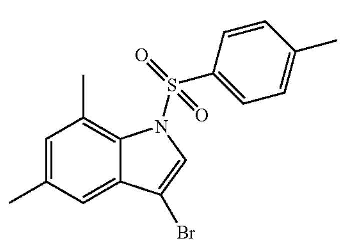 | 2.35-2.4 (6H, m), 2.52 (3H, s), 6.85-6.95 (1H, m), 7.1-7.25 (3H, m), 7.5-7.6 (2H, m), 7.79 (1H, s) |
| Reference Example 23 | 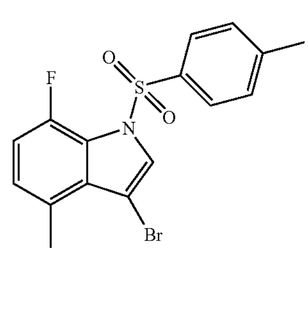 | 2.39 (3H, s), 2.71 (3H, s), 6.8-6.9 (2H, m), 7.25-7.35 (2H, m), 7.75-7.85 (3H, m) |

TABLE 2-continued

| No. | Structure | $^1$H-NMR (CDCl$_3$) δ ppm: |
|---|---|---|
| Reference Example 24 | [structure: 7-chloro-4-methyl-3-bromo-1-tosyl-1H-indole] | 2.41 (3H, s), 2.77 (3H, s), 6.85-6.95 (1H, m), 7.05-7.15 (1H, m), 7.25-7.3 (2H, m), 7.65-7.75 (2H, m), 7.96 (1H, s) |
| Reference Example 25 | [structure: 4,7-dimethyl-3-bromo-1-tosyl-1H-indole] | 2.38 (3H, s), 2.47 (3H, s), 2.74 (3H, s), 6.85-6.95 (2H, m), 7.2-7.3 (2H, m), 7.5-7.6 (2H, m), 7.83 (1H, s) |

Reference Examples 26 to 42

Reference Examples 26 to 42 were prepared in a similar manner to that described in Reference Example 5 using the corresponding starting materials.

Reference Example 43

3-(2,3,4,6-Tetra-O-benzyl-β-D-glucopyranosyl)-2-fluoro-1H-indole

To a solution of 3-bromo-1-(toluene-4-sulfonyl)-1H-indole (1.22 g) in tetra hydrofuran (25 mL) was added n-butyl lithium (2.59 mol/L n-hexane solution, 1.24 mL) at −78° C., and the mixture was stirred at the same temperature for 30 minutes. To this mixture was added a solution of 2,3,4,6-tetra-O-benzyl-D-glucono-1,5-lactone (1.5 g) in tetra hydrofuran (7 mL) at the same temperature, and the mixture was stirred at the same temperature for 10 minutes, and stirred under ice-cooling for 1 hour. To the reaction mixture was added a saturated aqueous ammonium chloride solution, and the resulting mixture was extracted with diethyl ether. The extract was washed with a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=5/1-3/1) to give the corresponding adduct (2.2 g). This material was dissolved in acetonitrile (27 mL). To the solution was added triethylsilane (0.87 mL). To the mixture was added boron trifluoride diethyl ether complex (0.38 mL) at −15° C., and the mixture was stirred at the same temperature for 15 minutes, and stirred at room temperature for 1 hour. To the reaction mixture was added 20% aqueous potassium carbonate solution, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=5/1) to give 3-(2,3,4,6-tetra-O-benzyl-β-D-glucopyranosyl)-1-(toluene-4-sulfonyl)-1H-indole (1.59 g). To a solution of diisopropylamine (0.026 mL) in tetra hydrofuran (3 mL) was added n-butyl lithium (2.67 mol/L n-hexane solution, 0.063 mL) at −78° C., and the mixture was stirred at the same temperature for 15 minutes. To this mixture was added a solution of 3-(2,3,4,6-tetra-O-benzyl-β-D-glucopyranosyl)-1-(toluene-4-sulfonyl)-1H-indole (0.11 g) in tetra hydrofuran (1 mL) at the same temperature, and the mixture was stirred at the same temperature for 30 minutes. To this mixture was added N-fluorobenzenesulfonimide (0.13 g) at the same temperature, and the mixture was stirred at the same temperature for 30 minutes, and stirred at room temperature for 1 hour. The reaction mixture was poured into a saturated aqueous ammonium chloride solution, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=6/1) to give 3-(2, 3,4,6-tetra-O-benzyl-β-D-glucopyranosyl)-2-fluoro-1-(toluene-4-sulfonyl)-1H-indole (57 mg). This material was dissolved in a mixed solvent of ethanol (2 mL) and tetra hydrofuran (1 mL). To the solution was added potassium hydroxide (79 mg), and the mixture was stirred at 50° C. overnight. The reaction mixture was poured into 1 mol/L hydrochloric acid (3 mL), and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=3/1) to give the title compound (35 mg).

Reference Example 44

Reference Example 44 was prepared in a similar manner to that described in Reference Example 43 using methyl iodide instead of N-fluorobenzenesulfonimide.

The structures and NMR spectrum data of the compounds of Reference Examples 26 to 44 are described in Table 3.

TABLE 3
| No. | Structure | $^1$H-NMR (CDCl$_3$) δ ppm: |
|---|---|---|
| Reference Example 26 | 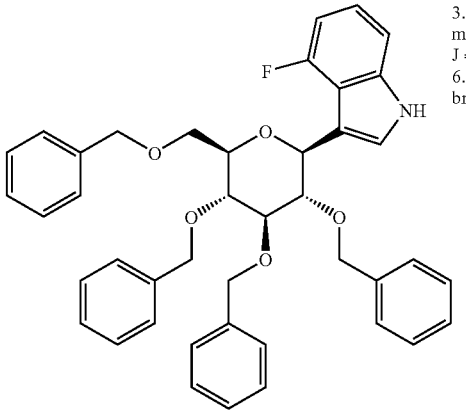 | 3.6-3.75 (1H, m), 3.75-3.9 (4H, m), 3.9-4.0 (2H, m), 4.43 (1H, d, J = 10.5 Hz), 4.53 (1H, d, J = 12.2 Hz), 4.6-4.7 (3H, m), 4.85-5.0 (3H, m), 6.75-6.85 (3H, m), 7.05-7.4 (21H, m), 8.28 (1H, brs) |
| Reference Example 27 | 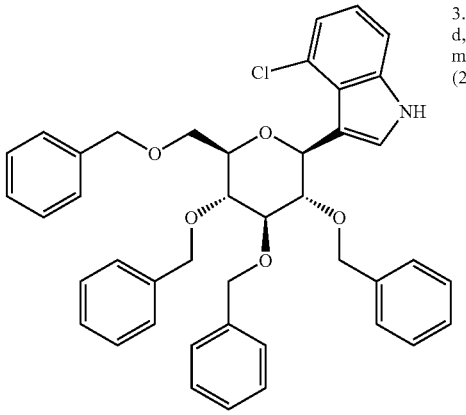 | 3.65-3.75 (1H, m), 3.75-4.05 (5H, m), 4.17 (1H, d, J = 10.2 Hz), 4.45-4.6 (2H, m), 4.6-4.7 (2H, m), 4.85-5.0 (3H, m), 5.1-5.25 (1H, m), 6.85-6.9 (2H, m), 7.0-7.4 (22H, m), 8.26 (1H, brs) |
| Reference Example 28 | 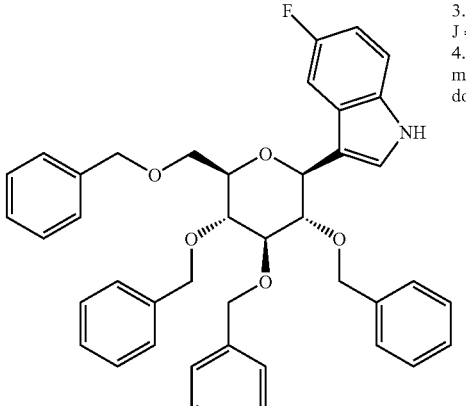 | 3.6-3.7 (1H, m), 3.75-3.95 (6H, m), 4.37 (1H, d, J = 10.6 Hz), 4.45-4.6 (2H, m), 4.6-4.7 (2H, m), 4.85-5.0 (3H, m), 6.8-6.9 (2H, m), 6.9-7.0 (1H, m), 7.1-7.2 (3H, m), 7.2-7.4 (17H, m), 7.51 (1H, dd, J = 9.6, 2.4 Hz), 8.09 (1H, brs) |

TABLE 3-continued

| No. | Structure | $^1$H-NMR (CDCl$_3$) δ ppm: |
|---|---|---|
| Reference Example 29 | 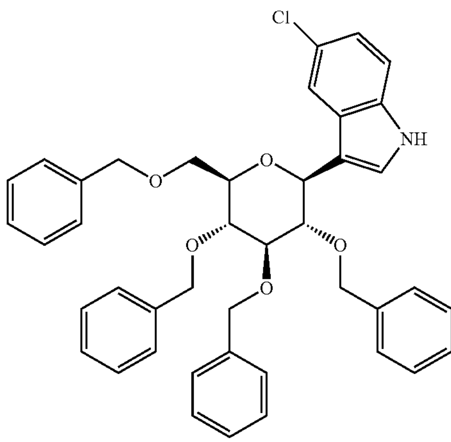 | 3.6-3.7 (1H, m), 3.75-3.95 (6H, m), 4.37 (1H, d, J = 10.3 Hz), 4.45-4.6 (2H, m), 4.6-4.7 (2H, m), 4.85-5.0 (3H, m), 6.8-6.9 (2H, m), 7.1-7.2 (4H, m), 7.2-7.4 (17H, m), 7.82 (1H, d, J = 1.7 Hz), 8.16 (1H, brs) |
| Reference Example 30 | 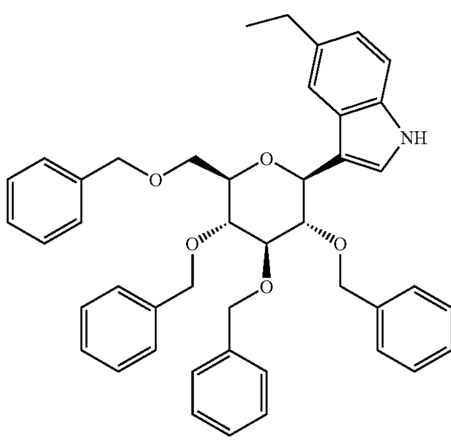 | 1.21 (3H, t, J = 7.5 Hz), 2.66 (2H, q, J = 7.5 Hz), 3.6-3.7 (1H, m), 3.75-4.05 (6H, m), 4.32 (1H, d, J = 10.2 Hz), 4.5-4.6 (2H, m), 4.65-4.75 (2H, m), 4.85-5.0 (3H, m), 6.8-6.9 (2H, m), 7.0-7.2 (4H, m), 7.2-7.4 (17H, m), 7.6-7.7 (1H, m), 8.03 (1H, brs) |
| Reference Example 31 | 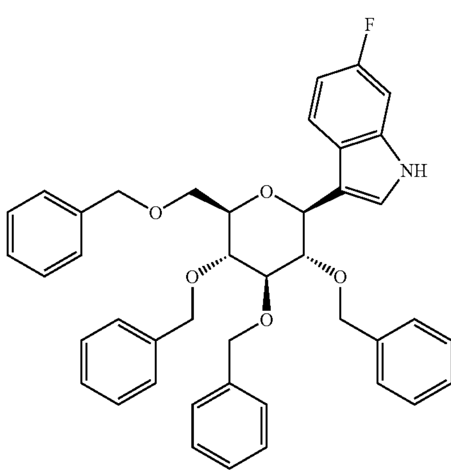 | 3.6-3.7 (1H, m), 3.75-3.95 (6H, m), 4.35 (1H, d, J = 10.4 Hz), 4.5-4.6 (2H, m), 4.6-4.75 (2H, m), 4.85-5.0 (3H, m), 6.8-6.9 (3H, m), 7.0-7.1 (1H, m), 7.1-7.2 (3H, m), 7.2-7.4 (16H, m), 7.7-7.8 (1H, m), 8.09 (1H, brs) |

TABLE 3-continued
| No. | Structure | ¹H-NMR (CDCl₃) δ ppm: |
|---|---|---|
| Reference Example 32 | 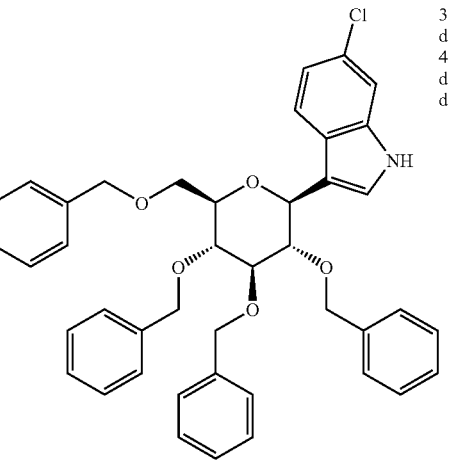 | 3.6-3.65 (1H, m), 3.75-3.95 (6H, m), 4.36 (1H, d, J = 10.4 Hz), 4.5-4.6 (2H, m), 4.6-4.7 (2H, m), 4.85-5.0 (3H, m), 6.8-6.85 (2H, m), 7.04 (1H, dd, J = 8.5, 2.0 Hz), 7.1-7.4 (20H, m), 7.73 (1H, d, J = 8.5 Hz), 8.08 (1H, brs) |
| Reference Example 33 | 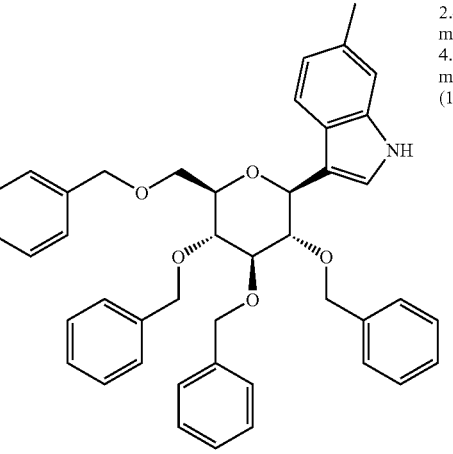 | 2.46 (3H, s), 3.6-3.65 (1H, m), 3.75-3.95 (6H, m), 4.31 (1H, d, J = 10.4 Hz), 4.5-4.6 (2H, m), 4.6-4.75 (2H, m), 4.85-5.0 (3H, m), 6.8-6.9 (2H, m), 6.9-6.95 (1H, m), 7.1-7.4 (20H, m), 7.73 (1H, d, J = 7.8 Hz), 7.97 (1H, brs) |
| Reference Example 34 | 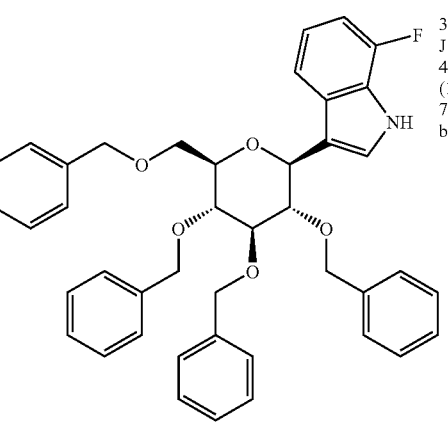 | 3.6-3.7 (1H, m), 3.75-3.95 (6H, m), 4.37 (1H, d, J = 10.3 Hz), 4.5-4.6 (2H, m), 4.6-4.75 (2H, m), 4.85-5.0 (3H, m), 6.8-6.85 (2H, m), 6.85-6.95 (1H, m), 6.95-7.05 (1H, m), 7.05-7.2 (3H, m), 7.2-7.4 (16H, m), 7.55-7.65 (1H, m), 8.27 (1H, brs) |

TABLE 3-continued
| No. | Structure | $^1$H-NMR (CDCl$_3$) δ ppm: |
|---|---|---|
| Reference Example 35 | 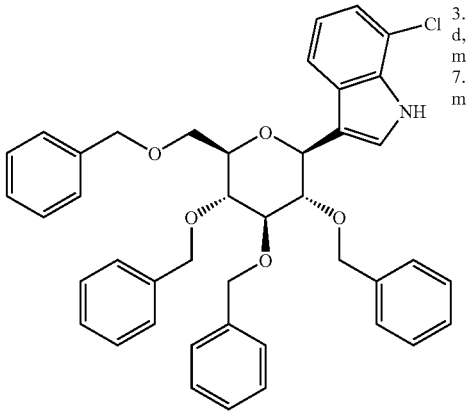 | 3.55-3.7 (1H, m), 3.75-3.95 (6H, m), 4.38 (1H, d, J = 10.6 Hz), 4.5-4.6 (2H, m), 4.6-4.75 (2H, m), 4.85-5.0 (3H, m), 6.75-6.85 (2H, m), 6.95-7.05 (1H, m), 7.05-7.4 (20H, m), 7.7-7.75 (1H, m), 8.3 (1H, brs) |
| Reference Example 36 | 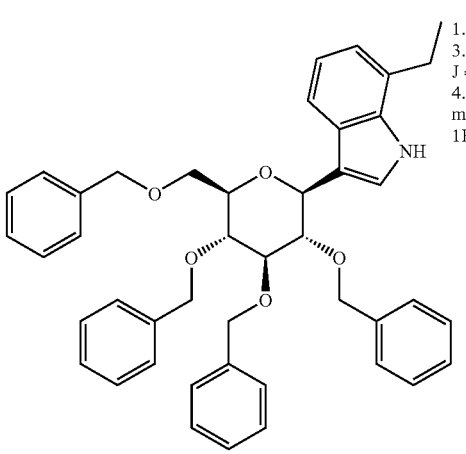 | 1.37 (3H, t, J = 7.6 Hz), 2.87 (2H, q, J = 7.6 Hz), 3.6-3.7 (1H, m), 3.75-4.0 (6H, m), 4.33 (1H, d, J = 10.5 Hz), 4.5-4.6 (2H, m), 4.6-4.75 (2H, m), 4.85-5.0 (3H, m), 6.8-6.9 (2H, m), 7.0-7.2 (5H, m), 7.2-7.4 (16H, m), 7.65-7.75 (1H, m), 8.06 1H, brs) |
| Reference Example 37 | 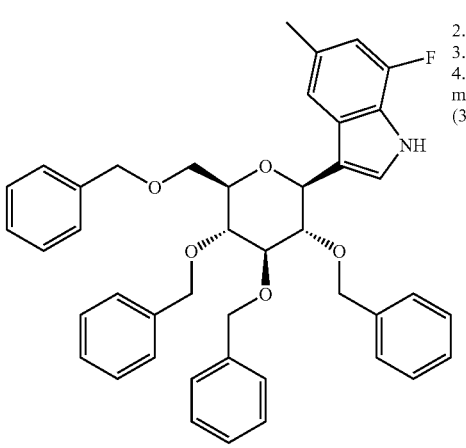 | 2.34 (3H, s), 3.6-3.7 (1H, m), 3.75-3.9 (5H, m), 3.9-4.0 (1H, m), 4.37 (1H, d, J = 10.4 Hz), 4.45-4.6 (2H, m), 4.65-4.75 (2H, m), 4.85-5.0 (3H, m), 6.7-6.8 (1H, m), 6.8-6.9 (2H, m), 7.1-7.2 (3H, m), 7.2-7.4 (17H, m), 8.17 (1H, brs) |

TABLE 3-continued

| No. | Structure | ¹H-NMR (CDCl₃) δ ppm: |
|---|---|---|
| Reference Example 38 | 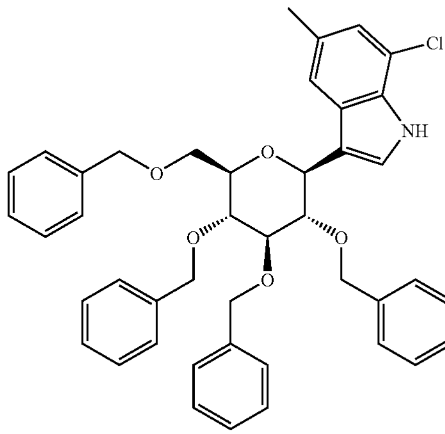 | 2.34 (3H, s), 3.6-3.65 (1H, m), 3.75-3.9 (5H, m), 3.9-4.0 (1H, m), 4.37 (1H, d, J = 10.5 Hz), 4.45-4.6 (2H, m), 4.6-4.75 (2H, m), 4.85-5.0 (3H, m), 6.8-6.9 (2H, m), 7.0-7.05 (1H, m), 7.1-7.2 (3H, m), 7.2-7.4 (16H, m), 7.45-7.5 (1H, m), 8.2 (1H, brs) |
| Reference Example 39 | 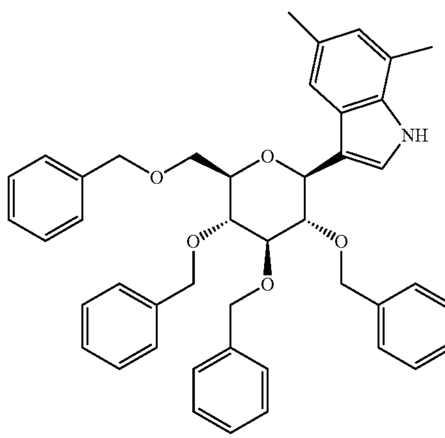 | 2.35 (3H, s), 2.45 (3H, s), 3.6-3.65 (1H, m), 3.75-3.85 (3H, m), 3.85-4.0 (3H, m), 4.32 (1H, d, J = 10.5 Hz), 4.5-4.6 (2H, m), 4.65-4.75 (2H, m), 4.85-5.0 (3H, m), 6.8-6.9 (3H, m), 7.1-7.2 (3H, m), 7.2-7.4 (16H, m), 7.45-7.5 (1H, m), 7.93 (1H, brs) |
| Reference Example 40 | 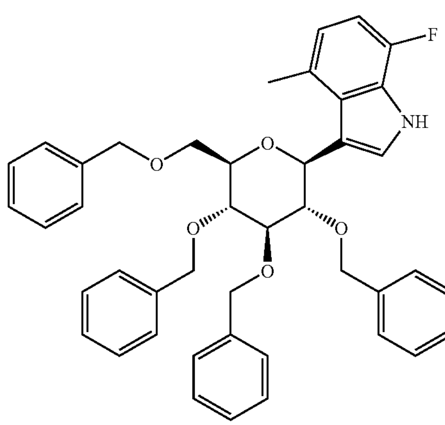 | 2.67 (3H, s), 3.6-3.7 (1H, m), 3.7-3.9 (5H, m), 4.05 (1H, d, J = 10.3 Hz), 4.45-4.55 (2H, m), 4.55-4.7 (2H, m), 4.79 (1H, d, J = 9.5 Hz), 4.85-5.0 (3H, m), 6.7-6.85 (4H, m), 7.05-7.4 (19H, m), 8.29 (1H, brs) |

TABLE 3-continued
| No. | Structure | $^1$H-NMR (CDCl$_3$) δ ppm: |
|---|---|---|
| Reference Example 41 | 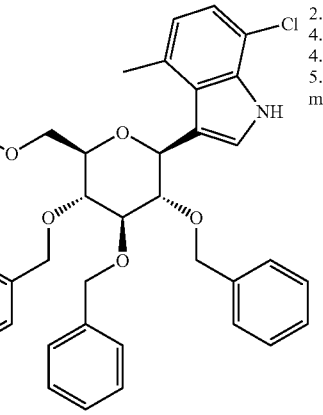 | 2.68 (3H, s), 3.6-3.7 (1H, m), 3.7-3.9 (5H, m), 4.06 (1H, d, J = 11.0 Hz), 4.45-4.55 (2H, m), 4.55-4.7 (2H, m), 4.78 (1H, d, J = 9.3 Hz), 4.85-5.0 (3H, m), 6.75-6.85 (3H, m), 7.05-7.4 (20H, m), 8.33 (1H, brs) |
| Reference Example 42 | 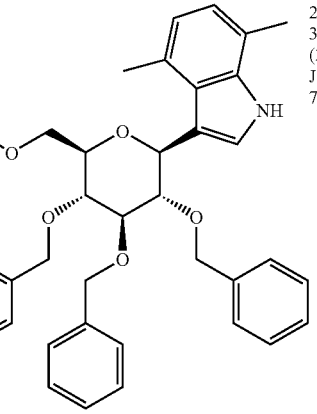 | 2.45 (3H, s), 2.72 (3H, s), 3.6-3.7 (1H, m), 3.75-3.9 (5H, m), 4.07 (1H, d, J = 10.6 Hz), 4.4-4.55 (2H, m), 4.55-4.7 (2H, m), 4.82 (1H, d, J = 8.8 Hz), 4.85-5.0 (3H, m), 6.8-6.95 (4H, m), 7.05-7.4 (19H, m), 8.05 (1H, brs) |
| Reference Example 43 | 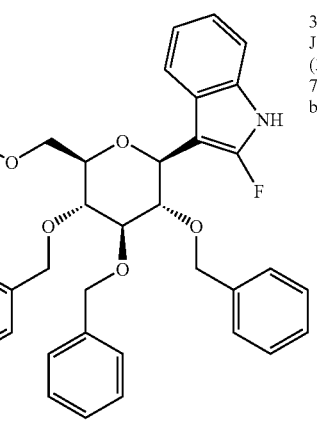 | 3.6-3.7 (1H, m), 3.75-4.0 (6H, m), 4.44 (1H, d, J = 10.8 Hz), 4.53 (1H, d, J = 11.9 Hz), 4.55-4.75 (3H, m), 4.85-5.0 (3H, m), 6.85-6.95 (2H, m), 7.05-7.4 (21H, m), 7.7-7.75 (1H, m), 7.85 (1H, brs) |

TABLE 3-continued

| No. | Structure | ¹H-NMR (CDCl₃) δ ppm: |
|---|---|---|
| Reference Example 44 | 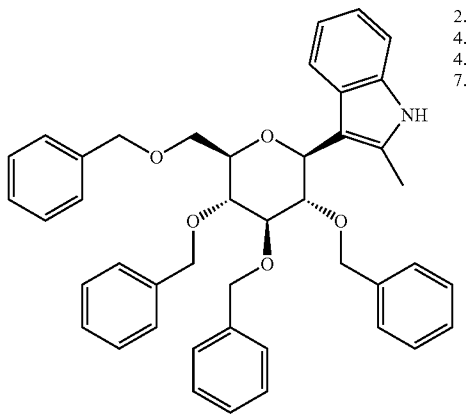 | 2.38 (3H, s), 3.6-3.7 (1H, m), 3.7-4.0 (6H, m), 4.31 (1H, d, J = 10.3 Hz), 4.5-4.6 (2H, m), 4.6-4.75 (2H, m), 4.85-5.0 (3H, m), 6.8-6.9 (2H, m), 7.0-7.4 (21H, m), 7.75-7.85 (2H, m) |

Reference Example 45

4-Isobutylbenzyl bromide

To a solution of 4-isobutylbenzaldehyde (1.0 g) in tetrahydrofuran (10 mL) were added water (1 mL) and sodium borohydride (0.26 g) under ice-cooling, and the mixture was stirred at the same temperature for 30 minutes. The reaction mixture was diluted with water, and the resulting mixture was extracted with diethylether. The extract was washed with brine, and dried over anhydrous sodium sulfate. The solvent was removed under reduced pressure, and the residue was dissolved in ethyl acetate (12 mL). To the solution was added triethylamine (1.12 mL). To the mixture was added methanesulfonyl chloride (0.53 mL) under ice-cooling, and the mixture was stirred at the same temperature for 30 minutes. The insoluble material was removed by filtration. To the filtrate were added ethyl acetate (6 mL) and lithium bromide monohydrate (3.23 g), and the mixture was stirred at 55° C. for 2 hours. The reaction mixture was poured into water, and the resulting mixture was extracted with ethyl acetate. The extract was washed with water and brine successively, and dried over anhydrous sodium sulfate. The solvent was removed under reduced pressure to give the title compound (1.29 g).

Reference Example 46

2-Fluoro-4-methoxybenzyl bromide

Step 1

To a suspension of 4-bromo-3-fluorophenol (2.87 g) and cesium carbonate (12.2 g) in N,N-dimethylformamide (30 mL) was added methyliodide (1.87 mL) at room temperature, and the mixture was stirred at room temperature overnight. The reaction mixture was poured into water, and the resulting mixture was extracted with diethyl ether. The extract was washed with water and brine successively, and dried over anhydrous sodium sulfate. The solvent was removed under reduced pressure to give 1-bromo-2-fluoro-4-methoxybenzene (3.02 g).

Step 2

To a solution of 1-bromo-2-fluoro-4-methoxybenzene (3.02 g) in tetrahydrofuran (75 mL) was added n-butyl lithium (2.71 mol/L n-hexane solution, 6.0 mL) at −78° C., and the mixture was stirred at the same temperature for 30 minutes. To this mixture was added N,N-dimethylformamide (1.7 mL) at the same temperature, and the mixture was stirred under ice-cooling for 1 hour. The reaction mixture was poured into a saturated aqueous ammonium chloride solution, and the resulting mixture was extracted with diethyl ether. The extract was washed with a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=8/1-4/1) to give 2-fluoro-4-methoxybenzaldehyde (1.54 g). The title compound was prepared in a similar manner to that described in Reference Example 45 using this material instead of 4-isobutylbenzaldehyde.

Reference Examples 47 and 48

Reference Examples 47 and 48 were prepared in a similar manner to that described in Reference Example 46 using the corresponding starting materials.

Reference Example 49

2-Chloro-4-methoxybenzyl bromide

To a suspension of 2-chloro-4-hydroxybenzaldehyde (0.50 g) and potassium carbonate (1.1 g) in N,N-dimethylformamide (5 mL) was added methyl iodide (0.40 mL) at room temperature, and the mixture was stirred at room temperature for 5 hours. The reaction mixture was poured into water, and the resulting mixture was extracted with diethyl ether. The extract was washed with water and brine successively, and dried over anhydrous sodium sulfate. The solvent was removed under reduced pressure to give 2-chloro-4-methoxybenzaldehyde (0.54 g). The title compound was prepared in a similar manner to that described in Reference Example 45 using this material instead of 4-isobutyl-benzaldehyde.

Reference Example 50

4-[2-(Benzyloxy)ethyl]benzyl bromide

To a solution of 2-(4-bromophenyl)ethanol (1.0 g) in N,N-dimethylformamide (25 mL) was added 55% sodium hydride (0.26 g) under ice-cooling, and the mixture was stirred at the same temperature for 15 minutes. To this mixture was added benzyl bromide (0.77 mL) at the same temperature, and the mixture was stirred at the same temperature for 15 minutes, and stirred at room temperature for 30 minutes. The reaction mixture was poured into water, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane-n-hexane/ethyl acetate=20/1) to give 1-[2-(benzyloxy)ethyl]-4-bromobenzene (1.35 g). The title compound was prepared in a similar manner to that described in Step 2 of Reference Example 46 using this material instead of 1-bromo-2-fluoro-4-methoxybenzene.

Reference Example 51

4-[3-(Benzyloxy)phenyl]benzyl bromide

Step 1

A suspension of methyl 4-(4,4,5,5-tetramethyl-1,3,2-dioxabororan-2-yl)benzoate (1.0 g), 1-benzyloxy-3-iodobenzene (1.18 g), tetrakis(triphenylphosphine)palladium(0) (0.22 g) and potassium carbonate (1.58 g) in toluene (10 mL) was stirred at 100° C. under an argon atmosphere overnight. The reaction mixture was poured into water, and the resulting mixture was extracted with ethylacetate. The extract was washed with water and brine successively, and dried over anhydrous sodium sulfate. The solvent was removed under reduced pressure, and the residue was purified by column chromatography on silica gel (eluent: n-hexane/ethyl acetate=9/1-4/1) to give methyl 4-[3-(benzyloxy)phenyl] benzoate (1.2 g).

Step 2

To a solution of methyl 4-[3-(benzyloxy)phenyl]benzoate (1.2 g) in tetra hydrofuran (20 mL) was added lithium aluminum hydride (0.21 g) under ice-cooling, and the mixture was stirred at the same temperature for 10 minutes, and stirred at room temperature for 2 hours. To the reaction mixture was added ethyl acetate (10 mL), and the mixture was stirred at room temperature for 10 minutes. The reaction mixture was acidified by addition of 1 mol/L hydrochloric acid, and the resulting mixture was extracted with ethylacetate. The extract was washed with water and brine successively, and dried over anhydrous sodium sulfate. The solvent was removed under reduced pressure, and the residue was purified by column chromatography on silica gel (eluent: n-hexane/ethyl acetate=4/1-2/1) to give 4-[3-(benzyloxy)-phenyl]benzyl alcohol (0.32 g). This material was dissolved in ethyl acetate (4 mL). To the solution was added triethylamine (0.20 mL). To the mixture was added methanesulfonyl chloride (0.094 mL) under ice-cooling, and the mixture was stirred at the same temperature for 30 minutes. The insoluble material was removed by filtration. To the filtrate were added ethyl acetate (6 mL) and lithium bromide monohydrate (0.58 g), and the mixture was stirred at 55° C. for 2 hours. The reaction mixture was poured into water, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=20/1) to give the title compound (0.36 g).

Reference Example 52

Reference Example 52 was prepared in a similar manner to that described in Reference Example 51 using the corresponding starting material.

Reference Example 53

4-[2-(tert-Butoxycarbonylamino)ethoxy]benzyl bromide

To a solution of 4-hydroxybenzaldehyde (0.25 g), 2-(tert-butoxycarbonylamino)ethanol (0.33 g) and triphenylphosphine (0.59 g) in tetra hydrofuran (2 mL) was added diethyl azodicarboxylate (40% toluene solution, 1.34 mL), and the mixture was stirred at room temperature for 3 hours. The reaction mixture was directly purified by column chromatography on silica gel (eluent: n-hexane/ethyl acetate=6/1-3/1) to give 4-[2-(tert-butoxycarbonylamino)ethoxy]benzaldehyde (0.41 g). The title compound was prepared in a similar manner to that described in Reference Example 45 using this material instead of 4-isobutylbenzaldehyde.

Reference Example 54

4-[2-(tert-Butyldiphenylsilyloxy)ethoxy]benzyl bromide

To a solution of 4-(2-hydroxyethoxy)benzaldehyde (0.50 g) and imidazole (0.41 g) in N,N-dimethylformamide (6 mL) was added tert-butylchlorodiphenylsilane (0.94 mL), and the mixture was stirred at room temperature overnight. The reaction mixture was poured into water, and the resulting mixture was extracted with diethylether. The extract was washed with water and brine successively, and dried over anhydrous sodium sulfate. The solvent was removed under reduced pressure, and the residue was purified by column chromatography on silica gel (eluent: n-hexane/ethyl acetate=10/1) to give 4-[2-(tert-butyl-diphenylsilyloxy)ethoxy]benzaldehyde (1.21 g). The title compound was prepared in a similar manner to that described in Reference Example 45 using this material instead of 4-isobutylbenzaldehyde.

Reference Example 55

4-[2-(tert-Butyldiphenylsilyloxy)ethyl]benzyl bromide

To a solution of 2-(4-bromophenyl)ethanol (3.0 g) and imidazole (2.03 g) in N,N-dimethylformamide (30 mL) was added tert-butylchlorodiphenylsilane (4.66 mL), and the mixture was stirred at room temperature for 7 days. The reaction mixture was poured into water, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=10/1) to give 1-bromo-4-[2-(tert-butyldiphenylsilyloxy)ethyl]benzene (6.27 g). The title compound was prepared in a similar manner to that described in Step 2 of Reference Example 46 using this material instead of 1-bromo-2-fluoro-4-methoxybenzene.

Reference Example 56

4-[3-(tert-Butyldiphenylsilyloxy)propyl]benzyl bromide

To a solution of 3-(4-bromophenyl)propionic acid (1.0 g) in tetra hydrofuran (15 mL) was added borane tetra hydrofuran complex (1.0 mol/L tetra hydrofuran solution, 6.55 mL) under ice-cooling, and the mixture was stirred at room temperature for 2 hours. To the reaction mixture was added 20% aqueous potassium carbonate solution under ice-cooling, and the resulting mixture was extracted with ethylacetate. The extract was washed with brine, and dried over anhydrous sodium sulfate. The solvent was removed under reduced pressure to give 3-(4-bromophenyl)propanol (0.93 g). The title compound was prepared in a similar manner to that described in Reference Example 55 using this material instead of 2-(4-bromo-phenyl)ethanol.

Reference Example 57

4-[4-(tert-Butyldiphenylsilyloxy)butyl]benzyl bromide

A mixture of ethyl 4-iodobenzoate (1.38 g), 3-butenoic acid (1.08 g), palladium(II) acetate (0.11 g), tris(2-methylphenyl)phosphine (0.30 g), triethylamine (4 mL) and acetonitrile (5 mL) was stirred at 100° C. under an argon atmosphere overnight. The reaction mixture was diluted with ethylacetate. To the mixture was added 2 mol/L hydrochloric acid (20 mL), and the mixture was stirred at room temperature for 10 minutes. The insoluble material was removed by filtration, and the filtrate was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=2/1-1/1) to give ethyl 4-((1E)-3-carboxyprop-1-enyl)benzoate (0.60 g). This material was dissolved in ethyl acetate (9 mL). To the solution was added 10% palladium-carbon powder (0.60 g), and the mixture was stirred at room temperature under a hydrogen atmosphere for 3 hours. The insoluble material was removed by filtration, and the solvent was removed under reduced pressure. The residue was dissolved in tetra hydrofuran (10 mL). To the solution was added borane tetra hydrofuran complex (1.0 mol/L tetra hydrofuran solution, 3.56 mL) under ice-cooling, and the mixture was stirred at room temperature for 2 hours. To the reaction mixture was added 20% aqueous potassium carbonate solution under ice-cooling, and the resulting mixture was extracted with ethyl acetate. The extract was washed with brine, and dried over anhydrous sodium sulfate. The solvent was removed under reduced pressure. The residue was dissolved in N,N-dimethylformamide (5 mL). To the solution were added imidazole (0.32 g) and tert-butyl-chlorodiphenylsilane (0.68 mL), and the mixture was stirred at room temperature overnight. The reaction mixture was poured into water, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=10/1) to give ethyl 4-[4-(tert-butyldiphenylsilyloxy)-butyl]benzoate (0.95 g). The title compound was prepared in a similar manner to that described in Step 2 of Reference Example 51 using this material instead of methyl 4-[3-(benzyl-oxy)phenyl]benzoate.

Reference Example 58

4-[2-Benzyloxy-2-(methyl)propyl]benzyl bromide

To a suspension of 4-bromophenylacetic acid (2.15 g) and potassium carbonate (2.76 g) in N,N-dimethylformamide (15 mL) was added methyl iodide (0.94 mL), and the mixture was stirred at room temperature overnight. The reaction mixture was poured into water, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=10/1-5/1) to give methyl 4-bromophenylacetate (2.09 g). This material was dissolved in tetra hydrofuran (50 mL). To the solution was added methylmagnesium bromide (3.0 mol/L diethyl ether solution, 7.0 mL) under ice-cooling, and the mixture was stirred at the same temperature for 2 hours. To the reaction mixture was added 1 mol/L hydrochloric acid (30 mL), and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=4/1-2/1) to give 1-bromo-4-[2-hydroxy-2-(methyl)propyl]benzene (1.58 g) This material was dissolved in N,N-dimethylformamide (20 mL) To the solution was added 55% sodium hydride (0.32 g) under ice-cooling, and the mixture was stirred at the same temperature for 10 minutes. To this mixture were added benzyl bromide (0.98 mL) and tetra(n-butyl)ammonium iodide (0.51 g), and the mixture was stirred at room temperature overnight. The reaction mixture was poured into water, and the resulting mixture was extracted with diethyl ether. The extract was washed with brine, and dried over anhydrous sodium sulfate. The solvent was removed under reduced pressure, and the residue was purified by column chromatography on silica gel (eluent: n-hexane/ethyl acetate=99/1-95/5) to give 4-[2-benzyloxy-2-(methyl)propyl]-1-bromobenzene (1.2 g). The title compound was prepared in a similar manner to that described in Step 2 of Reference Example 46 using this material instead of 1-bromo-2-fluoro-4-methoxy-benzene.

Reference Example 59

Reference Example 59 was prepared in a similar manner to that described in Reference Example 58 using the corresponding starting material.

The structures and NMR spectrum data of the compounds of Reference Examples 45 to 59 are described in Table 4.

TABLE 4

| No. | Structure | $^1$H-NMR (CDCl$_3$) δ ppm: |
|---|---|---|
| Reference Example 45 | ![structure] | 0.9 (6H, d, J = 6.6 Hz), 1.75-1.9 (1H, m), 2.46 (2H, d, J = 7.1 Hz), 4.5 (2H, s), 7.05-7.15 (2H, m), 7.25-7.35 (2H, m) |

TABLE 4-continued

| No. | Structure | $^1$H-NMR (CDCl$_3$) δ ppm: |
|---|---|---|
| Reference Example 46 | 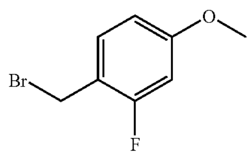 | 3.8 (3H, s), 4.51 (2H, s), 6.55-6.65 (1H, m), 6.65-6.7 (1H, m), 7.25-7.35 (1H, m) |
| Reference Example 47 | 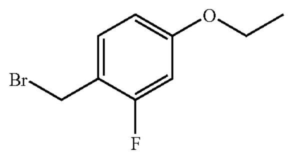 | 1.41 (3H, t, J = 7.1 Hz), 4.01 (2H, q, J = 7.1 Hz), 4.51 (2H, s), 6.55-6.7 (2H, m), 7.2-7.3 (1H, m) |
| Reference Example 48 | 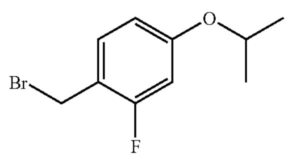 | 1.33 (6H, d, J = 6.0 Hz), 4.45-4.6 (3H, m), 6.55-6.7 (2H, m), 7.2-7.3 (1H, m) |
| Reference Example 49 | 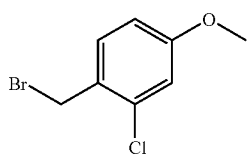 | 3.8 (3H, s), 4.59 (2H, s), 6.79 (1H, dd, J = 8.5, 2.5 Hz), 6.94 (1H, d, J = 2.5 Hz), 7.34 (1H, d, J = 8.5 Hz) |
| Reference Example 50 | 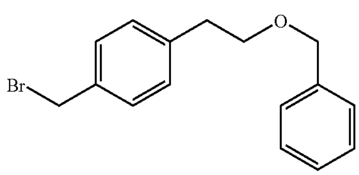 | 2.92 (2H, t, J = 7.0 Hz), 3.68 (2H, t, J = 7.0 Hz), 4.49 (2H, s), 4.52 (2H, s), 7.15-7.25 (2H, m), 7.25-7.4 (7H, m) |
| Reference Example 51 | 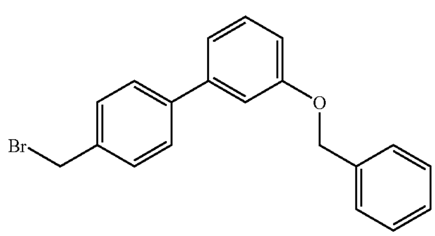 | 4.55 (2H, s), 5.12 (2H, s), 6.95-7.0 (1H, m), 7.15-7.25 (2H, m), 7.3-7.5 (8H, m), 7.5-7.6 (2H, m) |
| Reference Example 52 | 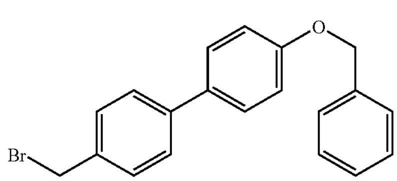 | 4.55 (2H, s), 5.12 (2H, s), 7.0-7.1 (2H, m), 7.3-7.55 (11H, m) |
| Reference Example 53 | 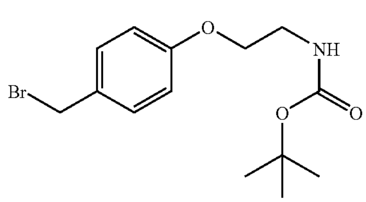 | 1.45 (9H, s), 3.45-3.6 (2H, m), 4.02 (2H, t, J = 5.0 Hz), 4.5 (2H, s), 4.9-5.05 (1H, m), 6.8-6.9 (2H, m), 7.25-7.35 (2H, m) |

TABLE 4-continued

| No. | Structure | $^1$H-NMR (CDCl$_3$) δ ppm: |
|---|---|---|
| Reference Example 54 | 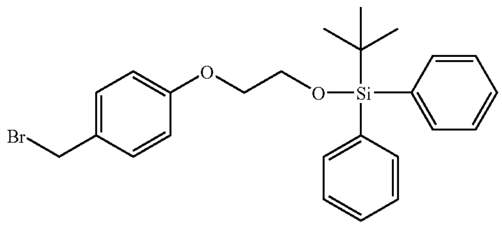 | 1.05 (9H, s), 3.98 (2H, t, J = 5.1 Hz), 4.07 (2H, t, J = 5.1 Hz), 4.5 (2H, s), 6.8-6.85 (2H, m), 7.25-7.35 (2H, m), 7.35-7.45 (6H, m), 7.65-7.75 (4H, m) |
| Reference Example 55 | 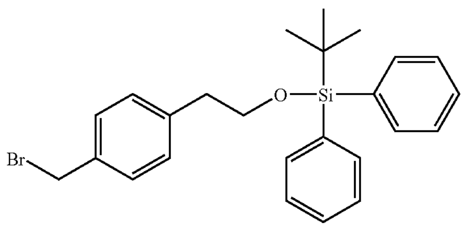 | 1.02 (9H, s), 2.83 (2H, t, J = 6.8 Hz), 3.83 (2H, t, J = 6.8 Hz), 4.48 (2H, s), 7.1-7.15 (2H, m), 7.25-7.3 (2H, m), 7.3-7.45 (6H, m), 7.55-7.6 (4H, m) |
| Reference Example 56 | 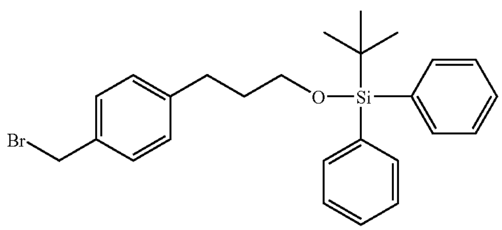 | 1.06 (9H, s), 1.8-1.9 (2H, m), 2.71 (2H, t, J = 7.7 Hz), 3.68 (2H, t, J = 6.1 Hz), 4.49 (2H, s), 7.1-7.15 (2H, m), 7.25-7.3 (2H, m), 7.3-7.45 (6H, m), 7.6-7.7 (4H, m) |
| Reference Example 57 | 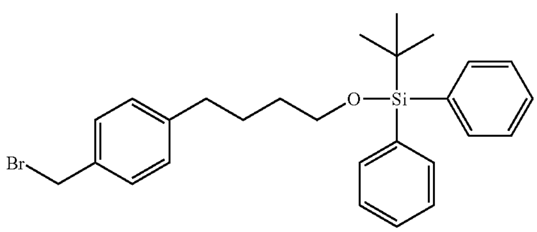 | 1.04 (9H, s), 1.55-1.65 (2H, m), 1.65-1.75 (2H, m), 2.59 (2H, t, J = 7.5 Hz), 3.67 (2H, t, J = 6.3 Hz), 4.49 (2H, s), 7.1-7.15 (2H, m), 7.25-7.45 (8H, m), 7.6-7.7 (4H, m) |
| Reference Example 58 | 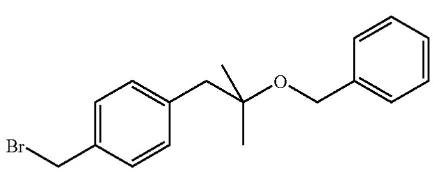 | 1.24 (6H, s) 2.87 (2H, s) 4.5 (2H, s) 4.52 (2H, s), 7.15-7.35 (9H, m) |
| Reference Example 59 | 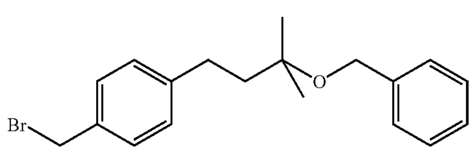 | 1.32 (6H, s), 1.8-1.9 (2H, m), 2.65-2.75 (2H, m), 4.46 (2H, s), 4.49 (2H, s), 7.1-7.2 (2H, m), 7.2-7.4 (7H, m) |

Reference Example 60

1-(2-Amino-2-methylpropionyl)-4-isopropylpiperazine

A suspension of 2-benzyloxycarbonylamino-2-methylpropionic acid (2.37 g), 1-isopropylpiperazine (1.54 g), 1-hydroxybenzotriazole (1.49 g), 1-ethyl-3-(3-dimethyl-aminopropyl)carbodiimide hydrochloride (2.88 g) and triethylamine (2.79 mL) in N,N-dimethylformamide (20 mL) was stirred at 50° C. overnight. The reaction mixture was poured into water, and the resulting mixture was extracted with ethyl acetate. The extract was washed with water, a saturated aqueous ammonium chloride solution, water, 0.5 mol/L aqueous sodium hydroxide solution, water and brine successively, and dried over anhydrous sodium sulfate. The solvent was removed under reduced pressure. The residue was washed with a mixed solvent of n-hexane and ethyl acetate (2/1), and dried under reduced pressure to give 1-(2-benzyloxycarbonylamino-2-methylpropionyl)-4-isopropylpiperazine (1.83 g). This material was dissolved in methanol (20 mL). To the solution was added 10% palladium-carbon powder (0.60 g), and the mixture was stirred at room temperature under a hydrogen atmosphere for 3 hours. The insoluble material was removed by filtration, and the solvent was removed under reduced pressure. The residue was crystallized from a mixed solvent of n-hexane and ethyl acetate, and the crystals were collected by filtration. The crystals were washed with n-hexane, and dried under reduced pressure to give the title compound (0.76 g).

$^1$H-NMR (CDCl$_3$) δ ppm:
1.05 (6H, d, J=6.3 Hz), 1.41 (6H, s), 2.45-2.55 (4H, m), 2.6-2.75 (1H, m), 3.7-3.9 (4H, m)

Example 1

1-(4-Ethylbenzyl)-3-(β-D-glucopyranosyl)-4-methyl-1H-indole

To a solution of 3-(2,3,4,6-tetra-O-benzyl-β-D-glucopyranosyl)-4-methyl-1H-indole (150 mg) in N,N-dimethylformamide (2 mL) was added 55% sodium hydride (12 mg) under ice-cooling, and the mixture was stirred at the same temperature for 15 minutes. To this mixture was added 4-ethylbenzyl bromide (55 mg) at the same temperature, and the mixture was stirred at the same temperature for 15 minutes, and stirred at room temperature for 1 hour. The reaction mixture was poured into 0.5 mol/L hydrochloric acid, and the resulting mixture was extracted with diethylether. The extract was washed with water and brine successively, and dried over anhydrous sodium sulfate. The solvent was removed under reduced pressure. The residue was washed with a mixed solvent of n-hexane and diethyl ether (10/1), and dried under reduced pressure to give 3-(2,3,4,6-tetra-O-benzyl-β-D-glucopyranosyl)-1-(4-ethyl-benzyl)-4-methyl-1H-indole (139 mg). This material (125 mg) was dissolved in a mixed solvent of methanol (2 mL) and tetra hydrofuran (2 mL). To the solution was added 10% palladium-carbon powder (50 mg), and the mixture was stirred at room temperature under a hydrogen atmosphere for 4 hours. The insoluble material was removed by filtration, and the solvent was removed under reduced pressure. The residue was purified by column chromatography on silica gel (eluent: dichloromethane/methanol=8/1) to give the title compound (58 mg).

Examples 2 to 9

Examples 2 to 9 were prepared in a similar manner to that described in Example 1 using the corresponding starting materials.

Example 10

1-(4-Ethoxybenzyl)-3-(β-D-glucopyranosyl)-5-methyl-1H-indole

To a mixture of 3-(β-D-glucopyranosyl)-1-(4-hydroxybenzyl)-5-methyl-1H-indole (50 mg), cesium carbonate (82 mg) and sodium iodide (19 mg) in acetonitrile (1 mL) was added ethyl bromide (41 mg), and the mixture was stirred at 40° C. for 3 days. The reaction mixture was poured into 15% aqueous sodium chloride solution, and the resulting mixture was extracted with ethyl acetate. The extract was dried over anhydrous sodium sulfate, and the solvent was removed under reduced pressure. The residue was purified by column chromatography on silica gel (eluent: dichloromethane/methanol=10/1) to give the title compound (21 mg).

Example 11

Example 11 was prepared in a similar manner to that described in Example 10 using the corresponding starting material.

The structures and NMR spectrum data of the compounds of Examples 1 to 11 are described in Table 5.

TABLE 5

| No. | Structure | $^1$H-NMR (CD$_3$OD) δ ppm: |
|---|---|---|
| Example 1 | 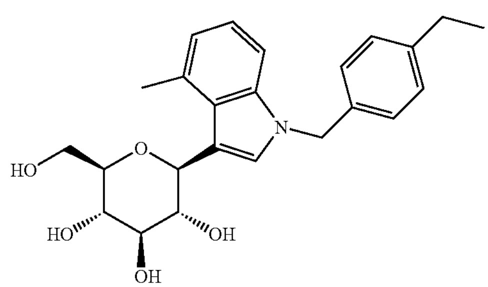 | 1.17 (3H, t, J = 7.5 Hz), 2.58 (2H, q, J = 7.5 Hz), 2.72 (3H, s), 3.35-3.55 (3H, m), 3.65 (1H, dd, J = 12.1, 6.0 Hz), 3.7-3.8 (1H, m), 3.87 (1H, dd, J = 12.1, 2.2 Hz), 4.8 (1H, d, J = 9.8 Hz), 5.27 (1H, d, J = 16.2 Hz), 5.33 (1H, d, J = 16.2 Hz), 6.8 (1H, d, J = 7.2 Hz), 6.9-7.0 (1H, m), 7.0-7.15 (5H, m), 7.37 (1H, s). |
| Example 2 | 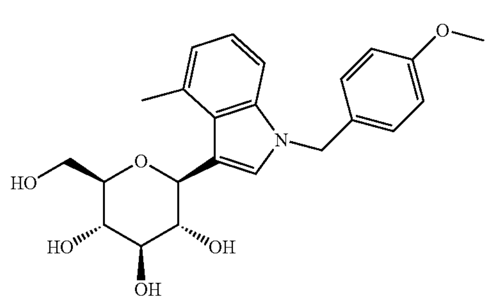 | 2.71 (3H, s), 3.35-3.45 (1H, m), 3.45-3.55 (2H, m), 3.65 (1H, dd, J = 12.2, 6.0 Hz), 3.7-3.8 (4H, m), 3.87 (1H, dd, J = 12.2, 2.4 Hz), 4.79 (1H, d, J = 9.8 Hz), 5.23 (1H, d, J = 15.4 Hz), 5.29 (1H, d, J = 15.4 Hz), 6.75-6.85 (3H, m), 6.95-7.0 (1H, m), 7.05-7.2 (3H, m), 7.36 (1H, s). |

TABLE 5-continued

| No. | Structure | $^1$H-NMR (CD$_3$OD) δ ppm: |
|---|---|---|
| Example 3 | 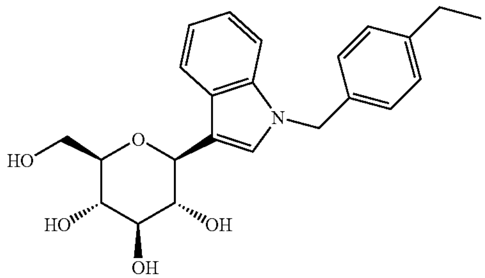 | 1.17 (3H, t, J = 7.6 Hz), 2.58 (2H, q, J = 7.6 Hz), 3.4-3.55 (3H, m), 3.65-3.8 (2H, m), 3.85-3.95 (1H, m), 4.49 (1H, d, J = 9.5 Hz), 5.31 (2H, s), 7.0-7.15 (6H, m), 7.25-7.35 (2H, m), 7.7-7.75 (1H, m). |
| Example 4 | 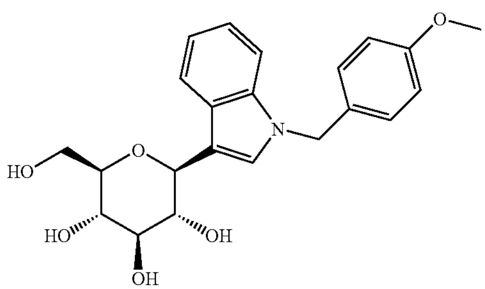 | 3.4-3.55 (3H, m), 3.65-3.8 (5H, m), 3.85-3.95 (1H, m), 4.48 (1H, d, J = 9.8 Hz), 5.28 (2H, s), 6.8-6.85 (2H, m), 7.0-7.2 (4H, m), 7.3-7.35 (2H, m), 7.7-7.75 (1H, m). |
| Example 5 | 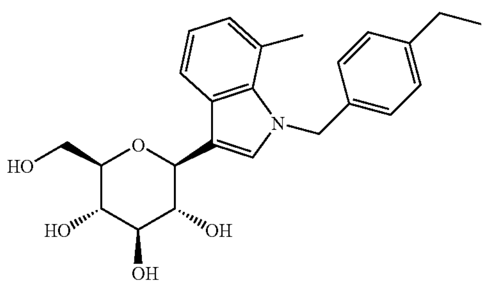 | 1.17 (3H, t, J = 7.6 Hz), 2.47 (3H, s), 2.58 (2H, q, J = 7.6 Hz), 3.4-3.55 (3H, m), 3.65-3.8 (2H, m), 3.85-3.95 (1H, m), 4.5 (1H, d, J = 9.7 Hz), 5.57 (2H, s), 6.75-6.95 (4H, m), 7.05-7.15 (2H, m), 7.26 (1H, s), 7.59 (1H, d, J = 8.0 Hz). |
| Example 6 | 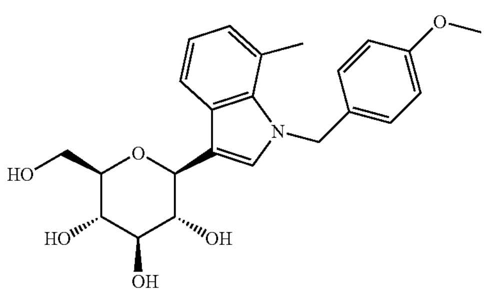 | 2.48 (3H, s), 3.4-3.55 (3H, m), 3.65-3.8 (5H, m), 3.9 (1H, dd, J = 11.9, 1.7 Hz), 4.49 (1H, d, J = 9.4 Hz), 5.54 (2H, s), 6.75-6.95 (6H, m), 7.25 (1H, s), 7.59 (1H, d, J = 7.8 Hz). |
| Example 7 | 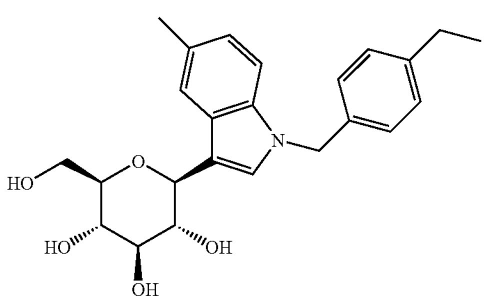 | 1.17 (3H, t, J = 7.6 Hz), 2.4 (3H, s), 2.58 (2H, q, J = 7.6 Hz), 3.4-3.55 (3H, m), 3.65-3.8 (2H, m), 3.85-3.95 (1H, m), 4.46 (1H, d, J = 9.6 Hz), 5.27 (2H, s), 6.9-7.0 (1H, m), 7.05-7.15 (4H, m), 7.19 (1H, d, J = 8.4 Hz), 7.28 (1H, s), 7.45-7.55 (1H, m). |

TABLE 5-continued

| No. | Structure | $^1$H-NMR (CD$_3$OD) δ ppm: |
|---|---|---|
| Example 8 | 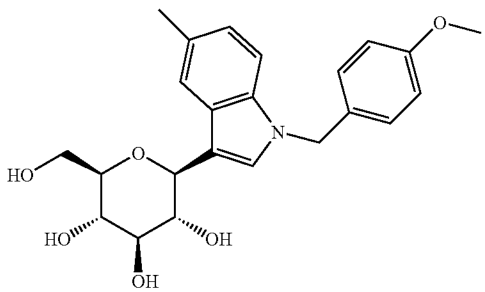 | 2.39 (3H, s), 3.4-3.55 (3H, m), 3.65-3.8 (5H, m), 3.89 (1H, dd, J = 11.9, 1.6 Hz), 4.45 (1H, d, J = 9.7 Hz), 5.23 (2H, s), 6.8-6.85 (2H, m), 6.9-7.0 (1H, m), 7.1-7.15 (2H, m), 7.19 (1H, d, J = 8.5 Hz), 7.27 (1H, s), 7.45-7.55 (1H, m). |
| Example 9 | 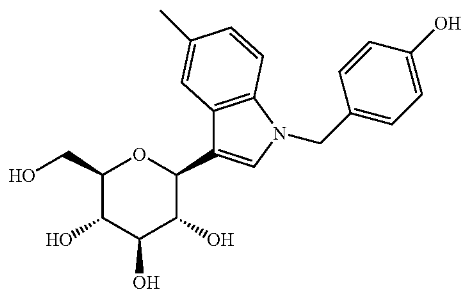 | 2.39 (3H, s), 3.4-3.55 (3H, m), 3.65-3.8 (2H, m), 3.85-3.95 (1H, m), 4.45 (1H, d, J = 9.6 Hz), 5.2 (2H, s), 6.65-6.75 (2H, m), 6.9-7.0 (1H, m), 7.0-7.1 (2H, m), 7.21 (1H, d, J = 8.8 Hz), 7.26 (1H, s), 7.45-7.55 (1H, m). |
| Example 10 | 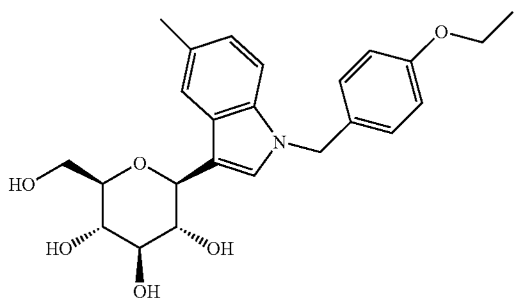 | 1.33 (3H, t, J = 6.9 Hz), 2.39 (3H, s), 3.4-3.55 (3H, m), 3.6-3.8 (2H, m), 3.85-3.95 (1H, m), 3.97 (2H, q, J = 6.9 Hz), 4.45 (1H, d, J = 9.9 Hz), 5.22 (2H, s), 6.75-6.85 (2H, m), 6.9-7.0 (1H, m), 7.05-7.15 (2H, m), 7.19 (1H, d, J = 8.5 Hz), 7.27 (1H, s), 7.45-7.55 (1H, m). |
| Example 11 | 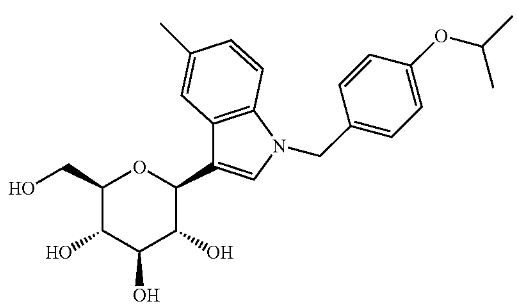 | 1.25 (6H, d, J = 5.9 Hz), 2.39 (3H, s), 3.4-3.55 (3H, m), 3.65-3.8 (2H, m), 3.85-3.95 (1H, m), 4.4-4.6 (2H, m), 5.22 (2H, s), 6.75-6.85 (2H, m), 6.9-7.0 (1H, m), 7.05-7.15 (2H, m), 7.2 (1H, d, J = 8.3 Hz), 7.27 (1H, s), 7.45-7.55 (1H, m). |

Examples 12 to 126

Examples 12 to 126 were prepared in a similar manner to that described in Example 1 using the corresponding starting materials. Ethyl acetate was used as a solvent in a hydrogenation step instead of tetra hydrofuran as occasion demands.

The structures and NMR spectrum data of the compounds of Examples 12 to 126 are described in Table 6.

TABLE 6

| No. | Structure | ¹H-NMR (CD₃OD) δ ppm: |
|---|---|---|
| Example 12 | 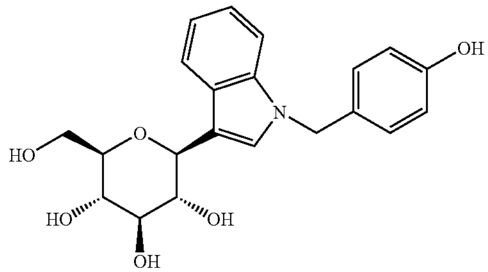 | 3.4-3.55 (3H, m), 3.65-3.8 (2H, m), 3.85-3.95 (1H, m), 4.48 (1H, d, J = 10.0 Hz), 5.24 (2H, s), 6.65-6.75 (2H, m), 6.95-7.15 (4H, m), 7.3-7.35 (2H, m), 7.65-7.75 (1H, m) |
| Example 13 | 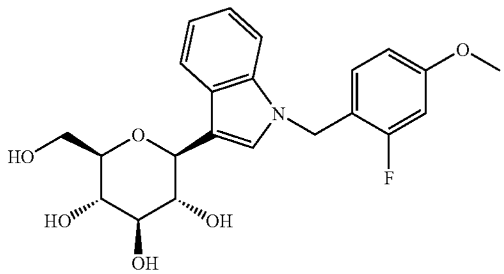 | 3.4-3.55 (3H, m), 3.65-3.8 (5H, m), 3.85-3.95 (1H, m), 4.48 (1H, d, J = 9.7 Hz), 5.31 (2H, s), 6.6-6.75 (2H, m), 7.0-7.1 (2H, m), 7.1-7.15 (1H, m), 7.33 (1H, s), 7.35-7.4 (1H, m), 7.7-7.75 (1H, m) |
| Example 14 | 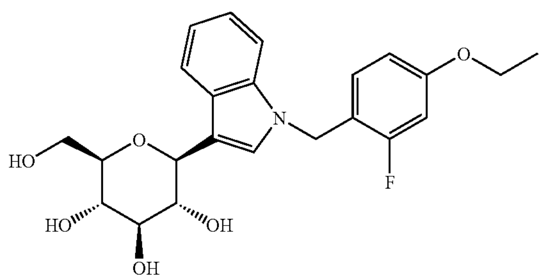 | 1.34 (3H, t, J = 7.0 Hz), 3.4-3.55 (3H, m), 3.65-3.8 (2H, m), 3.85-3.95 (1H, m), 3.99 (2H, q, J = 7.0 Hz), 4.47 (1H, d, J = 9.7 Hz), 5.31 (2H, s), 6.55-6.65 (1H, m), 6.65-6.75 (1H, m), 6.95-7.1 (2H, m), 7.1-7.15 (1H, m), 7.33 (1H, s), 7.35-7.4 (1H, m), 7.7-7.75 (1H, m) |
| Example 15 | 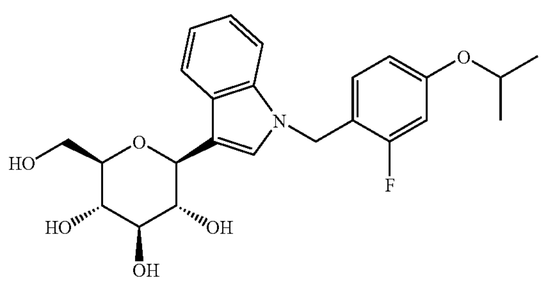 | 1.27 (6H, d, J = 6.1 Hz), 3.4-3.55 (3H, m), 3.65-3.8 (2H, m), 3.85-3.95 (1H, m), 4.48 (1H, d, J = 9.7 Hz), 4.5-4.6 (1H, m), 5.3 (2H, s), 6.55-6.7 (2H, m), 6.95-7.1 (2H, m), 7.1-7.2 (1H, m), 7.33 (1H, s), 7.35-7.4 (1H, m), 7.7-7.75 (1H, m) |
| Example 16 | 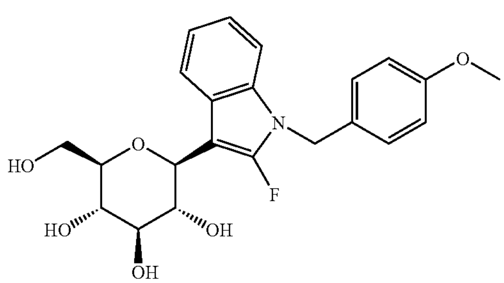 | 3.4-3.6 (3H, m), 3.6-4.0 (6H, m), 4.51 (1H, d, J = 9.8 Hz), 5.15-5.3 (2H, m), 6.75-6.9 (2H, m), 6.95-7.35 (5H, m), 7.6-7.7 (1H, m) |

TABLE 6-continued

| No. | Structure | $^1$H-NMR (CD$_3$OD) δ ppm: |
|---|---|---|
| Example 17 | 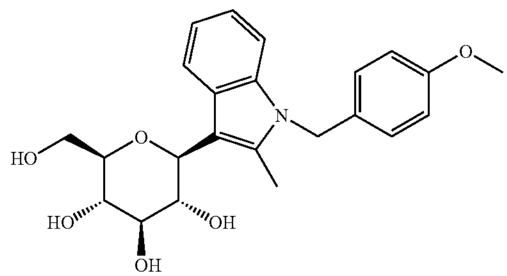 | 2.39 (3H, s), 3.4-3.55 (3H, m), 3.65-3.75 (4H, m), 3.8-3.95 (2H, m), 4.5 (1H, d, J = 9.2 Hz), 5.2-5.4 (2H, m), 6.75-6.85 (2H, m), 6.9-7.1 (4H, m), 7.2-7.3 (1H, m), 7.65-7.75 (1H, m) |
| Example 18 | 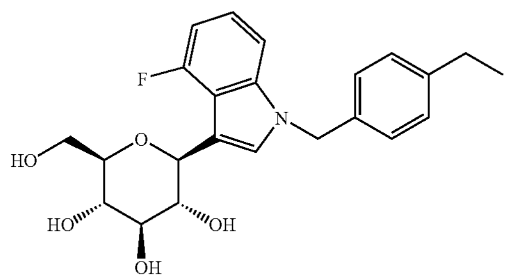 | 1.18 (3H, t, J = 7.7 Hz), 2.59 (2H, q, J = 7.7 Hz), 3.4-3.55 (3H, m), 3.6-3.7 (1H, m), 3.7-3.8 (1H, m), 3.8-3.9 (1H, m), 4.6 (1H, d, J = 9.2 Hz), 5.25-5.4 (2H, m), 6.65-6.75 (1H, m), 7.0-7.2 (6H, m), 7.37 (1H, s) |
| Example 19 | 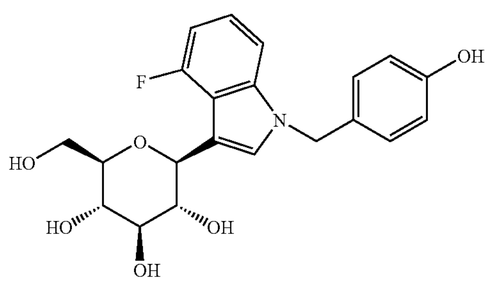 | 3.4-3.55 (3H, m), 3.6-3.7 (1H, m), 3.7-3.8 (1H, m), 3.8-3.9 (1H, m), 4.59 (1H, d, J = 9.9 Hz), 5.2-5.3 (2H, m), 6.65-6.75 (3H, m), 7.0-7.1 (3H, m), 7.1-7.2 (1H, m), 7.34 (1H, s) |
| Example 20 | 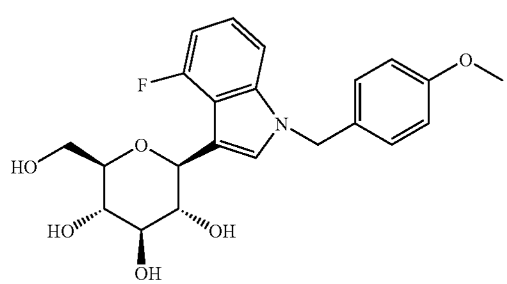 | 3.4-3.55 (3H, m), 3.6-3.7 (1H, m), 3.7-3.8 (4H, m), 3.8-3.9 (1H, m), 4.6 (1H, d, J = 10.0 Hz), 5.2-5.35 (2H, m), 6.65-6.75 (1H, m), 6.8-6.9 (2H, m), 7.0-7.1 (1H, m), 7.1-7.2 (3H, m), 7.36 (1H, s) |
| Example 21 | 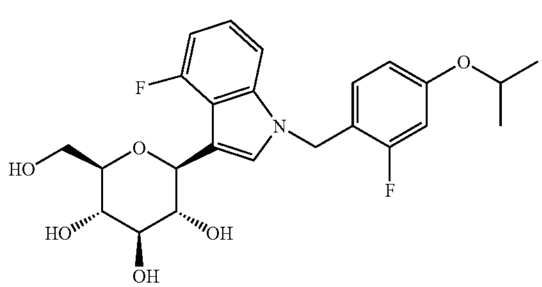 | 1.27 (6H, d, J = 6.1 Hz), 3.4-3.55 (3H, m), 3.6-3.7 (1H, m), 3.7-3.8 (1H, m), 3.8-3.9 (1H, m), 4.5-4.65 (2H, m), 5.25-5.4 (2H, m), 6.6-6.65 (1H, m), 6.65-6.8 (2H, m), 7.0-7.15 (2H, m), 7.2-7.25 (1H, m), 7.36 (1H, s) |

TABLE 6-continued

| No. | Structure | $^1$H-NMR (CD$_3$OD) δ ppm: |
|---|---|---|
| Example 22 | 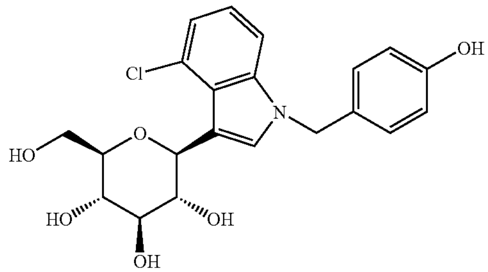 | 3.4-3.55 (3H, m), 3.65-3.95 (3H, m), 5.1 (1H, d, J = 9.8 Hz), 5.23 (1H, d, J = 15.3 Hz), 5.29 (1H, d, J = 15.3 Hz), 6.65-6.75 (2H, m), 7.0-7.1 (4H, m), 7.25-7.35 (1H, m), 7.46 (1H, s) |
| Example 23 | 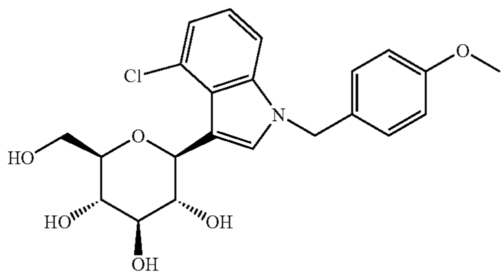 | 3.4-3.6 (3H, m), 3.65-3.9 (6H, m), 5.1 (1H, d, J = 9.7 Hz), 5.27 (1H, d, J = 15.4 Hz), 5.37 (1H, d, J = 15.4 Hz), 6.8-6.9 (2H, m), 7.0-7.1 (2H, m), 7.1-7.15 (2H, m), 7.25-7.35 (1H, m), 7.47 (1H, s) |
| Example 24 | 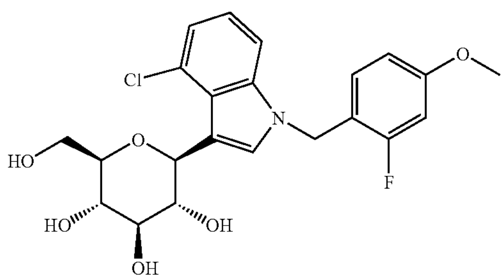 | 3.4-3.55 (3H, m), 3.65-3.9 (6H, m), 5.09 (1H, d, J = 9.7 Hz), 5.31 (1H, d, J = 15.9 Hz), 5.36 (1H, d, J = 15.9 Hz), 6.6-6.75 (2H, m), 6.95-7.15 (3H, m), 7.3-7.4 (1H, m), 7.47 (1H, s) |
| Example 25 | 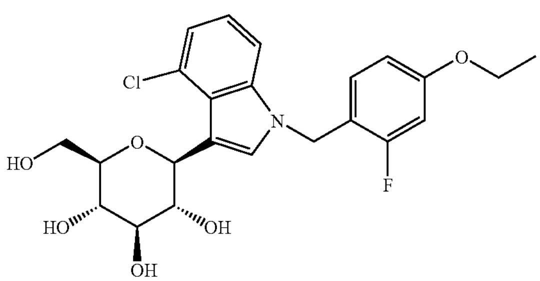 | 1.34 (3H, t, J = 7.1 Hz), 3.4-3.55 (3H, m), 3.65-3.9 (3H, m), 3.98 (2H, q, J = 7.1 Hz), 5.09 (1H, d, J = 9.8 Hz), 5.3 (1H, d, J = 15.7 Hz), 5.36 (1H, d, J = 15.7 Hz), 6.6-6.75 (2H, m), 6.95-7.15 (3H, m), 7.3-7.4 (1H, m), 7.47 (1H, s) |
| Example 26 | 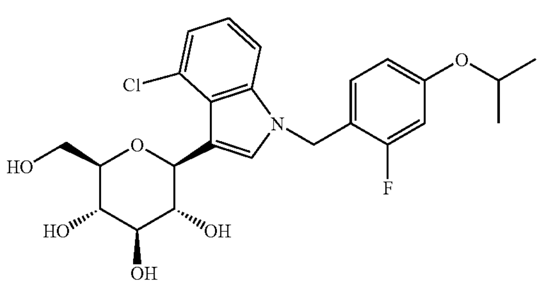 | 1.27 (6H, d, J = 6.1 Hz), 3.4-3.6 (3H, m), 3.65-3.9 (3H, m), 4.45-4.6 (1H, m), 5.09 (1H, d, J = 9.8 Hz), 5.3 (1H, d, J = 15.6 Hz), 5.35 (1H, d, J = 15.6 Hz), 6.55-6.75 (2H, m), 6.95-7.15 (3H, m), 7.3-7.4 (1H, m), 7.47 (1H, s) |

TABLE 6-continued
| No. | Structure | ¹H-NMR (CD₃OD) δ ppm: |
|---|---|---|
| Example 27 | 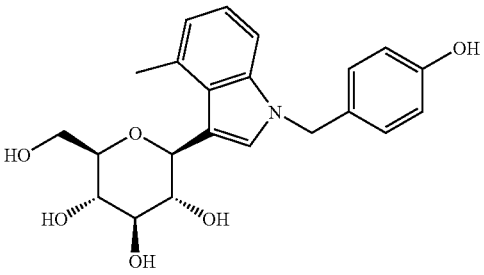 | 2.71 (3H, s), 3.35-3.55 (3H, m), 3.6-3.7 (1H, m), 3.7-3.8 (1H, m), 3.8-3.9 (1H, m), 4.79 (1H, d, J = 9.5 Hz), 5.2 (1H, d, J = 15.5 Hz), 5.26 (1H, d, J = 15.5 Hz), 6.65-6.7 (2H, m), 6.75-6.85 (1H, m), 6.95-7.05 (3H, m), 7.1-7.2 (1H, m), 7.35 (1H, s) |
| Example 28 | 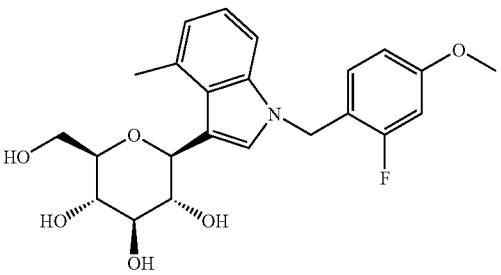 | 2.71 (3H, s), 3.35-3.55 (3H, m), 3.6-3.7 (1H, m), 3.7-3.8 (4H, m), 3.8-3.9 (1H, m), 4.78 (1H, d, J = 9.6 Hz), 5.28 (1H, d, J = 15.7 Hz), 5.33 (1H, d, J = 15.7 Hz), 6.55-6.65 (1H, m), 6.65-6.75 (1H, m), 6.75-6.85 (1H, m), 6.9-7.05 (2H, m), 7.15-7.25 (1H, m), 7.36 (1H, s) |
| Example 29 | 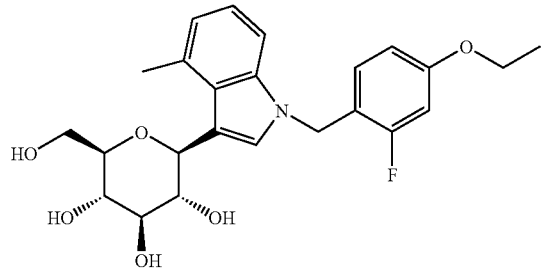 | 1.34 (3H, t, J = 7.1 Hz), 2.71 (3H, s), 3.35-3.55 (3H, m), 3.6-3.7 (1H, m), 3.7-3.8 (1H, m), 3.8-3.9 (1H, m), 3.98 (2H, q, J = 7.1 Hz), 4.78 (1H, d, J = 9.9 Hz), 5.28 (1H, d, J = 15.7 Hz), 5.33 (1H, d, J = 15.7 Hz), 6.55-6.75 (2H, m), 6.75-6.85 (1H, m), 6.9-7.05 (2H, m), 7.15-7.25 (1H, m), 7.36 (1H, s) |
| Example 30 | 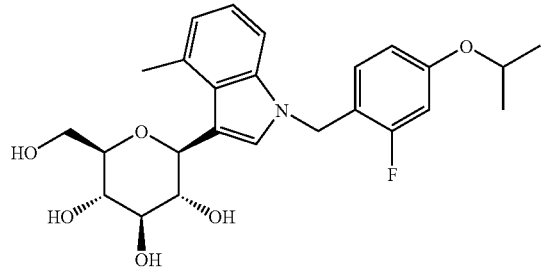 | 1.26 (6H, d, J = 6.1 Hz), 2.71 (3H, s), 3.35-3.55 (3H, m), 3.6-3.7 (1H, m), 3.7-3.8 (1H, m), 3.8-3.9 (1H, m), 4.45-4.6 (1H, m), 4.78 (1H, d, J = 9.8 Hz), 5.27 (1H, d, J = 15.7 Hz), 5.33 (1H, d, J = 15.7 Hz), 6.55-6.7 (2H, m), 6.75-6.85 (1H, m), 6.9-7.05 (2H, m), 7.15-7.25 (1H, m), 7.37 (1H, s) |
| Example 31 | 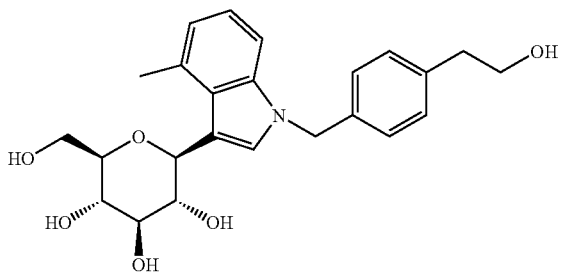 | 2.72 (3H, s), 2.76 (2H, t, J = 6.9 Hz), 3.35-3.6 (3H, m), 3.6-3.8 (4H, m), 3.8-3.95 (1H, m), 4.75-4.85 (1H, m), 5.28 (1H, d, J = 16.1 Hz), 5.33 (1H, d, J = 16.1 Hz), 6.75-6.85 (1H, m), 6.9-7.0 (1H, m), 7.05-7.2 (5H, m), 7.37 (1H, s) |

TABLE 6-continued

| No. | Structure | $^1$H-NMR (CD$_3$OD) δ ppm: |
|---|---|---|
| Example 32 | 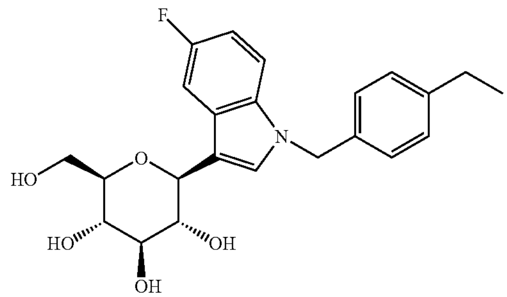 | 1.18 (3H, t, J = 7.6 Hz), 2.59 (2H, q, J = 7.6 Hz), 3.4-3.55 (3H, m), 3.6-3.75 (2H, m), 3.85-3.95 (1H, m), 4.45 (1H, d, J = 9.4 Hz), 5.3 (2H, s), 6.8-6.9 (1H, m), 7.05-7.15 (4H, m), 7.2-7.3 (1H, m), 7.35-7.45 (2H, m) |
| Example 33 | 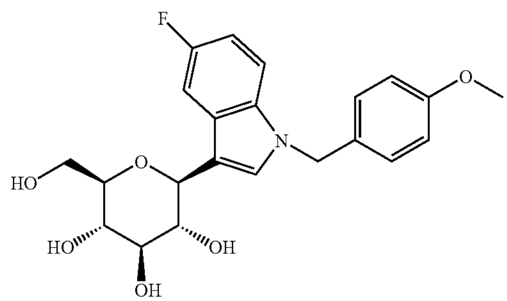 | 3.4-3.55 (3H, m), 3.6-3.8 (5H, m), 3.85-3.95 (1H, m), 4.44 (1H, d, J = 9.8 Hz), 5.27 (2H, s), 6.8-6.9 (3H, m), 7.1-7.2 (2H, m), 7.2-7.3 (1H, m), 7.35-7.4 (2H, m) |
| Example 34 | 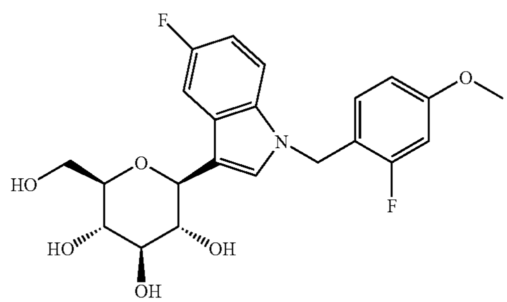 | 3.4-3.55 (3H, m), 3.6-3.8 (5H, m), 3.85-3.95 (1H, m), 4.43 (1H, d, J = 9.6 Hz), 5.3 (2H, s), 6.6-6.75 (2H, m), 6.85-6.95 (1H, m), 7.0-7.1 (1H, m), 7.3-7.4 (3H, m) |
| Example 35 | 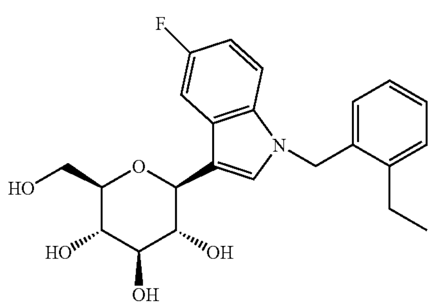 | 1.2 (3H, t, J = 7.6 Hz), 2.71 (2H, q, J = 7.6 Hz), 3.4-3.55 (3H, m), 3.6-3.75 (2H, m), 3.85-3.95 (1H, m), 4.43 (1H, d, J = 9.9 Hz), 5.3-5.45 (2H, m), 6.7-6.8 (1H, m), 6.85-6.95 (1H, m), 7.0-7.1 (1H, m), 7.15-7.3 (4H, m), 7.35-7.45 (1H, m) |
| Example 36 | 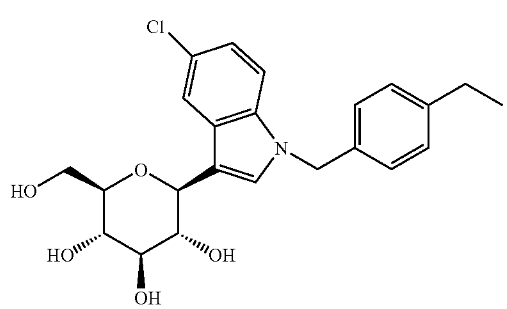 | 1.18 (3H, t, J = 7.7 Hz), 2.59 (2H, q, J = 7.7 Hz), 3.4-3.55 (3H, m), 3.6-3.75 (2H, m), 3.85-3.95 (1H, m), 4.45 (1H, d, J = 9.5 Hz), 5.3 (2H, s), 7.0-7.15 (5H, m), 7.28 (1H, d, J = 8.9 Hz), 7.39 (1H, s), 7.7 (1H, d, J = 2.0 Hz) |

TABLE 6-continued

| No. | Structure | $^1$H-NMR (CD$_3$OD) δ ppm: |
|---|---|---|
| Example 37 | 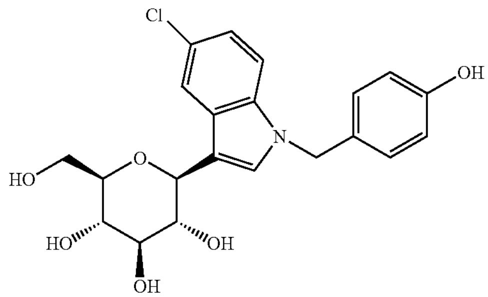 | 3.4-3.55 (3H, m), 3.6-3.75 (2H, m), 3.85-3.95 (1H, m), 4.44 (1H, d, J = 9.5 Hz), 5.23 (2H, s), 6.65-6.75 (2H, m), 7.0-7.1 (3H, m), 7.3 (1H, d, J = 8.8 Hz), 7.37 (1H, s), 7.69 (1H, d, J = 1.8 Hz) |
| Example 38 | 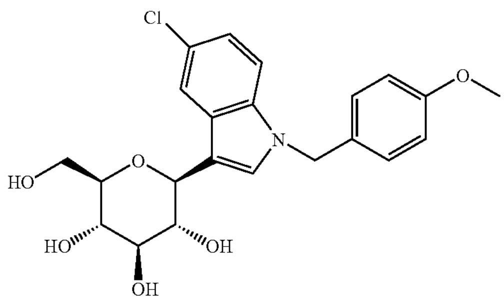 | 3.4-3.55 (3H, m), 3.6-3.8 (5H, m), 3.85-3.95 (1H, m), 4.44 (1H, d, J = 9.9 Hz), 5.27 (2H, s), 6.8-6.9 (2H, m), 7.06 (1H, dd, J = 8.7, 2.1 Hz), 7.1-7.2 (2H, m), 7.29 (1H, d, J = 8.7 Hz), 7.38 (1H, s), 7.7 (1H, d, J = 2.1 Hz) |
| Example 39 | 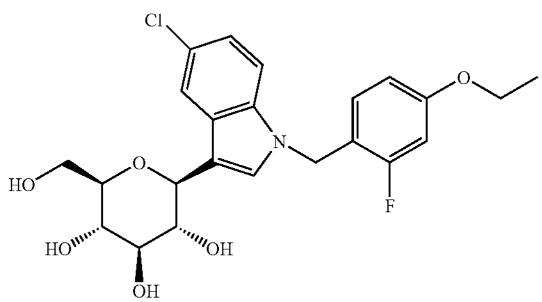 | 1.35 (3H, t, J = 7.0 Hz), 3.4-3.55 (3H, m), 3.6-3.75 (2H, m), 3.85-3.95 (1H, m), 3.99 (2H, q, J = 7.0 Hz), 4.43 (1H, d, J = 9.9 Hz), 5.3 (2H, s), 6.6-6.75 (2H, m), 7.0-7.15 (2H, m), 7.3-7.4 (2H, m), 7.69 (1H, d, J = 1.8 Hz) |
| Example 40 | 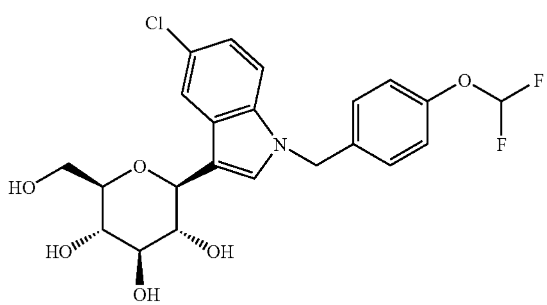 | 3.4-3.55 (3H, m), 3.65-3.75 (2H, m), 3.85-3.95 (1H, m), 4.45 (1H, d, J = 10.0 Hz), 5.3-5.4 (2H, m), 6.6-6.95 (1H, m), 7.0-7.1 (3H, m), 7.15-7.3 (3H, m), 7.41 (1H, s), 7.72 (1H, d, J = 2.1 Hz) |
| Example 41 | 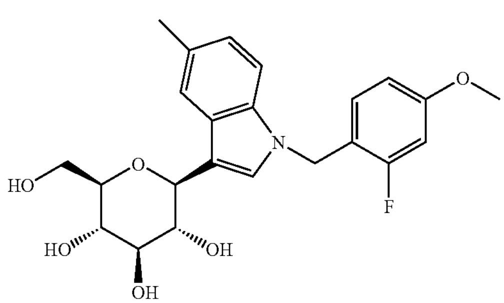 | 2.4 (3H, s), 3.4-3.55 (3H, m), 3.6-3.8 (5H, m), 3.85-3.95 (1H, m), 4.44 (1H, d, J = 9.6 Hz), 5.27 (2H, s), 6.6-6.65 (1H, m), 6.65-6.75 (1H, m), 6.9-7.05 (2H, m), 7.2-7.3 (2H, m), 7.45-7.55 (1H, m) |

TABLE 6-continued

| No. | Structure | $^1$H-NMR (CD$_3$OD) δ ppm: |
|---|---|---|
| Example 42 | 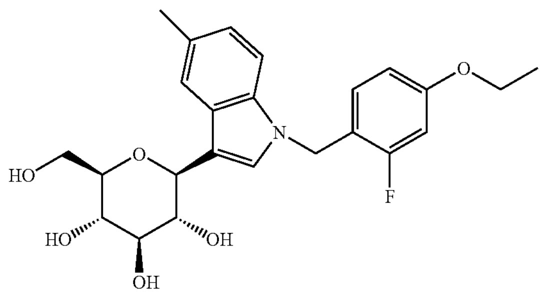 | 1.34 (3H, t, J = 7.1 Hz), 2.4 (3H, s), 3.4-3.55 (3H, m), 3.6-3.8 (2H, m), 3.85-3.95 (1H, m), 3.98 (2H, q, J = 7.1 Hz), 4.44 (1H, d, J = 9.9 Hz), 5.27 (2H, s), 6.55-6.7 (2H, m), 6.9-7.05 (2H, m), 7.2-7.3 (2H, m), 7.45-7.55 (1H, m) |
| Example 43 | 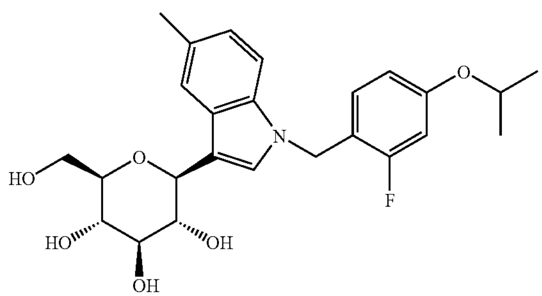 | 1.27 (6H, d, J = 6.1 Hz), 2.4 (3H, s), 3.4-3.55 (3H, m), 3.6-3.8 (2H, m), 3.85-3.95 (1H, m), 4.44 (1H, d, J = 9.3 Hz), 4.45-4.6 (1H, m), 5.26 (2H, s), 6.55-6.7 (2H, m), 6.9-7.05 (2H, m), 7.2-7.3 (2H, m), 7.45-7.55 (1H, m) |
| Example 44 | 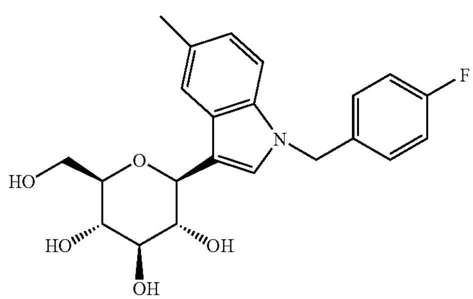 | 2.39 (3H, s), 3.4-3.55 (3H, m), 3.65-3.8 (2H, m), 3.85-3.95 (1H, m), 4.46 (1H, d, J = 9.3 Hz), 5.25-5.4 (2H, m), 6.9-7.05 (3H, m), 7.1-7.25 (3H, m), 7.3 (1H, s), 7.5-7.55 (1H, m) |
| Example 45 | 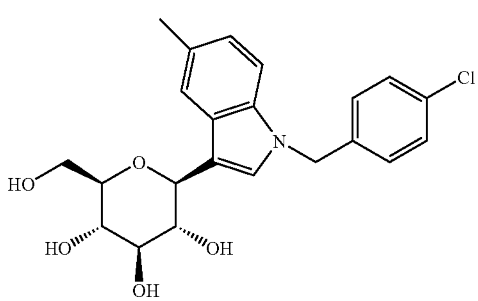 | 2.39 (3H, s), 3.4-3.55 (3H, m), 3.6-3.8 (2H, m), 3.85-3.95 (1H, m), 4.46 (1H, d, J = 9.6 Hz), 5.3 (2H, s), 6.9-7.0 (1H, m), 7.05-7.2 (3H, m), 7.2-7.3 (3H, m), 7.5-7.55 (1H, m) |
| Example 46 | 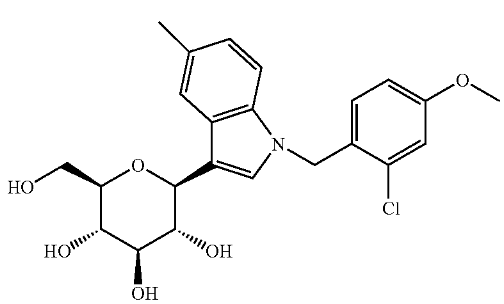 | 2.4 (3H, s), 3.4-3.55 (3H, m), 3.65-3.8 (5H, m), 3.85-3.95 (1H, m), 4.45 (1H, d, J = 9.4 Hz), 5.33 (2H, s), 6.65-6.8 (2H, m), 6.9-7.05 (2H, m), 7.1-7.2 (1H, m), 7.25 (1H, s), 7.5-7.55 (1H, m) |

TABLE 6-continued

| No. | Structure | $^1$H-NMR (CD$_3$OD) δ ppm: |
|---|---|---|
| Example 47 | 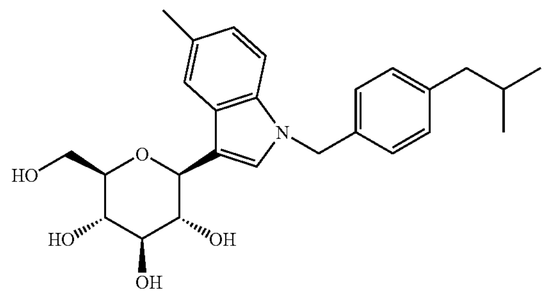 | 0.86 (6H, d, J = 6.6 Hz), 1.75-1.85 (1H, m), 2.35-2.45 (5H, m), 3.4-3.55 (3H, m), 3.65-3.8 (2H, m), 3.85-3.95 (1H, m), 4.46 (1H, d, J = 9.5 Hz), 5.28 (2H, s), 6.9-7.0 (1H, m), 7.0-7.15 (4H, m), 7.15-7.25 (1H, m), 7.29 (1H, s), 7.45-7.55 (1H, m) |
| Example 48 | 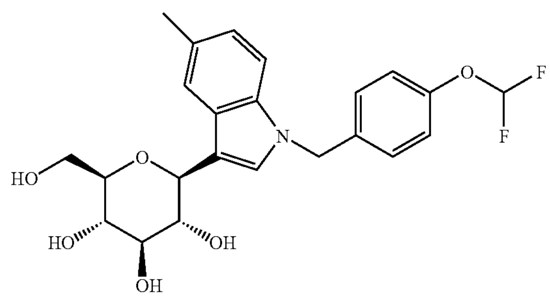 | 2.39 (3H, s), 3.4-3.55 (3H, m), 3.65-3.8 (2H, m), 3.85-3.95 (1H, m), 4.46 (1H, d, J = 9.5 Hz), 5.32 (2H, s), 6.55-6.9 (1H, m), 6.9-7.0 (1H, m), 7.0-7.1 (2H, m), 7.1-7.25 (3H, m), 7.31 (1H, s), 7.5-7.55 (1H, m) |
| Example 49 | 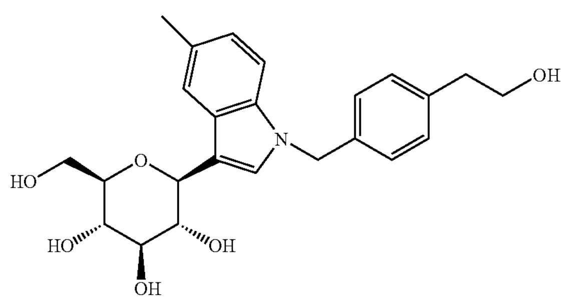 | 2.39 (3H, s), 2.76 (2H, t, J = 7.0 Hz), 3.4-3.55 (3H, m), 3.65-3.8 (4H, m), 3.85-3.95 (1H, m), 4.46 (1H, d, J = 9.6 Hz), 5.28 (2H, s), 6.9-6.95 (1H, m), 7.05-7.2 (5H, m), 7.29 (1H, s), 7.45-7.55 (1H, m) |
| Example 50 | 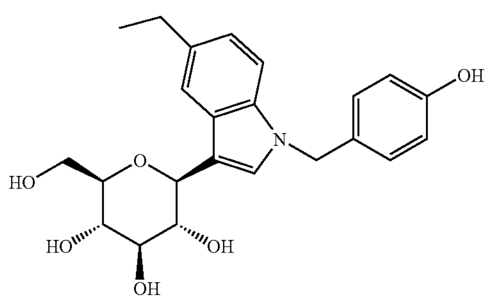 | 1.24 (3H, t, J = 7.6 Hz), 2.7 (2H, q, J = 7.6 Hz), 3.4-3.55 (3H, m), 3.65-3.8 (2H, m), 3.85-3.95 (1H, m), 4.46 (1H, d, J = 10.0 Hz), 5.2 (2H, s), 6.65-6.75 (2H, m), 6.95-7.1 (3H, m), 7.23 (1H, d, J = 8.7 Hz), 7.27 (1H, s), 7.5-7.55 (1H, m) |
| Example 51 | 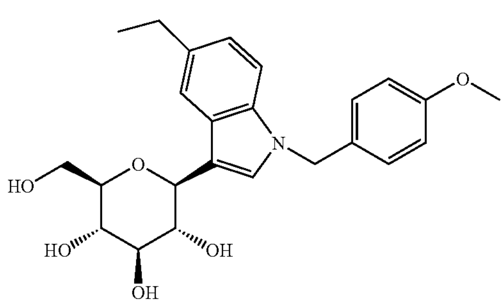 | 1.24 (3H, t, J = 7.6 Hz), 2.7 (2H, q, J = 7.6 Hz), 3.4-3.55 (3H, m), 3.65-3.8 (5H, m), 3.85-3.95 (1H, m), 4.46 (1H, d, J = 9.4 Hz), 5.24 (2H, s), 6.8-6.85 (2H, m), 6.95-7.0 (1H, m), 7.1-7.15 (2H, m), 7.22 (1H, d, J = 8.1 Hz), 7.28 (1H, s), 7.5-7.55 (1H, m) |

TABLE 6-continued

| No. | Structure | $^1$H-NMR (CD$_3$OD) δ ppm: |
|---|---|---|
| Example 52 | 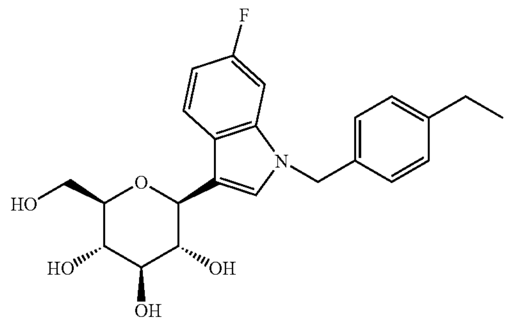 | 1.18 (3H, t, J = 7.6 Hz), 2.59 (2H, q, J = 7.6 Hz), 3.4-3.55 (3H, m), 3.6-3.75 (2H, m), 3.85-3.95 (1H, m), 4.45 (1H, d, J = 9.3 Hz), 5.26 (2H, s), 6.75-6.85 (1H, m), 6.95-7.05 (1H, m), 7.05-7.15 (4H, m), 7.33 (1H, s), 7.65-7.75 (1H, m) |
| Example 53 | 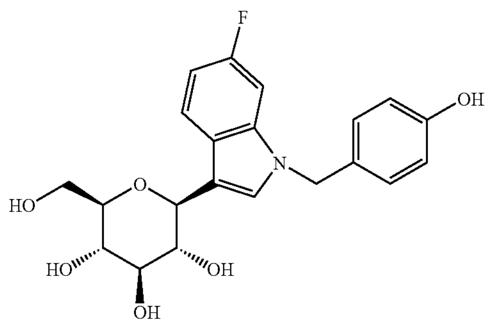 | 3.4-3.55 (3H, m), 3.6-3.75 (2H, m), 3.85-3.95 (1H, m), 4.44 (1H, d, J = 9.3 Hz), 5.19 (2H, s), 6.65-6.75 (2H, m), 6.75-6.85 (1H, m), 7.0-7.1 (3H, m), 7.31 (1H, s), 7.6-7.7 (1H, m) |
| Example 54 | 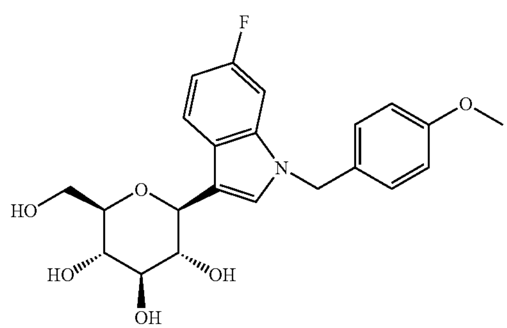 | 3.4-3.55 (3H, m), 3.6-3.8 (5H, m), 3.85-3.95 (1H, m), 4.45 (1H, d, J = 9.7 Hz), 5.23 (2H, s), 6.75-6.9 (3H, m), 7.0-7.1 (1H, m), 7.1-7.2 (2H, m), 7.32 (1H, s), 7.65-7.75 (1H, m) |
| Example 55 | 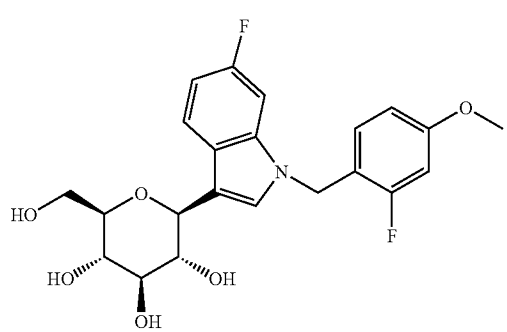 | 3.4-3.55 (3H, m), 3.6-3.75 (2H, m), 3.76 (3H, s), 3.85-3.95 (1H, m), 4.44 (1H, d, J = 9.6 Hz), 5.26 (2H, s), 6.6-6.75 (2H, m), 6.75-6.85 (1H, m), 7.0-7.15 (2H, m), 7.32 (1H, s), 7.65-7.7 (1H, m) |

TABLE 6-continued

| No. | Structure | $^1$H-NMR (CD$_3$OD) δ ppm: |
|---|---|---|
| Example 56 | 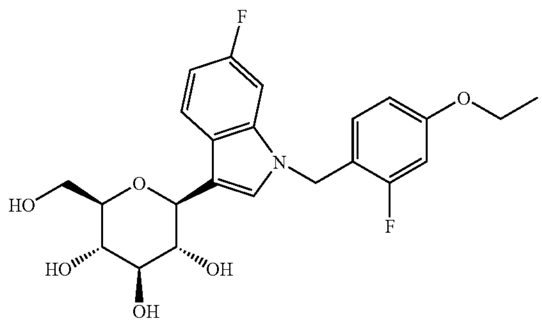 | 1.35 (3H, t, J = 7.0 Hz), 3.4-3.55 (3H, m), 3.6-3.75 (2H, m), 3.85-3.95 (1H, m), 3.99 (2H, q, J = 7.0 Hz), 4.43 (1H, d, J = 9.6 Hz), 5.25 (2H, s), 6.6-6.75 (2H, m), 6.75-6.85 (1H, m), 7.0-7.15 (2H, m), 7.32 (1H, s), 7.65-7.7 (1H, m) |
| Example 57 | 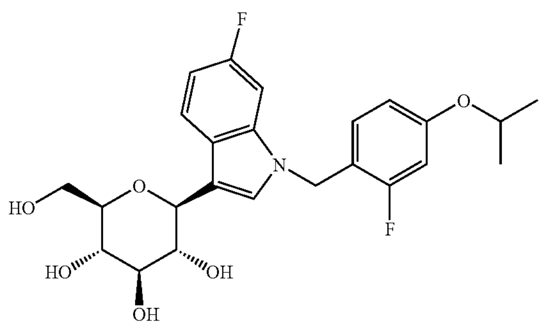 | 1.27 (6H, d, J = 6.3 Hz), 3.4-3.55 (3H, m), 3.6-3.75 (2H, m), 3.85-3.95 (1H, m), 4.44 (1H, d, J = 9.6 Hz), 4.5-4.6 (1H, m), 5.25 (2H, s), 6.6-6.75 (2H, m), 6.75-6.85 (1H, m), 7.0-7.15 (2H, m), 7.32 (1H, s), 7.65-7.7 (1H, m) |
| Example 58 | 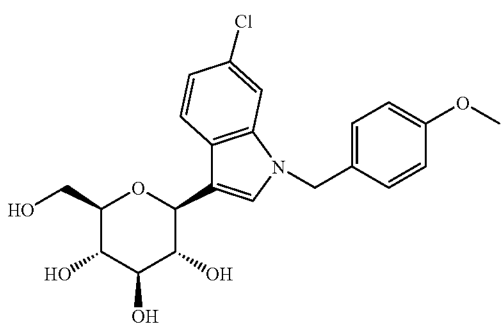 | 3.4-3.55 (3H, m), 3.65-3.8 (5H, m), 3.85-3.95 (1H, m), 4.45 (1H, d, J = 9.7 Hz), 5.24 (2H, s), 6.8-6.9 (2H, m), 7.0 (1H, dd, J = 8.5, 2.0 Hz), 7.1-7.2 (2H, m), 7.3-7.4 (2H, m), 7.68 (1H, d, J = 8.5 Hz) |
| Example 59 | 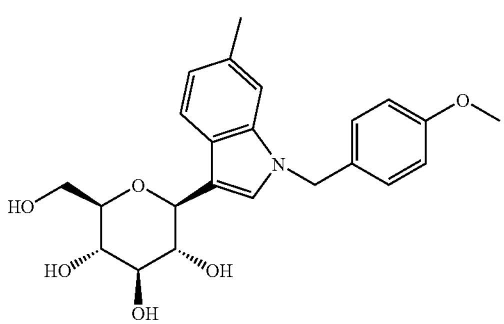 | 2.39 (3H, s), 3.4-3.55 (3H, m), 3.65-3.8 (5H, m), 3.85-3.95 (1H, m), 4.45 (1H, d, J = 9.7 Hz), 5.15-5.3 (2H, m), 6.8-6.9 (3H, m), 7.1-7.15 (3H, m), 7.23 (1H, s), 7.59 (1H, d, J = 7.9 Hz) |
| Example 60 | 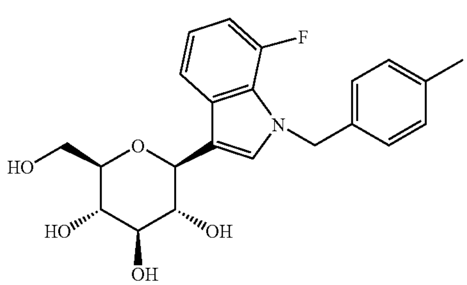 | 2.27 (3H, s), 3.4-3.55 (3H, m), 3.65-3.75 (2H, m), 3.85-3.95 (1H, m), 4.46 (1H, d, J = 9.8 Hz), 5.42 (2H, s), 6.75-6.85 (1H, m), 6.9-7.0 (1H, m), 7.0-7.1 (4H, m), 7.34 (1H, s), 7.45-7.55 (1H, m) |

TABLE 6-continued

| No. | Structure | $^1$H-NMR (CD$_3$OD) δ ppm: |
|---|---|---|
| Example 61 | 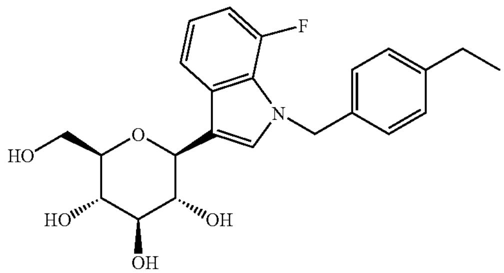 | 1.17 (3H, t, J = 7.7 Hz), 2.58 (2H, q, J = 7.7 Hz), 3.4-3.55 (3H, m), 3.6-3.75 (2H, m), 3.85-3.95 (1H, m), 4.46 (1H, d, J = 9.5 Hz), 5.43 (2H, s), 6.75-6.9 (1H, m), 6.9-7.0 (1H, m), 7.0-7.15 (4H, m), 7.34 (1H, s), 7.45-7.55 (1H, m) |
| Example 62 | 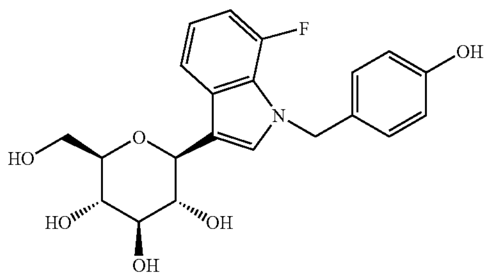 | 3.4-3.55 (3H, m), 3.6-3.75 (2H, m), 3.8-3.95 (1H, m), 4.45 (1H, d, J = 9.9 Hz), 5.36 (2H, s), 6.65-6.75 (2H, m), 6.75-6.85 (1H, m), 6.9-7.0 (1H, m), 7.0-7.1 (2H, m), 7.32 (1H, s), 7.45-7.55 (1H, m) |
| Example 63 | 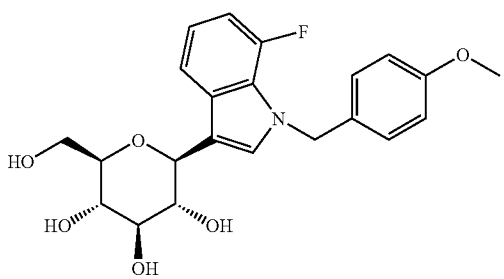 | 3.4-3.55 (3H, m), 3.6-3.75 (5H, m), 3.8-3.95 (1H, m), 4.45 (1H, d, J = 9.8 Hz), 5.39 (2H, s), 6.75-6.85 (3H, m), 6.9-7.0 (1H, m), 7.05-7.15 (2H, m), 7.33 (1H, s), 7.45-7.55 (1H, m) |
| Example 64 | 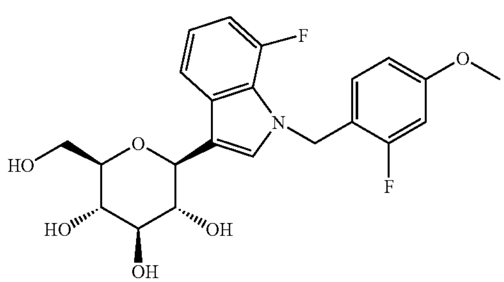 | 3.4-3.55 (3H, m), 3.6-3.8 (5H, m), 3.85-3.95 (1H, m), 4.45 (1H, d, J = 9.3 Hz), 5.46 (2H, s), 6.6-6.65 (1H, m), 6.65-6.75 (1H, m), 6.8-6.9 (1H, m), 6.9-7.0 (2H, m), 7.31 (1H, s), 7.45-7.55 (1H, m) |
| Example 65 | 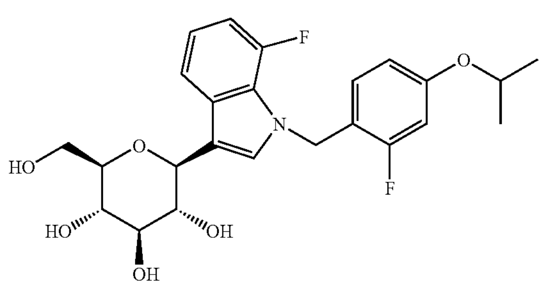 | 1.27 (6H, d, J = 5.9 Hz), 3.4-3.55 (3H, m), 3.6-3.75 (2H, m), 3.85-3.95 (1H, m), 4.4-4.6 (2H, m), 5.46 (2H, s), 6.55-6.7 (2H, m), 6.75-7.05 (3H, m), 7.31 (1H, s), 7.45-7.55 (1H, m) |

TABLE 6-continued

| No. | Structure | $^1$H-NMR (CD$_3$OD) δ ppm: |
|---|---|---|
| Example 66 | 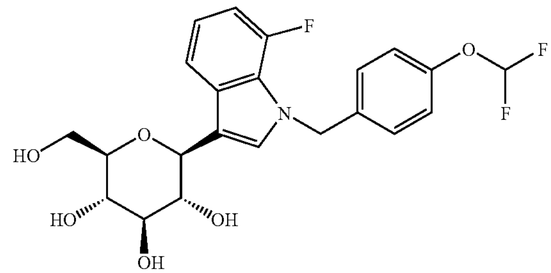 | 3.4-3.55 (3H, m), 3.6-3.75 (2H, m), 3.85-3.95 (1H, m), 4.47 (1H, d, J = 9.2 Hz), 5.47 (2H, s), 6.55-7.1 (5H, m), 7.15-7.25 (2H, m), 7.37 (1H, s), 7.45-7.55 (1H, m) |
| Example 67 | 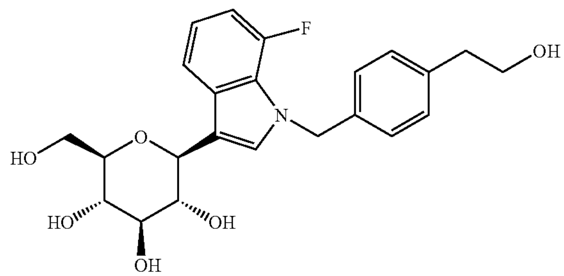 | 2.76 (2H, t, J = 6.9 Hz), 3.4-3.55 (3H, m), 3.65-3.75 (4H, m), 3.85-3.95 (1H, m), 4.46 (1H, d, J = 9.5 Hz), 5.4-5.5 (2H, m), 6.75-6.85 (1H, m), 6.9-7.0 (1H, m), 7.05-7.2 (4H, m), 7.34 (1H, s), 7.45-7.55 (1H, m) |
| Example 68 | 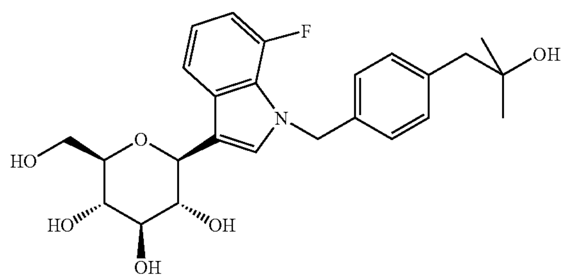 | 1.12 (6H, s), 2.69 (2H, s), 3.4-3.55 (3H, m), 3.65-3.75 (2H, m), 3.85-3.95 (1H, m), 4.47 (1H, d, J = 9.6 Hz), 5.4-5.55 (2H, m), 6.75-6.85 (1H, m), 6.9-7.0 (1H, m), 7.05-7.2 (4H, m), 7.36 (1H, s), 7.45-7.55 (1H, m) |
| Example 69 | 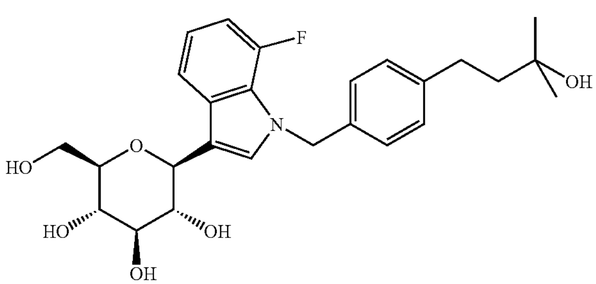 | 1.21 (6H, s), 1.65-1.75 (2H, m), 2.55-2.65 (2H, m), 3.4-3.55 (3H, m), 3.65-3.75 (2H, m), 3.85-3.95 (1H, m), 4.46 (1H, d, J = 9.5 Hz), 5.43 (2H, s), 6.75-6.85 (1H, m), 6.9-7.0 (1H, m), 7.05-7.15 (4H, m), 7.34 (1H, s), 7.45-7.55 (1H, m) |
| Example 70 | 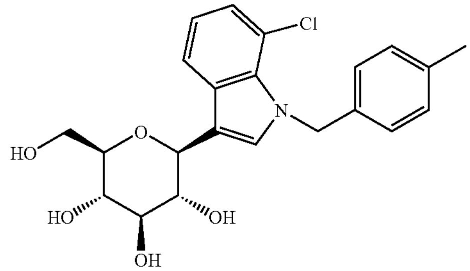 | 2.27 (3H, s), 3.4-3.55 (3H, m), 3.65-3.75 (2H, m), 3.85-3.95 (1H, m), 4.48 (1H, d, J = 9.5 Hz), 5.65-5.8 (2H, m), 6.85-7.1 (6H, m), 7.35 (1H, s), 7.65-7.75 (1H, m) |

TABLE 6-continued

| No. | Structure | $^1$H-NMR (CD$_3$OD) δ ppm: |
|---|---|---|
| Example 71 | 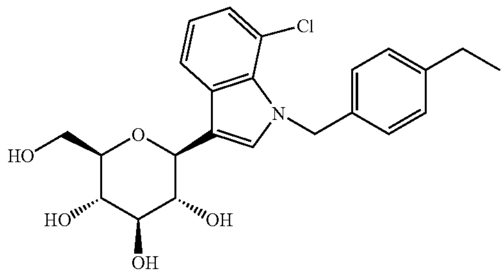 | 1.17 (3H, t, J = 7.6 Hz), 2.58 (2H, q, J = 7.6 Hz), 3.4-3.55 (3H, m), 3.6-3.75 (2H, m), 3.85-3.95 (1H, m), 4.49 (1H, d, J = 9.9 Hz), 5.65-5.8 (2H, m), 6.9-7.05 (3H, m), 7.05-7.15 (3H, m), 7.35 (1H, s), 7.65-7.75 (1H, m) |
| Example 72 | 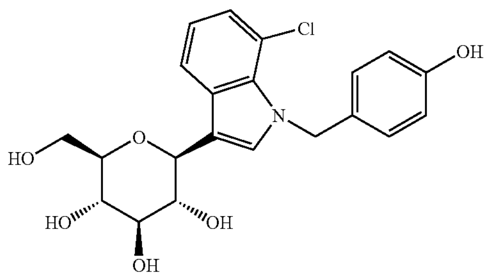 | 3.4-3.55 (3H, m), 3.6-3.75 (2H, m), 3.85-3.95 (1H, m), 4.47 (1H, d, J = 9.6 Hz), 5.6-5.75 (2H, m), 6.6-6.7 (2H, m), 6.85-7.05 (3H, m), 7.05-7.15 (1H, m), 7.33 (1H, s), 7.65-7.75 (1H, m) |
| Example 73 | 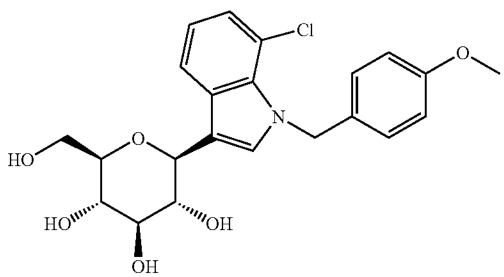 | 3.4-3.55 (3H, m), 3.6-3.75 (5H, m), 3.85-3.95 (1H, m), 4.48 (1H, d, J = 9.3 Hz), 5.6-5.75 (2H, m), 6.75-6.85 (2H, m), 6.95-7.05 (3H, m), 7.05-7.1 (1H, m), 7.35 (1H, s), 7.65-7.75 (1H, m) |
| Example 74 | 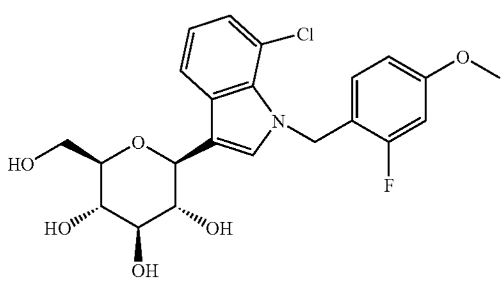 | 3.4-3.55 (3H, m), 3.65-3.8 (5H, m), 3.85-3.95 (1H, m), 4.48 (1H, d, J = 9.5 Hz), 5.65-5.8 (2H, m), 6.5-6.65 (2H, m), 6.65-6.75 (1H, m), 6.95-7.05 (1H, m), 7.05-7.15 (1H, m), 7.34 (1H, s), 7.65-7.75 (1H, m) |
| Example 75 | 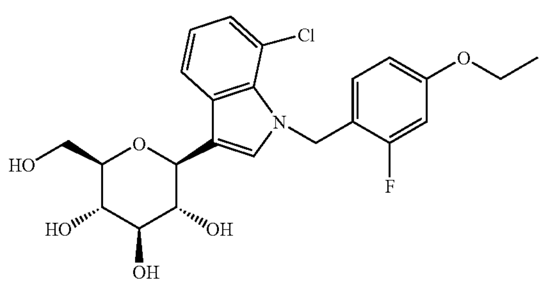 | 1.34 (3H, t, J = 7.0 Hz), 3.4-3.55 (3H, m), 3.6-3.75 (2H, m), 3.85-3.95 (1H, m), 3.98 (2H, q, J = 7.0 Hz), 4.48 (1H, d, J = 9.9 Hz), 5.74 (2H, s), 6.5-6.65 (2H, m), 6.65-6.75 (1H, m), 6.95-7.05 (1H, m), 7.05-7.15 (1H, m), 7.34 (1H, s), 7.65-7.75 (1H, m) |

TABLE 6-continued

| No. | Structure | $^1$H-NMR (CD$_3$OD) δ ppm: |
|---|---|---|
| Example 76 | 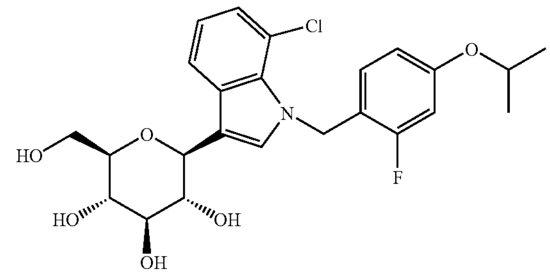 | 1.27 (6H, d, J = 6.1 Hz), 3.4-3.55 (3H, m), 3.6-3.75 (2H, m), 3.85-3.95 (1H, m), 4.45-4.6 (2H, m), 5.65-5.8 (2H, m), 6.5-6.7 (3H, m), 6.95-7.05 (1H, m), 7.05-7.15 (1H, m), 7.34 (1H, s), 7.65-7.75 (1H, m) |
| Example 77 | 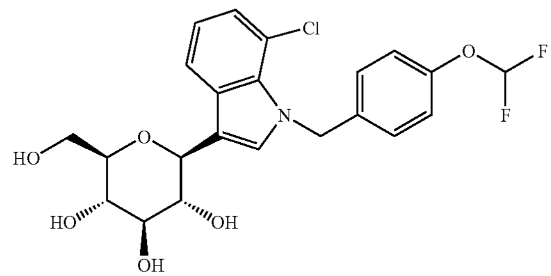 | 3.4-3.55 (3H, m), 3.65-3.75 (2H, m), 3.85-3.95 (1H, m), 4.49 (1H, d, J = 9.5 Hz), 5.7-5.85 (2H, m), 6.55-6.9 (1H, m), 6.95-7.15 (6H, m), 7.38 (1H, s), 7.65-7.75 (1H, m) |
| Example 78 | 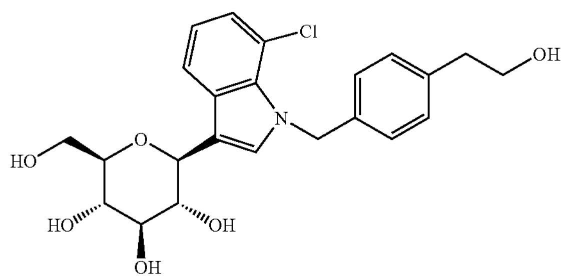 | 2.76 (2H, t, J = 6.9 Hz), 3.4-3.55 (3H, m), 3.65-3.75 (4H, m), 3.85-3.95 (1H, m), 4.48 (1H, d, J = 9.3 Hz), 5.65-5.8 (2H, m), 6.9-7.05 (3H, m), 7.05-7.15 (3H, m), 7.36 (1H, s), 7.65-7.75 (1H, m) |
| Example 79 | 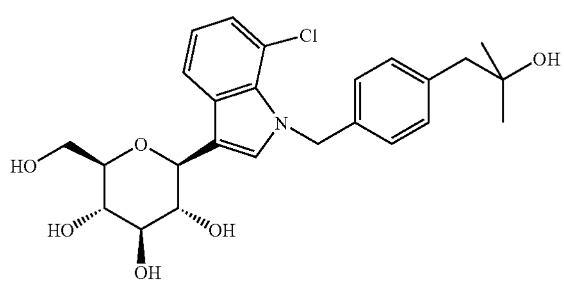 | 1.12 (6H, s), 2.69 (2H, s), 3.4-3.55 (3H, m), 3.65-3.75 (2H, m), 3.85-3.95 (1H, m), 4.49 (1H, d, J = 9.8 Hz), 5.65-5.8 (2H, m), 6.9-7.05 (3H, m), 7.05-7.15 (3H, m), 7.37 (1H, s), 7.65-7.75 (1H, m) |
| Example 80 | 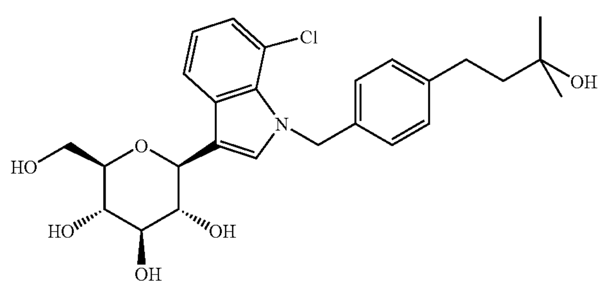 | 1.21 (6H, s), 1.65-1.75 (2H, m), 2.55-2.65 (2H, m), 3.4-3.55 (3H, m), 3.65-3.75 (2H, m), 3.85-3.95 (1H, m), 4.48 (1H, d, J = 9.7 Hz), 5.65-5.8 (2H, m), 6.9-7.05 (3H, m), 7.05-7.15 (3H, m), 7.35 (1H, s), 7.65-7.75 (1H, m) |

TABLE 6-continued

| No. | Structure | ¹H-NMR (CD₃OD) δ ppm: |
|---|---|---|
| Example 81 | 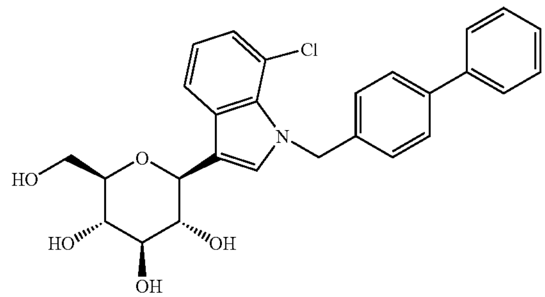 | 3.4-3.55 (3H, m), 3.65-3.75 (2H, m), 3.85-3.95 (1H, m), 4.51 (1H, d, J = 9.7 Hz), 5.75-5.9 (2H, m), 6.95-7.05 (1H, m), 7.05-7.15 (3H, m), 7.25-7.35 (1H, m), 7.35-7.45 (3H, m), 7.45-7.6 (4H, m), 7.65-7.75 (1H, m) |
| Example 82 | 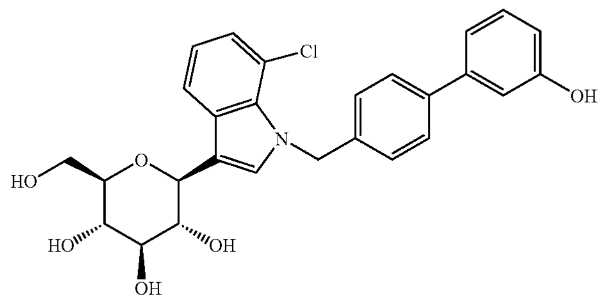 | 3.4-3.55 (3H, m), 3.65-3.75 (2H, m), 3.85-3.95 (1H, m), 4.51 (1H, d, J = 9.5 Hz), 5.75-5.9 (2H, m), 6.65-6.75 (1H, m), 6.9-7.25 (7H, m), 7.35-7.5 (3H, m), 7.65-7.75 (1H, m) |
| Example 83 | 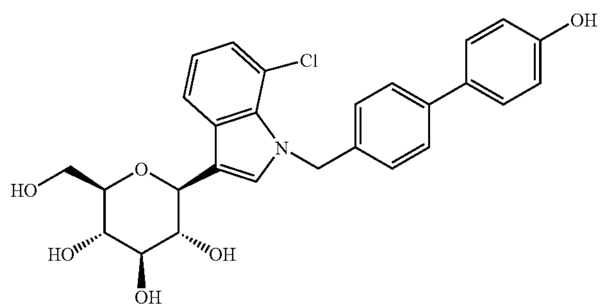 | 3.4-3.55 (3H, m), 3.65-3.75 (2H, m), 3.85-3.95 (1H, m), 4.5 (1H, d, J = 10.0 Hz), 5.75-5.85 (2H, m), 6.75-6.85 (2H, m), 6.95-7.05 (1H, m), 7.05-7.15 (3H, m), 7.35-7.5 (5H, m), 7.65-7.75 (1H, m) |
| Example 84 | 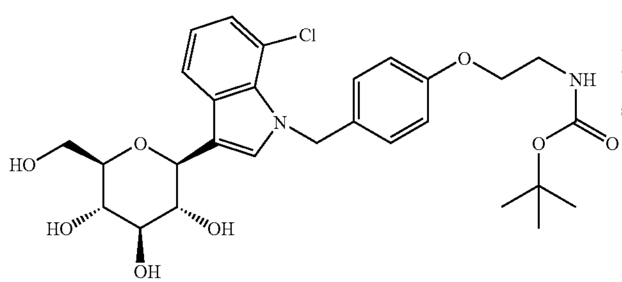 | 1.42 (9H, s), 3.35-3.4 (2H, m), 3.4-3.55 (3H, m), 3.65-3.75 (2H, m), 3.85-4.0 (3H, m), 4.48 (1H, d, J = 9.6 Hz), 5.65-5.75 (2H, m), 6.8-6.9 (2H, m), 6.95-7.05 (3H, m), 7.05-7.15 (1H, m), 7.35 (1H, s), 7.65-7.75 (1H, m) |
| Example 85 | 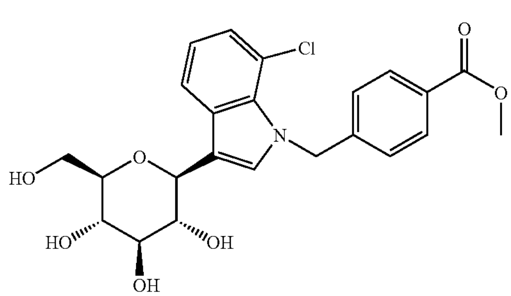 | 3.4-3.55 (3H, m), 3.65-3.75 (2H, m), 3.85-3.95 (4H, m), 4.51 (1H, d, J = 9.2 Hz), 5.8-5.9 (2H, m), 6.95-7.05 (1H, m), 7.05-7.15 (3H, m), 7.4 (1H, s), 7.7-7.75 (1H, m), 7.85-7.95 (2H, m) |

TABLE 6-continued
| No. | Structure | ¹H-NMR (CD₃OD) δ ppm: |
|---|---|---|
| Example 86 | 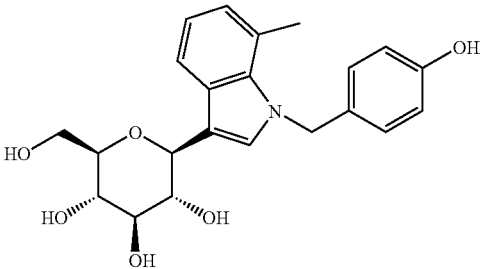 | 2.5 (3H, s), 3.4-3.55 (3H, m), 3.65-3.8 (2H, m), 3.85-3.95 (1H, m), 4.49 (1H, d, J = 10.1 Hz), 5.5 (2H, s), 6.6-6.7 (2H, m), 6.7-6.85 (3H, m), 6.85-6.95 (1H, m), 7.25 (1H, s), 7.55-7.6 (1H, m) |
| Example 87 | 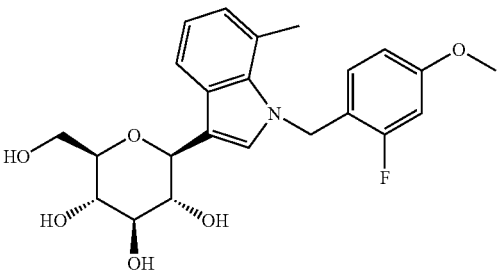 | 2.48 (3H, s), 3.4-3.55 (3H, m), 3.65-3.85 (5H, m), 3.85-3.95 (1H, m), 4.49 (1H, d, J = 9.6 Hz), 5.57 (2H, s), 6.35-6.45 (1H, m), 6.5-6.6 (1H, m), 6.7-6.75 (1H, m), 6.8-6.85 (1H, m), 6.85-6.95 (1H, m), 7.25 (1H, s), 7.55-7.65 (1H, m) |
| Example 88 | 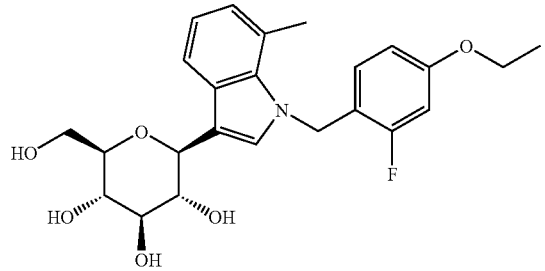 | 1.34 (3H, t, J = 7.1 Hz), 2.48 (3H, s), 3.4-3.55 (3H, m), 3.65-3.8 (2H, m), 3.85-3.95 (1H, m), 3.97 (2H, q, J = 7.1 Hz), 4.48 (1H, d, J = 9.5 Hz), 5.56 (2H, s), 6.35-6.45 (1H, m), 6.45-6.55 (1H, m), 6.65-6.75 (1H, m), 6.8-6.85 (1H, m), 6.9-6.95 (1H, m), 7.25 (1H, s), 7.55-7.65 (1H, m) |
| Example 89 | 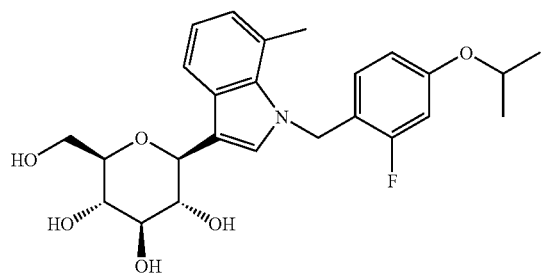 | 1.26 (6H, d, J = 6.1 Hz), 2.49 (3H, s), 3.4-3.55 (3H, m), 3.65-3.8 (2H, m), 3.85-3.95 (1H, m), 4.45-4.6 (2H, m), 5.56 (2H, s), 6.35-6.45 (1H, m), 6.45-6.55 (1H, m), 6.65-6.75 (1H, m), 6.8-6.85 (1H, m), 6.9-6.95 (1H, m), 7.25 (1H, s), 7.55-7.65 (1H, m) |
| Example 90 | 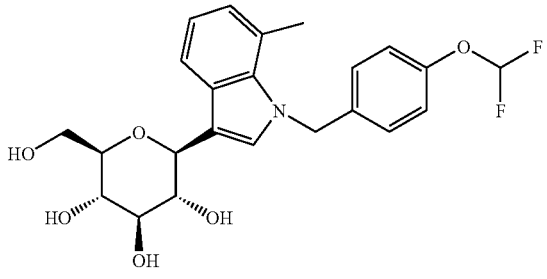 | 2.45 (3H, s), 3.4-3.55 (3H, m), 3.65-3.8 (2H, m), 3.85-3.95 (1H, m), 4.5 (1H, d, J = 9.5 Hz), 5.59 (2H, s), 6.55-7.0 (5H, m), 7.0-7.05 (2H, m), 7.27 (1H, s), 7.55-7.65 (1H, m) |

TABLE 6-continued

| No. | Structure | $^1$H-NMR (CD$_3$OD) δ ppm: |
|---|---|---|
| Example 91 | 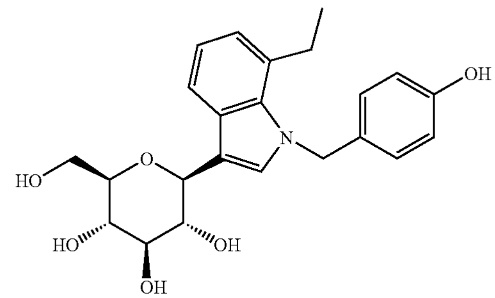 | 1.17 (3H, t, J = 7.4 Hz), 2.84 (2H, q, J = 7.4 Hz), 3.4-3.55 (3H, m), 3.65-3.8 (2H, m), 3.85-3.95 (1H, m), 4.5 (1H, d, J = 9.8 Hz), 5.45 (2H, s), 6.6-6.7 (2H, m), 6.7-6.8 (2H, m), 6.85-7.0 (2H, m), 7.25 (1H, s), 7.55-7.65 (1H, m) |
| Example 92 | 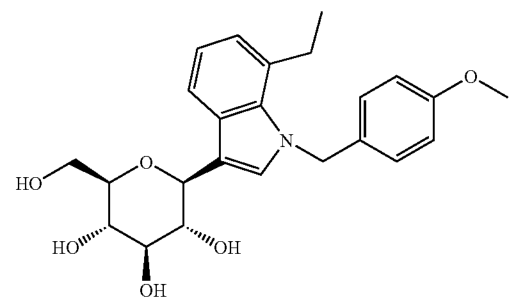 | 1.16 (3H, t, J = 7.5 Hz), 2.82 (2H, q, J = 7.5 Hz), 3.4-3.55 (3H, m), 3.65-3.8 (5H, m), 3.85-3.95 (1H, m), 4.5 (1H, d, J = 10.0 Hz), 5.48 (2H, s), 6.75-7.0 (6H, m), 7.26 (1H, s), 7.55-7.65 (1H, m) |
| Example 93 | 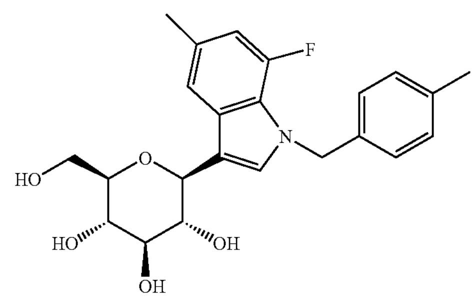 | 2.27 (3H, s), 2.38 (3H, s), 3.4-3.55 (3H, m), 3.65-3.75 (2H, m), 3.85-3.95 (1H, m), 4.43 (1H, d, J = 9.8 Hz), 5.3-5.45 (2H, m), 6.6-6.7 (1H, m), 7.0-7.15 (4H, m), 7.25-7.35 (2H, m) |
| Example 94 | 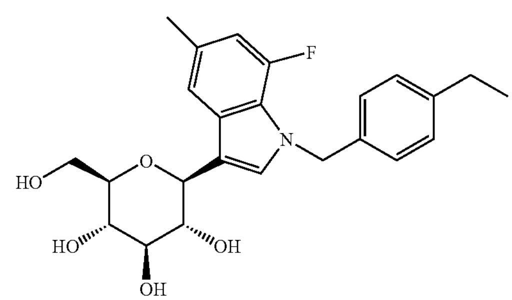 | 1.17 (3H, t, J = 7.6 Hz), 2.38 (3H, s), 2.58 (2H, q, J = 7.6 Hz), 3.4-3.55 (3H, m), 3.6-3.75 (2H, m), 3.85-3.95 (1H, m), 4.43 (1H, d, J = 9.6 Hz), 5.39 (2H, s), 6.6-6.7 (1H, m), 7.0-7.15 (4H, m), 7.25-7.35 (2H, m) |
| Example 95 | 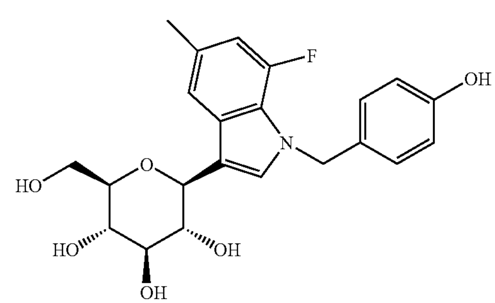 | 2.38 (3H, s), 3.4-3.55 (3H, m), 3.6-3.75 (2H, m), 3.8-3.95 (1H, m), 4.42 (1H, d, J = 9.8 Hz), 5.31 (2H, s), 6.6-6.75 (3H, m), 6.95-7.1 (2H, m), 7.2-7.35 (2H, m) |

TABLE 6-continued

| No. | Structure | $^1$H-NMR (CD$_3$OD) δ ppm: |
|---|---|---|
| Example 96 | 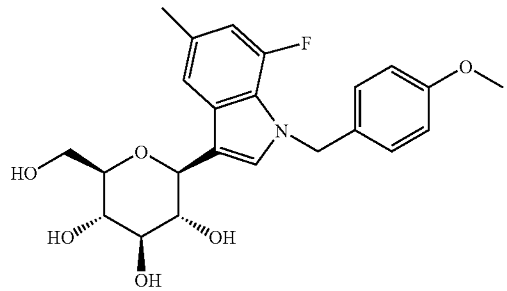 | 2.38 (3H, s), 3.4-3.55 (3H, m), 3.65-3.75 (5H, m), 3.85-3.95 (1H, m), 4.42 (1H, d, J = 9.9 Hz), 5.35 (2H, s), 6.6-6.7 (1H, m), 6.75-6.85 (2H, m), 7.05-7.15 (2H, m), 7.25-7.35 (2H, m) |
| Example 97 | 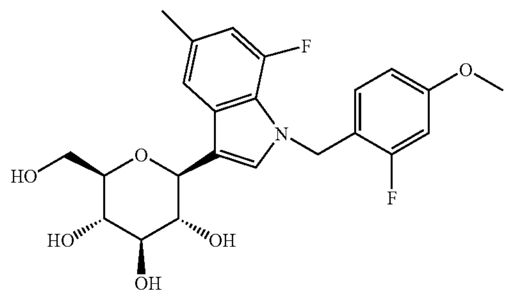 | 2.38 (3H, s), 3.4-3.55 (3H, m), 3.65-3.8 (5H, m), 3.85-3.95 (1H, m), 4.42 (1H, d, J = 9.6 Hz), 5.42 (2H, s), 6.55-6.65 (1H, m), 6.65-6.75 (2H, m), 6.9-7.0 (1H, m), 7.2-7.35 (2H, m) |
| Example 98 | 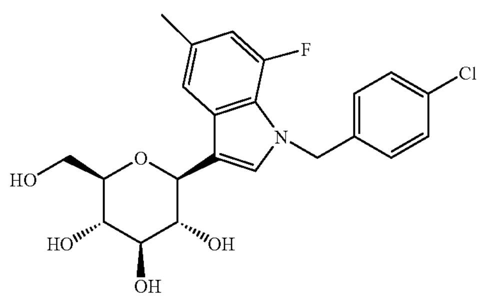 | 2.37 (3H, s), 3.4-3.55 (3H, m), 3.6-3.75 (2H, m), 3.85-3.95 (1H, m), 4.44 (1H, d, J = 9.6 Hz), 5.41 (2H, s), 6.6-6.7 (1H, m), 7.05-7.15 (2H, m), 7.2-7.35 (4H, m) |
| Example 99 | 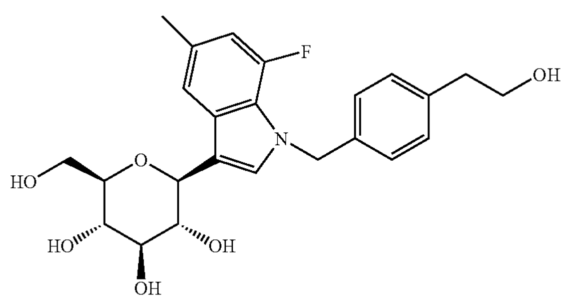 | 2.37 (3H, s), 2.75 (2H, t, J = 6.9 Hz), 3.4-3.55 (3H, m), 3.6-3.75 (4H, m), 3.85-3.95 (1H, m), 4.43 (1H, d, J = 9.7 Hz), 5.3-5.45 (2H, m), 6.6-6.7 (1H, m), 7.0-7.2 (4H, m), 7.25-7.35 (2H, m) |
| Example 100 | 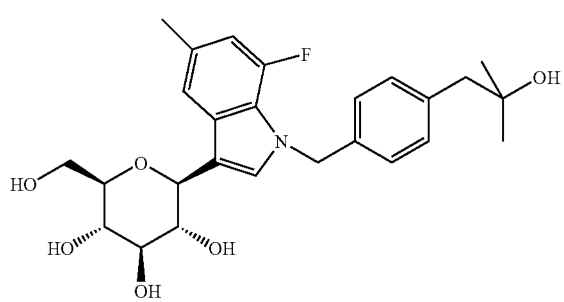 | 1.12 (6H, s), 2.38 (3H, s), 2.69 (2H, s), 3.4-3.55 (3H, m), 3.65-3.75 (2H, m), 3.85-3.95 (1H, m), 4.43 (1H, d, J = 9.7 Hz), 5.35-5.5 (2H, m), 6.6-6.7 (1H, m), 7.05-7.2 (4H, m), 7.25-7.35 (2H, m) |

TABLE 6-continued

| No. | Structure | $^1$H-NMR (CD$_3$OD) δ ppm: |
|---|---|---|
| Example 101 | 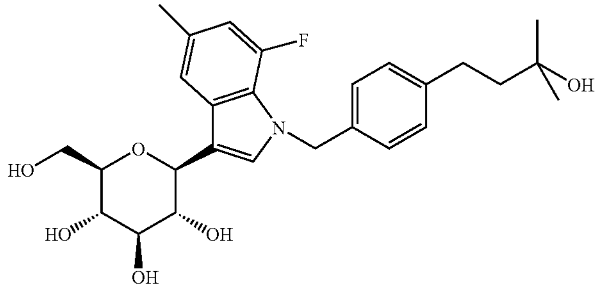 | 1.21 (6H, s), 1.65-1.75 (2H, m), 2.38 (3H, s), 2.55-2.65 (2H, m), 3.4-3.55 (3H, m), 3.65-3.75 (2H, m), 3.85-3.95 (1H, m), 4.43 (1H, d, J = 9.9 Hz), 5.39 (2H, s), 6.6-6.7 (1H, m), 7.0-7.15 (4H, m), 7.25-7.35 (2H, m) |
| Example 102 | 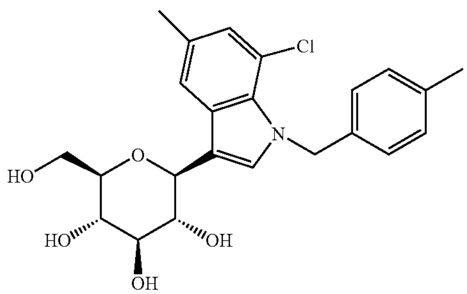 | 2.26 (3H, s), 2.37 (3H, s), 3.4-3.55 (3H, m), 3.65-3.75 (2H, m), 3.85-3.95 (1H, m), 4.45 (1H, d, J = 9.6 Hz), 5.6-5.75 (2H, m), 6.85-6.95 (3H, m), 7.0-7.1 (2H, m), 7.29 (1H, s), 7.45-7.5 (1H, m) |
| Example 103 | 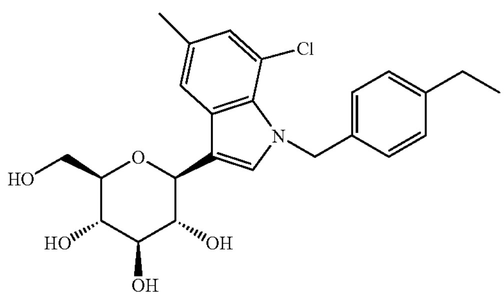 | 1.17 (3H, t, J = 7.5 Hz), 2.37 (3H, s), 2.57 (2H, q, J = 7.5 Hz), 3.4-3.55 (3H, m), 3.65-3.75 (2H, m), 3.85-3.95 (1H, m), 4.45 (1H, d, J = 9.5 Hz), 5.6-5.75 (2H, m), 6.9-7.0 (3H, m), 7.05-7.15 (2H, m), 7.29 (1H, s), 7.45-7.5 (1H, m) |
| Example 104 | 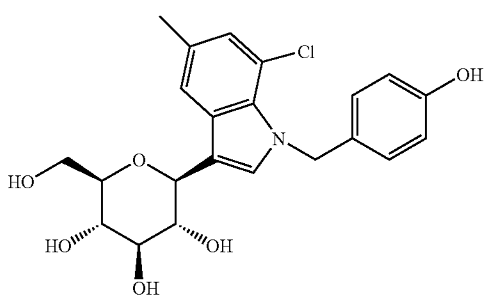 | 2.37 (3H, s), 3.4-3.55 (3H, m), 3.65-3.75 (2H, m), 3.85-3.95 (1H, m), 4.44 (1H, d, J = 9.4 Hz), 5.55-5.65 (2H, m), 6.6-6.7 (2H, m), 6.85-7.0 (3H, m), 7.28 (1H, s), 7.4-7.5 (1H, m) |
| Example 105 | 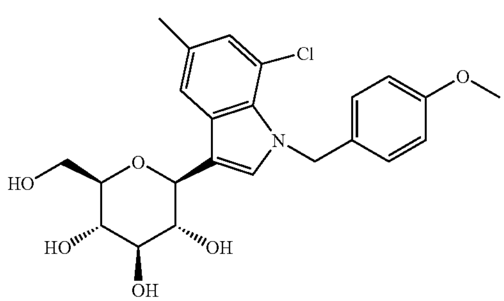 | 2.37 (3H, s), 3.4-3.55 (3H, m), 3.65-3.75 (5H, m), 3.85-3.95 (1H, m), 4.45 (1H, d, J = 9.7 Hz), 5.6-5.7 (2H, m), 6.75-6.85 (2H, m), 6.9-6.95 (1H, m), 6.95-7.05 (2H, m), 7.29 (1H, s), 7.45-7.5 (1H, m) |

TABLE 6-continued
| No. | Structure | $^1$H-NMR (CD$_3$OD) δ ppm: |
|---|---|---|
| Example 106 | 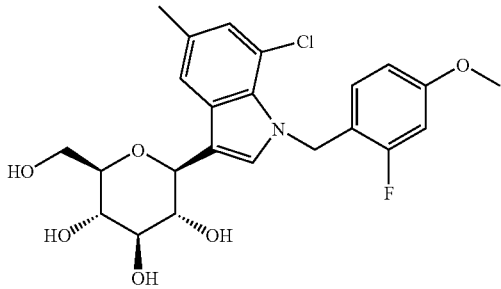 | 2.37 (3H, s), 3.4-3.55 (3H, m), 3.6-3.8 (5H, m), 3.85-3.95 (1H, m), 4.45 (1H, d, J = 9.4 Hz), 5.69 (2H, s), 6.5-6.65 (2H, m), 6.65-6.75 (1H, m), 6.9-7.0 (1H, m), 7.28 (1H, s), 7.45-7.5 (1H, m) |
| Example 107 | 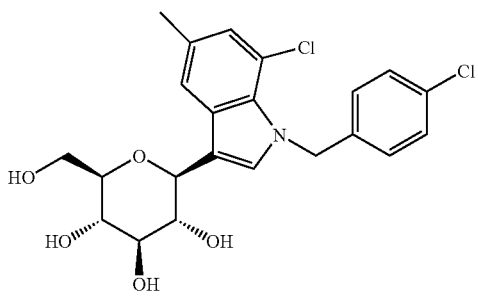 | 2.37 (3H, s), 3.4-3.55 (3H, m), 3.65-3.75 (2H, m), 3.85-3.95 (1H, m), 4.46 (1H, d, J = 9.7 Hz), 5.69 (2H, s), 6.9-7.05 (3H, m), 7.2-7.3 (2H, m), 7.32 (1H, s), 7.45-7.55 (1H, m) |
| Example 108 | 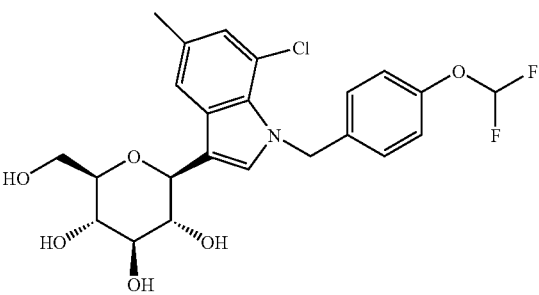 | 2.37 (3H, s), 3.4-3.55 (3H, m), 3.65-3.75 (2H, m), 3.85-3.95 (1H, m), 4.46 (1H, d, J = 9.7 Hz), 5.71 (2H, s), 6.55-6.9 (1H, m), 6.9-7.1 (5H, m), 7.33 (1H, s), 7.45-7.55 (1H, m) |
| Example 109 | 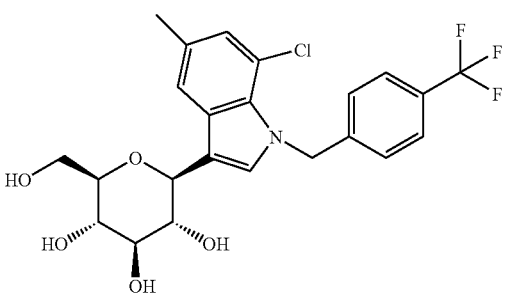 | 2.38 (3H, s), 3.4-3.55 (3H, m), 3.65-3.75 (2H, m), 3.85-3.95 (1H, m), 4.48 (1H, d, J = 9.5 Hz), 5.8 (2H, s), 6.9-7.0 (1H, m), 7.1-7.2 (2H, m), 7.35 (1H, s), 7.45-7.6 (3H, m) |
| Example 110 | 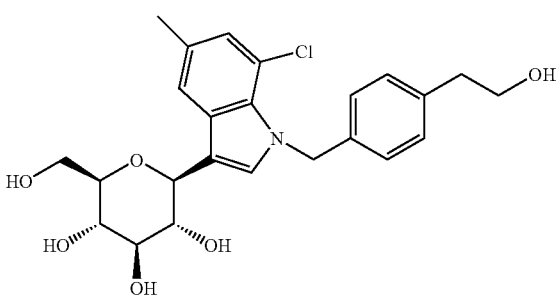 | 2.37 (3H, s), 2.75 (2H, t, J = 7.0 Hz), 3.4-3.55 (3H, m), 3.6-3.75 (4H, m), 3.85-3.95 (1H, m), 4.45 (1H, d, J = 9.3 Hz), 5.6-5.75 (2H, m), 6.9-7.0 (3H, m), 7.05-7.15 (2H, m), 7.3 (1H, s), 7.45-7.5 (1H, m) |

TABLE 6-continued

| No. | Structure | ¹H-NMR (CD₃OD) δ ppm: |
|---|---|---|
| Example 111 | 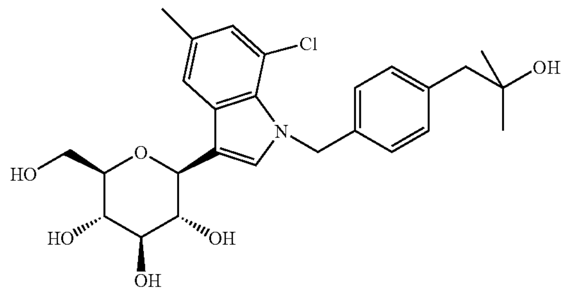 | 1.12 (6H, s), 2.37 (3H, s), 2.68 (2H, s), 3.4-3.55 (3H, m), 3.65-3.75 (2H, m), 3.85-3.95 (1H, m), 4.46 (1H, d, J = 10.0 Hz), 5.6-5.75 (2H, m), 6.9-7.0 (3H, m), 7.05-7.15 (2H, m), 7.31 (1H, s), 7.45-7.5 (1H, m) |
| Example 112 | 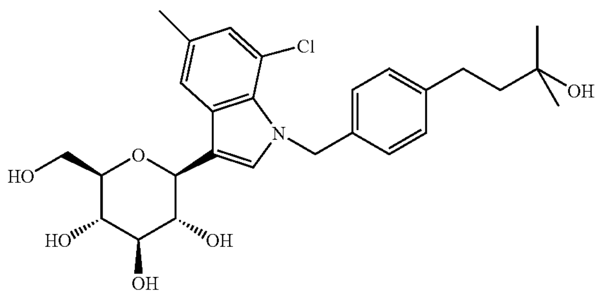 | 1.21 (6H, s), 1.65-1.75 (2H, m), 2.37 (3H, s), 2.55-2.65 (2H, m), 3.4-3.55 (3H, m), 3.65-3.75 (2H, m), 3.85-3.95 (1H, m), 4.45 (1H, d, J = 9.2 Hz), 5.6-5.75 (2H, m), 6.9-7.0 (3H, m), 7.05-7.15 (2H, m), 7.29 (1H, s), 7.45-7.5 (1H, m) |
| Example 113 | 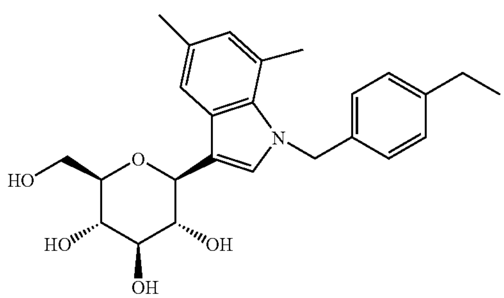 | 1.17 (3H, t, J = 7.6 Hz), 2.34 (3H, s), 2.42 (3H, s), 2.58 (2H, q, J = 7.6 Hz), 3.4-3.55 (3H, m), 3.65-3.8 (2H, m), 3.85-3.95 (1H, m), 4.47 (1H, d, J = 9.7 Hz), 5.52 (2H, s), 6.6-6.7 (1H, m), 6.8-6.9 (2H, m), 7.05-7.15 (2H, m), 7.21 (1H, s), 7.3-7.4 (1H, m) |
| Example 114 | 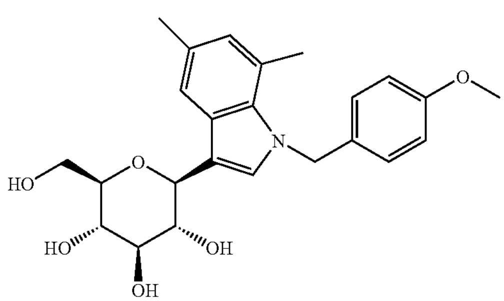 | 2.34 (3H, s), 2.43 (3H, s), 3.4-3.55 (3H, m), 3.6-3.8 (5H, m), 3.85-3.95 (1H, m), 4.46 (1H, d, J = 9.8 Hz), 5.49 (2H, s), 6.6-6.7 (1H, m), 6.75-6.9 (4H, m), 7.2 (1H, s), 7.3-7.4 (1H, m) |
| Example 115 | 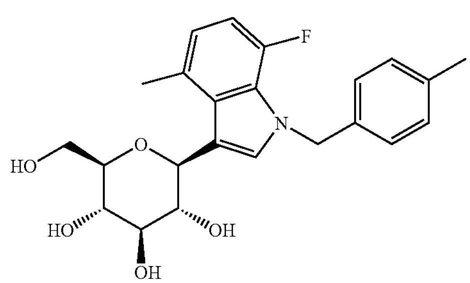 | 2.27 (3H, s), 2.67 (3H, s), 3.35-3.55 (3H, m), 3.65 (1H, dd, J = 12.0, 5.9 Hz), 3.7-3.8 (1H, m), 3.87 (1H, dd, J = 12.0, 2.2 Hz), 4.76 (1H, d, J = 9.9 Hz), 5.38 (1H, d, J = 15.7 Hz), 5.46 (1H, d, J = 15.7 Hz), 6.6-6.75 (2H, m), 6.95-7.1 (4H, m), 7.37 (1H, s) |

TABLE 6-continued

| No. | Structure | $^1$H-NMR (CD$_3$OD) δ ppm: |
|---|---|---|
| Example 116 | 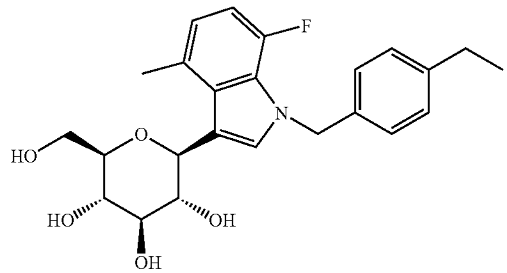 | 1.17 (3H, t, J = 7.6 Hz), 2.58 (2H, q, J = 7.6 Hz), 2.67 (3H, s), 3.35-3.6 (3H, m), 3.65 (1H, dd, J = 12.2, 5.7 Hz), 3.7-3.8 (1H, m), 3.87 (1H, dd, J = 12.2, 2.0 Hz), 4.76 (1H, d, J = 9.8 Hz), 5.39 (1H, d, J = 15.8 Hz), 5.47 (1H, d, J = 15.8 Hz), 6.65-6.75 (2H, m), 7.0-7.15 (4H, m), 7.37 (1H, s) |
| Example 117 | 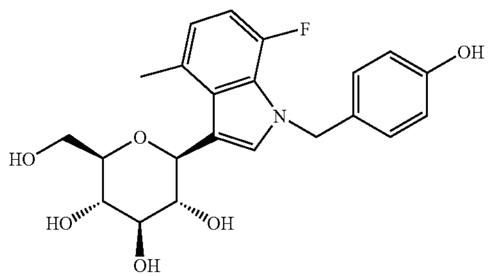 | 2.66 (3H, s), 3.35-3.55 (3H, m), 3.64 (1H, dd, J = 12.0, 5.9 Hz), 3.65-3.8 (1H, m), 3.86 (1H, dd, J = 12.0, 2.2 Hz), 4.76 (1H, d, J = 9.7 Hz), 5.31 (1H, d, J = 15.5 Hz), 5.4 (1H, d, J = 15.5 Hz), 6.6-6.75 (4H, m), 6.95-7.05 (2H, m), 7.35 (1H, s) |
| Example 118 | 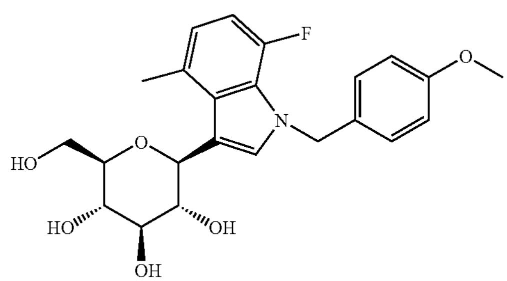 | 2.66 (3H, s), 3.35-3.55 (3H, m), 3.64 (1H, dd, J = 12.2, 5.8 Hz), 3.7-3.8 (4H, m), 3.86 (1H, dd, J = 12.2, 2.4 Hz), 4.76 (1H, d, J = 9.8 Hz), 5.35 (1H, d, J = 15.3 Hz), 5.44 (1H, d, J = 15.3 Hz), 6.65-6.75 (2H, m), 6.75-6.85 (2H, m), 7.05-7.15 (2H, m), 7.37 (1H, s) |
| Example 119 | 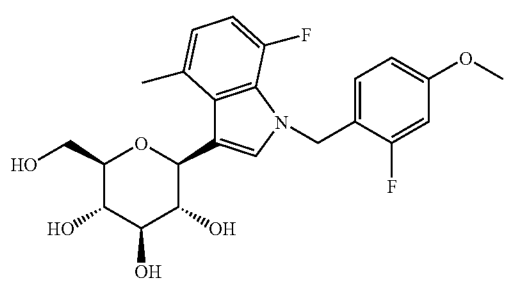 | 2.66 (3H, s), 3.35-3.55 (3H, m), 3.64 (1H, dd, J = 12.0, 5.9 Hz), 3.65-3.8 (4H, m), 3.86 (1H, dd, J = 12.0, 2.2 Hz), 4.75 (1H, d, J = 9.7 Hz), 5.42 (1H, d, J = 15.8 Hz), 5.5 (1H, d, J = 15.8 Hz), 6.55-6.65 (1H, m), 6.65-6.75 (3H, m), 6.85-6.95 (1H, m), 7.34 (1H, s) |
| Example 120 | 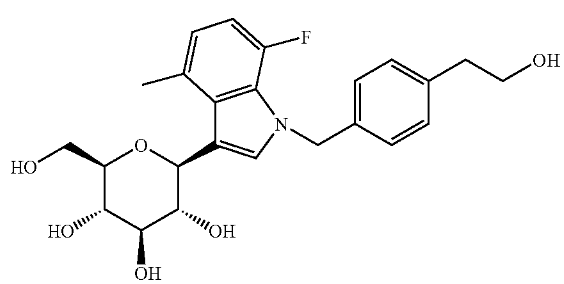 | 2.67 (3H, s), 2.76 (2H, t, J = 6.8 Hz), 3.35-3.55 (3H, m), 3.6-3.8 (4H, m), 3.87 (1H, dd, J = 12.3, 2.4 Hz), 4.76 (1H, d, J = 9.8 Hz), 5.39 (1H, d, J = 16.0 Hz), 5.48 (1H, d, J = 16.0 Hz), 6.6-6.75 (2H, m), 7.0-7.1 (2H, m), 7.1-7.2 (2H, m), 7.38 (1H, s) |

TABLE 6-continued

| No. | Structure | $^1$H-NMR (CD$_3$OD) δ ppm: |
|---|---|---|
| Example 121 | 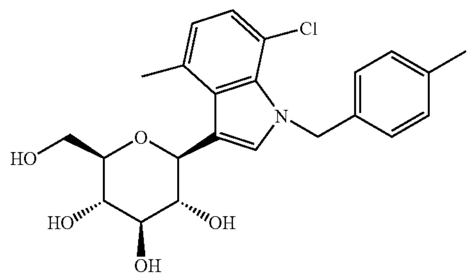 | 2.27 (3H, s), 2.71 (3H, s), 3.35-3.55 (3H, m), 3.6-3.7 (1H, m), 3.7-3.8 (1H, m), 3.85-3.95 (1H, m), 4.78 (1H, d, J = 9.9 Hz), 5.64 (1H, d, J = 16.4 Hz), 5.81 (1H, d, J = 16.4 Hz), 6.7-6.8 (1H, m), 6.85-7.0 (3H, m), 7.0-7.1 (2H, m), 7.39 (1H, s) |
| Example 122 | 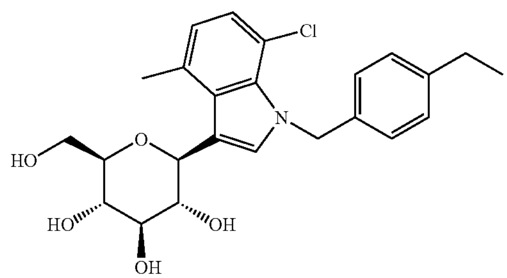 | 1.17 (3H, t, J = 7.5 Hz), 2.58 (2H, q, J = 7.5 Hz), 2.71 (3H, s), 3.35-3.55 (3H, m), 3.6-3.7 (1H, m), 3.7-3.8 (1H, m), 3.85-3.95 (1H, m), 4.75-4.85 (1H, m), 5.66 (1H, d, J = 16.4 Hz), 5.83 (1H, d, J = 16.4 Hz), 6.7-6.8 (1H, m), 6.85-7.0 (3H, m), 7.05-7.15 (2H, m), 7. |
| Example 123 | 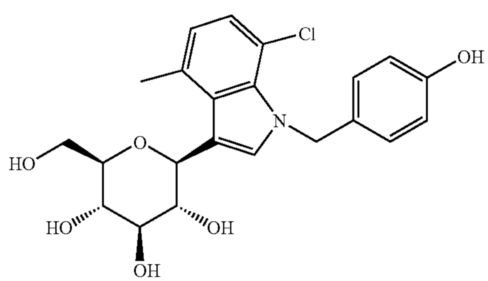 | 2.71 (3H, s), 3.35-3.55 (3H, m), 3.6-3.7 (1H, m), 3.7-3.8 (1H, m), 3.8-3.9 (1H, m), 4.78 (1H, d, J = 9.9 Hz), 5.58 (1H, d, J = 16.1 Hz), 5.76 (1H, d, J = 16.1 Hz), 6.6-6.7 (2H, m), 6.7-6.8 (1H, m), 6.85-7.0 (3H, m), 7.37 (1H, s) |
| Example 124 | 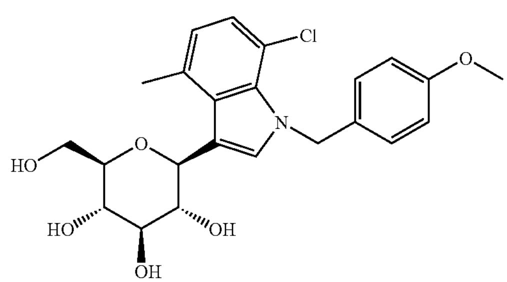 | 2.71 (3H, s), 3.35-3.55 (3H, m), 3.6-3.7 (1H, m), 3.7-3.8 (4H, m), 3.87 (1H, dd, J = 12.0, 2.3 Hz), 4.75-4.85 (1H, m), 5.62 (1H, d, J = 16.3 Hz), 5.79 (1H, d, J = 16.3 Hz), 6.7-6.85 (3H, m), 6.9-7.0 (3H, m), 7.38 (1H, s) |
| Example 125 | 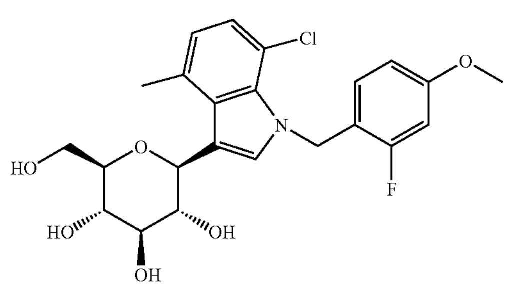 | 2.71 (3H, s), 3.35-3.55 (3H, m), 3.6-3.7 (1H, m), 3.7-3.8 (4H, m), 3.85-3.95 (1H, m), 4.78 (1H, d, J = 9.9 Hz), 5.67 (1H, d, J = 16.5 Hz), 5.82 (1H, d, J = 16.5 Hz), 6.45-6.6 (2H, m), 6.65-6.8 (2H, m), 6.9-7.0 (1H, m), 7.38 (1H, s) |

TABLE 6-continued

| No. | Structure | $^1$H-NMR (CD$_3$OD) δ ppm: |
|---|---|---|
| Example 126 | 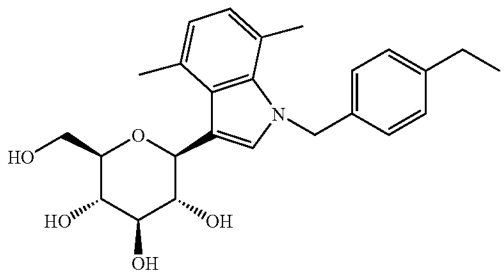 | 1.17 (3H, t, J = 7.5 Hz), 2.42 (3H, s), 2.57 (2H, q, J = 7.5 Hz), 2.7 (3H, s), 3.35-3.6 (3H, m), 3.6-3.95 (3H, m), 4.75-4.9 (1H, m), 5.52 (1H, d, J = 15.8 Hz), 5.61 (1H, d, J = 15.8 Hz), 6.6-6.75 (2H, m), 6.75-6.85 (2H, m), 7.0-7.15 (2H, m), 7.3 (1H, s) |

Examples 127 to 160

Examples 127 to 160 were prepared in a similar manner to that described in Example 10 using the corresponding starting materials. N,N-Dimethylformamide was used as a solvent instead of acetonitrile as occasion demands.

The structures and NMR spectrum data of the compounds of Examples 127 to 160 are described in Table 7.

TABLE 7

| No. | Structure | $^1$H-NMR (CD$_3$OD) δ ppm: |
|---|---|---|
| Example 127 | 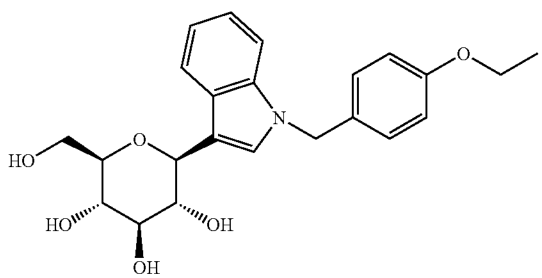 | 1.34 (3H, t, J = 6.9 Hz), 3.4-3.55 (3H, m), 3.65-3.8 (2H, m), 3.85-3.95 (1H, m), 3.97 (2H, q, J= 6.9 Hz), 4.48 (1H, d, J = 9.5 Hz), 5.26 (2H, s), 6.75-6.85 (2H, m), 7.0-7.15 (4H, m), 7.25-7.35 (2H, m), 7.7-7.75 (1H, m) |
| Example 128 | 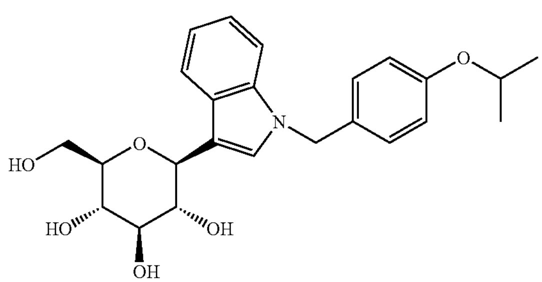 | 1.25 (6H, d, J = 6.4 Hz), 3.4-3.55 (3H, m), 3.65-3.8 (2H, m), 3.85-3.95 (1H, m), 4.45-4.6 (2H, m), 5.26 (2H, s), 6.75-6.85 (2H, m), 7.0-7.15 (4H, m), 7.3-7.35 (2H, m), 7.7-7.75 (1H, m) |
| Example 129 | 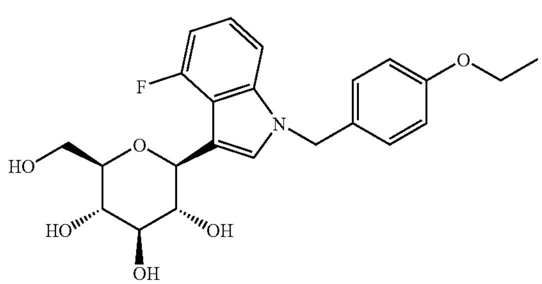 | 1.34 (3H, t, J = 6.9 Hz), 3.4-3.55 (3H, m), 3.6-3.7 (1H, m), 3.7-3.8 (1H, m), 3.8-3.9 (1H, m), 3.98 (2H, q, J= 6.9 Hz), 4.6 (1H, d, J = 9.7 Hz), 5.2-5.35 (2H, m), 6.65-6.75 (1H, m), 6.8-6.85 (2H, m), 7.0-7.1 (1H, m), 7.1-7.2 (3H, m), 7.36 (1H, s) |

TABLE 7-continued

| No. | Structure | ¹H-NMR (CD₃OD) δ ppm: |
|---|---|---|
| Example 130 | 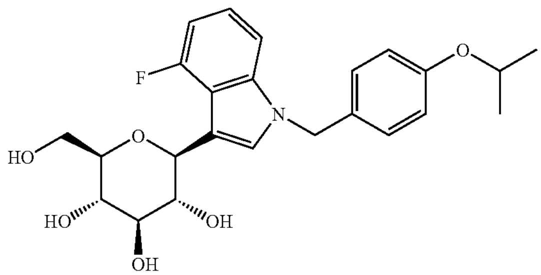 | 1.26 (6H, d, J = 6.1 Hz), 3.4-3.55 (3H, m), 3.6-3.7 (1H, m), 3.7-3.8 (1H, m), 3.8-3.9 (1H, m), 4.45-4.65 (2H, m), 5.2-5.35 (2H, m), 6.65-6.75 (1H, m), 6.75-6.85 (2H, m), 7.0-7.2 (4H, m), 7.36 (1H, s) |
| Example 131 | 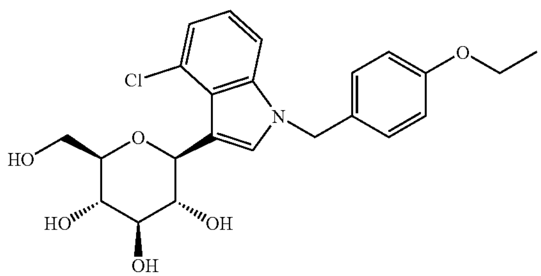 | 1.34 (3H, t, J = 7.0 Hz), 3.4-3.6 (3H, m), 3.65-3.9 (3H, m), 3.97 (2H, q, J = 7.0 Hz), 5.1 (1H, d, J = 9.8 Hz), 5.26 (1H, d, J = 15.4 Hz), 5.32 (1H, d, J = 15.4 Hz), 6.75-6.85 (2H, m), 7.0-7.15 (4H, m), 7.25-7.35 (1H, m), 7.47 (1H, s) |
| Example 132 | 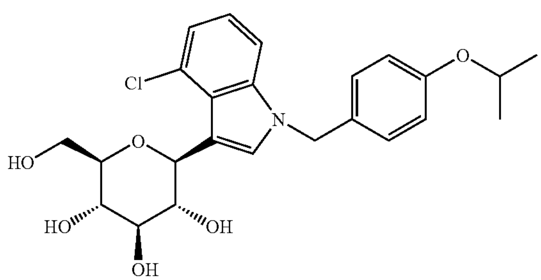 | 1.26 (6H, d, J = 6.1 Hz), 3.4-3.6 (3H, m), 3.65-3.9 (3H, m), 4.45-4.6 (1H, m), 5.1 (1H, d, J = 9.7 Hz), 5.26 (1H, d, J = 15.5 Hz), 5.32 (1H, d, J = 15.5 Hz), 6.75-6.85 (2H, m), 7.0-7.15 (4H, m), 7.25-7.35 (1H, m), 7.48 (1H, s) |
| Example 133 | 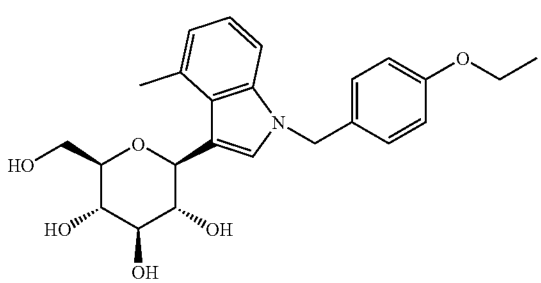 | 1.33 (3H, t, J = 7.0 Hz), 2.71 (3H, s), 3.35-3.45 (1H, m), 3.45-3.55 (2H, m), 3.6-3.7 (1H, m), 3.7-3.8 (1H, m), 3.8-3.9 (1H, m), 3.96 (2H, q, J = 7.0 Hz), 4.79 (1H, d, J = 9.7 Hz), 5.23 (1H, d, J = 15.8 Hz), 5.28 (1H, d, J = 15.8 Hz), 6.75-6.85 (3H, m), 6.9-7.0 (1H, m), 7.05-7.2 (3H, m), 7.36 (1H, s) |
| Example 134 | 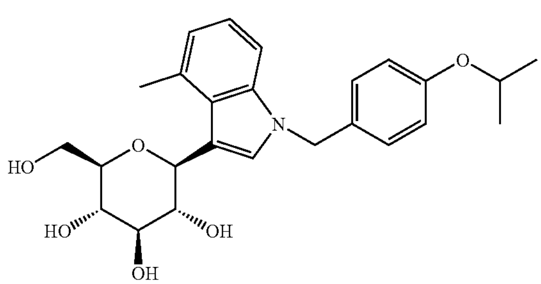 | 1.25 (6H, d, J = 6.0 Hz), 2.71 (3H, s), 3.35-3.45 (1H, m), 3.45-3.55 (2H, m), 3.6-3.7 (1H, m), 3.7-3.8 (1H, m), 3.8-3.9 (1H, m), 4.45-4.6 (1H, m), 4.79 (1H, d, J = 9.9 Hz), 5.22 (1H, d, J= 15.6 Hz), 5.28 (1H, d, J = 15.6 Hz), 6.75-6.85 (3H, m), 6.95-7.0 (1H, m), 7.05-7.2 (3H, m), 7.36 (1H, s) |

TABLE 7-continued

| No. | Structure | $^1$H-NMR (CD$_3$OD) δ ppm: |
|---|---|---|
| Example 135 | 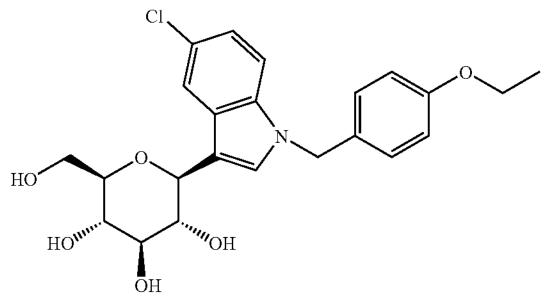 | 1.34 (3H, t, J = 7.0 Hz), 3.4-3.55 (3H, m), 3.6-3.75 (2H, m), 3.85-3.95 (1H, m), 3.98 (2H, q, J = 7.0 Hz), 4.44 (1H, d, J = 9.4 Hz), 5.26 (2H, s), 6.75-6.85 (2H, m), 7.0-7.15 (3H, m), 7.3 (1H, d, J = 8.7 Hz), 7.38 (1H, s), 7.7 (1H, d, J = 2.1 Hz) |
| Example 136 | 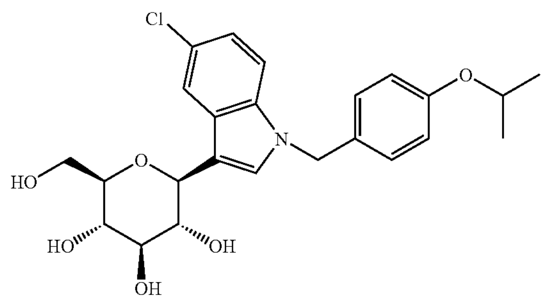 | 1.26 (6H, d, J = 5.9 Hz), 3.4-3.55 (3H, m), 3.6-3.75 (2H, m), 3.85-3.95 (1H, m), 4.44 (1H, d, J = 9.7 Hz), 4.45-4.6 (1H, m), 5.26 (2H, s), 6.75-6.85 (2H, m), 7.0-7.15 (3H, m), 7.3 (1H, d, J = 8.7 Hz), 7.39 (1H, s), 7.7 (1H, d, J = 1.9 Hz) |
| Example 137 | 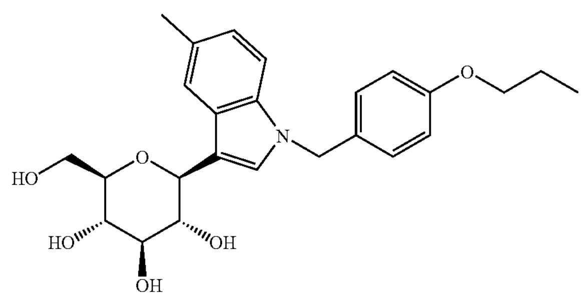 | 1.0 (3H, t, J = 7.4 Hz), 1.65-1.8 (2H, m), 2.39 (3H, s), 3.4-3.55 (3H, m), 3.6-3.8 (2H, m), 3.8-3.95 (3H, m), 4.45 (1H, d, J = 9.9 Hz), 5.23 (2H, s), 6.75-6.85 (2H, m), 6.9-7.0 (1H, m), 7.05-7.15 (2H, m), 7.15-7.25 (1H, m), 7.27 (1H, s), 7.45-7.55 (1H, m) |
| Example 138 | 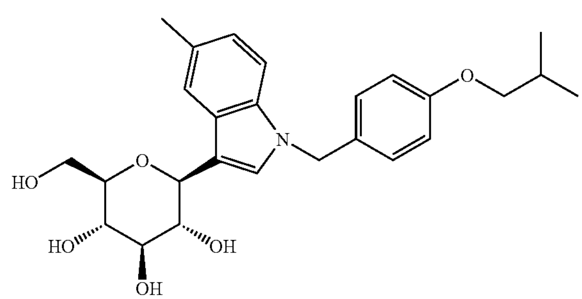 | 0.99 (6H, d, J = 7.0 Hz), 1.95-2.1 (1H, m), 2.39 (3H, s), 3.4-3.55 (3H, m), 3.6-3.8 (4H, m), 3.85-3.95 (1H, m), 4.45 (1H, d, J = 9.3 Hz), 5.23 (2H, s), 6.75-6.85 (2H, m), 6.9-7.0 (1H, m), 7.05-7.15 (2H, m), 7.15-7.25 (1H, m), 7.27 (1H, s), 7.45-7.55 (1H, m) |
| Example 139 | 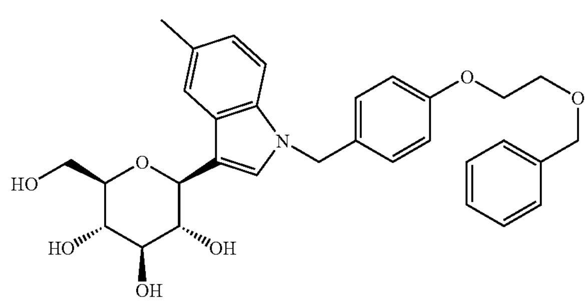 | 2.39 (3H, s), 3.4-3.55 (3H, m), 3.65-3.85 (4H, m), 3.85-3.95 (1H, m), 4.05-4.15 (2H, m), 4.45 (1H, d, J = 9.6 Hz), 4.58 (2H, s), 5.24 (2H, s), 6.8-6.9 (2H, m), 6.9-7.0 (1H, m), 7.05-7.15 (2H, m), 7.15-7.4 (7H, m), 7.45-7.55 (1H, m) |

TABLE 7-continued

| No. | Structure | $^1$H-NMR (CD$_3$OD) δ ppm: |
|---|---|---|
| Example 140 | 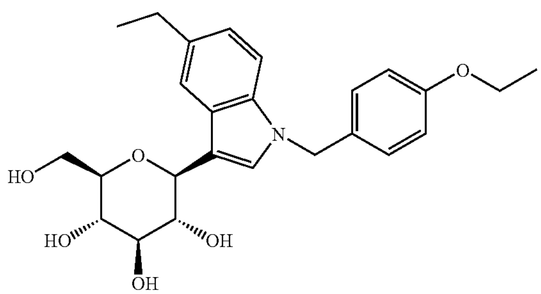 | 1.24 (3H, t, J = 7.6 Hz), 1.34 (3H, t, J = 7.0 Hz), 2.7 (2H, q, J = 7.6 Hz), 3.4-3.55 (3H, m), 3.65-3.8 (2H, m), 3.85-3.95 (1H, m), 3.97 (2H, q, J = 7.0 Hz), 4.46 (1H, d, J = 9.7 Hz), 5.24 (2H, s), 6.75-6.85 (2H, m), 6.95-7.0 (1H, m), 7.05-7.15 (2H, m), 7.22 (1H, d, J = 8.3 Hz), 7.29 (1H, s), 7.5-7.55 (1H, m) |
| Example 141 | 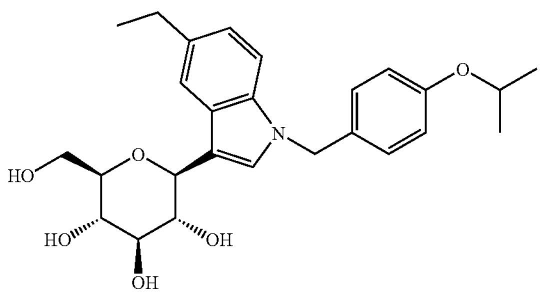 | 1.2-1.3 (9H, m), 2.7 (2H, q, J = 7.6 Hz), 3.4-3.55 (3H, m), 3.65-3.8 (2H, m), 3.85-3.95 (1H, m), 4.47 (1H, d, J = 9.5 Hz), 4.5-4.6 (1H, m), 5.24 (2H, s), 6.75-6.85 (2H, m), 6.95-7.0 (1H, m), 7.05-7.15 (2H, m), 7.23 (1H, d, J = 8.5 Hz), 7.29 (1H, s), 7.5-7.55 (1H, m) |
| Example 142 | 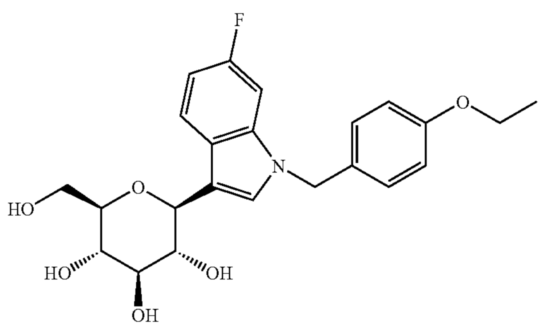 | 1.34 (3H, t, J = 7.0 Hz), 3.4-3.55 (3H, m), 3.6-3.75 (2H, m), 3.85-3.95 (1H, m), 3.98 (2H, q, J = 7.0 Hz), 4.45 (1H, d, J = 9.6 Hz), 5.22 (2H, s), 6.75-6.85 (3H, m), 6.95-7.2 (3H, m), 7.32 (1H, s), 7.6-7.7 (1H, m) |
| Example 143 | 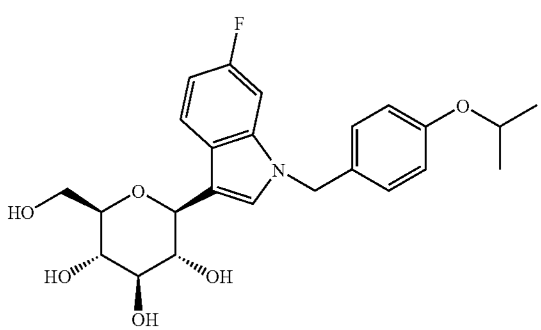 | 1.26 (6H, d, J = 5.9 Hz), 3.4-3.55 (3H, m), 3.6-3.75 (2H, m), 3.85-3.95 (1H, m), 4.45 (1H, d, J = 9.7 Hz), 4.54.6 (1H, m), 5.22 (2H, s), 6.75-6.85 (3H, m), 7.0-7.1 (1H, m), 7.1-7.15 (2H, m), 7.32 (1H, s), 7.65-7.75 (1H, m) |
| Example 144 | 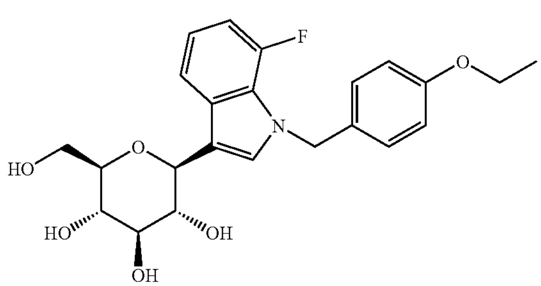 | 1.33 (3H, t, J = 7.0 Hz), 3.4-3.55 (3H, m), 3.65-3.75 (2H, m), 3.85-3.95 (1H, m), 3.96 (2H, q, J = 7.0 Hz), 4.45 (1H, d, J = 10.0 Hz), 5.38 (2H, s), 6.75-6.85 (3H, m), 6.9-7.0 (1H, m), 7.05-7.15 (2H, m), 7.33 (1H, s), 7.45-7.55 (1H, m) |

TABLE 7-continued

| No. | Structure | $^1$H-NMR (CD$_3$OD) δ ppm: |
| --- | --- | --- |
| Example 145 | 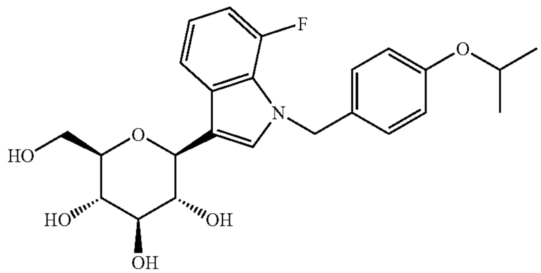 | 1.25 (6H, d, J = 6.1 Hz), 3.4-3.55 (3H, m), 3.6-3.75 (2H, m), 3.8-3.95 (1H, m), 4.4-4.6 (2H, m), 5.38 (2H, s), 6.75-6.9 (3H, m), 6.9-7.0 (1H, m), 7.05-7.15 (2H, m), 7.34 (1H, s), 7.45-7.55 (1H, m) |
| Example 146 | 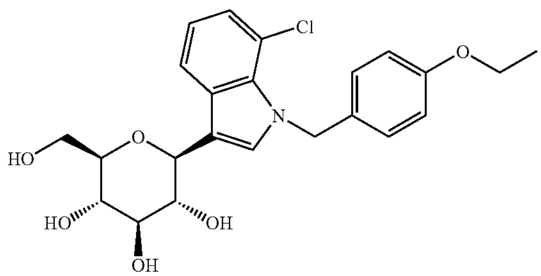 | 1.34 (3H, t, J = 7.0 Hz), 3.4-3.55 (3H, m), 3.6-3.75 (2H, m), 3.85-3.95 (1H, m), 3.97 (2H, q, J = 7.0 Hz), 4.48 (1H, d, J = 9.3 Hz), 5.6-5.75 (2H, m), 6.75-6.85 (2H, m), 6.9-7.05 (3H, m), 7.05-7.15 (1H, m), 7.35 (1H, s), 7.65-7.75 (1H, m) |
| Example 147 | 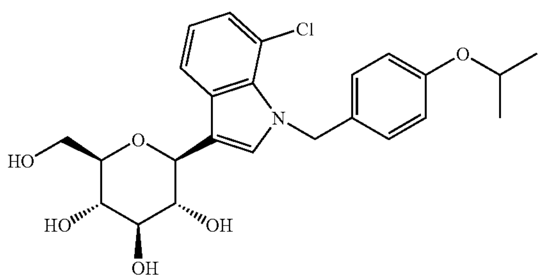 | 1.25 (6H, d, J = 5.9 Hz), 3.4-3.55 (3H, m), 3.6-3.75 (2H, m), 3.85-3.95 (1H, m), 4.4-4.6 (2H, m), 5.6-5.75 (2H, m), 6.7-6.8 (2H, m), 6.9-7.05 (3H, m), 7.05-7.15 (1H, m), 7.35 (1H, s), 7.65-7.75 (1H, m) |
| Example 148 | 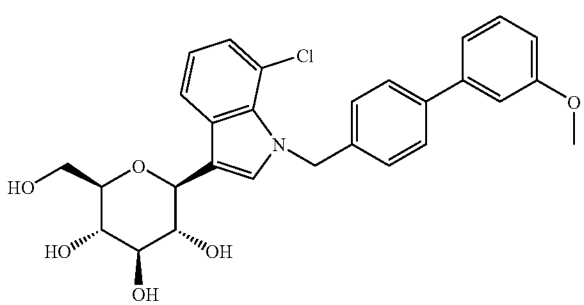 | 3.4-3.55 (3H, m), 3.65-3.75 (2H, m), 3.81 (3H, s), 3.85-3.95 (1H, m), 4.51 (1H, d, J = 10.0 Hz), 5.75-5.9 (2H, m), 6.8-6.9 (1H, m), 6.95-7.05 (1H, m), 7.05-7.15 (5H, m), 7.25-7.35 (1H, m), 7.41 (1H, s), 7.45-7.55 (2H, m), 7.7-7.75 (1H, m) |
| Example 149 | 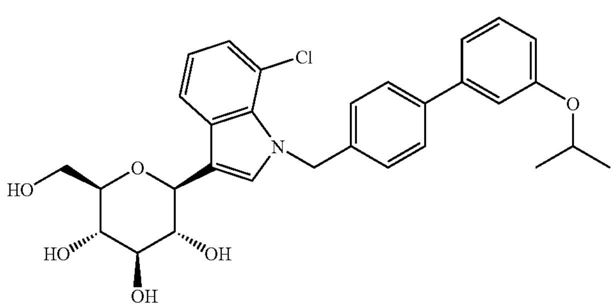 | 1.3 (6H, d, J = 6.3 Hz), 3.4-3.55 (3H, m), 3.65-3.75 (2H, m), 3.85-3.95 (1H, m), 4.51 (1H, d, J = 9.4 Hz), 4.55-4.7 (1H, m), 5.75-5.85 (2H, m), 6.8-6.9 (1H, m), 6.95-7.15 (6H, m), 7.25-7.3 (1H, m), 7.4 (1H, s), 7.45-7.5 (2H, m), 7.7-7.75 (1H, m) |

TABLE 7-continued

| No. | Structure | ¹H-NMR (CD₃OD) δ ppm: |
|---|---|---|
| Example 150 | 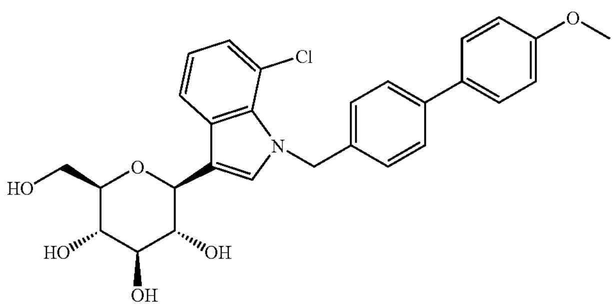 | 3.4-3.55 (3H, m), 3.65-3.75 (2H, m), 3.8 (3H, s), 3.85-3.95 (1H, m), 4.51 (1H, d, J = 9.8 Hz), 5.75-5.85 (2H, m), 6.9-7.05 (3H, m), 7.05-7.15 (3H, m), 7.35-7.55 (5H, m), 7.65-7.75 (1H, m) |
| Example 151 | 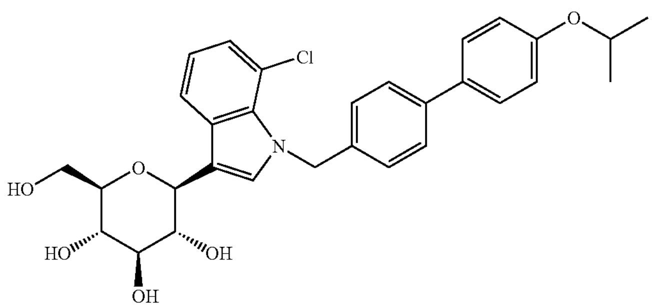 | 1.31 (6H, d, J = 6.1 Hz), 3.4-3.55 (3H, m), 3.65-3.75 (2H, m), 3.85-3.95 (1H, m), 4.51 (1H, d, J = 9.6 Hz), 4.55-4.65 (1H, m), 5.75-5.85 (2H, m), 6.9-6.95 (2H, m), 6.95-7.05 (1H, m), 7.05-7.15 (3H, m), 7.35-7.5 (5H, m), 7.65-7.75 (1H, m) |
| Example 152 | 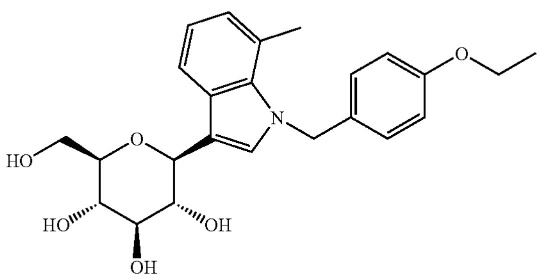 | 1.33 (3H, t, J = 6.8 Hz), 2.48 (3H, s), 3.4-3.55 (3H, m), 3.65-3.8 (2H, m), 3.85-4.0 (3H, m), 4.49 (1H, d, J = 9.6 Hz), 5.45-5.6 (2H, m), 6.75-6.95 (6H, m), 7.25 (1H, s), 7.55-7.65 (1H, m) |
| Example 153 | 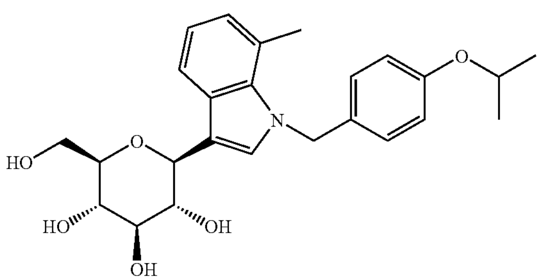 | 1.25 (6H, d, J = 5.9 Hz), 2.49 (3H, s), 3.4-3.55 (3H, m), 3.65-3.8 (2H, m), 3.85-3.95 (1H, m), 4.45-4.55 (2H, m), 5.45-5.6 (2H, m), 6.75-6.95 (6H, m), 7.25 (1H, s), 7.55-7.65 (1H, m) |
| Example 154 | 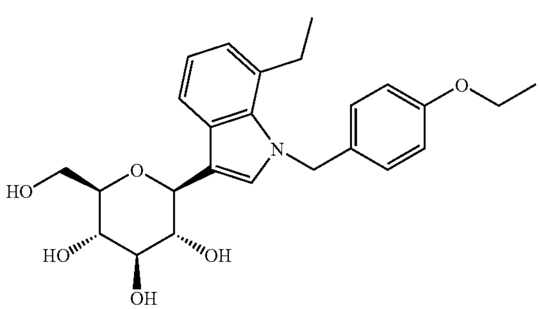 | 1.17 (3H, t, J = 7.5 Hz), 1.33 (3H, t, J = 6.9 Hz), 2.82 (2H, q, J = 7.5 Hz), 3.4-3.55 (3H, m), 3.65-3.8 (2H, m), 3.85-3.95 (1H, m), 3.96 (2H, q, J = 6.9 Hz), 4.5 (1H, d, J = 9.8 Hz), 5.48 (2H, s), 6.75-6.95 (5H, m), 6.95-7.0 (1H, m), 7.26 (1H, s), 7.55-7.65 (1H, m) |

TABLE 7-continued

| No. | Structure | $^1$H-NMR (CD$_3$OD) δ ppm: |
|---|---|---|
| Example 155 | 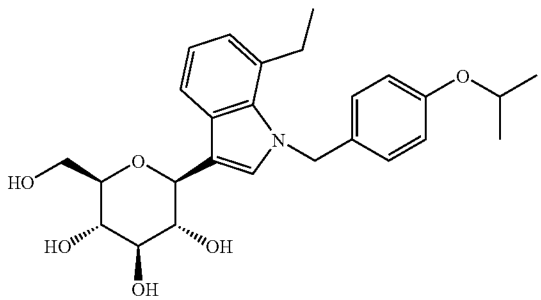 | 1.17 (3H, t, J = 7.5 Hz), 1.25 (6H, d, J = 6.1 Hz), 2.83 (2H, q, J = 7.5 Hz), 3.4-3.55 (3H, m), 3.65-3.8 (2H, m), 3.85-3.95 (1H, m), 4.45-4.55 (2H, m), 5.48 (2H, s), 6.7-6.95 (5H, m), 6.95-7.0 (1H, m), 7.26 (1H, s), 7.55-7.65 (1H, m) |
| Example 156 | 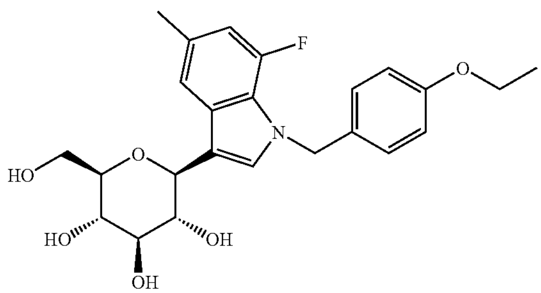 | 1.33 (3H, t, J = 6.9 Hz), 2.37 (3H, s), 3.4-3.55 (3H, m), 3.6-3.75 (2H, m), 3.85-3.95 (1H, m), 3.96 (2H, q, J = 6.9 Hz), 4.42 (1H, d, J = 9.7 Hz), 5.34 (2H, s), 6.6-6.75 (1H, m), 6.75-6.85 (2H, m), 7.05-7.15 (2H, m), 7.25-7.35 (2H, m) |
| Example 157 | 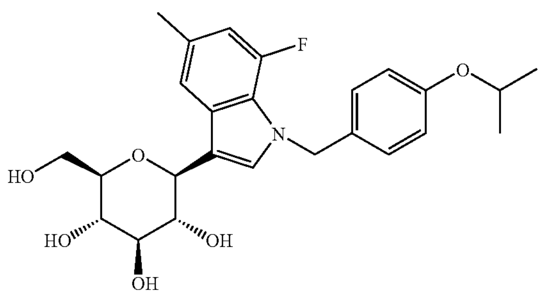 | 1.25 (6H, d, J = 6.0 Hz), 2.37 (3H, s), 3.4-3.55 (3H, m), 3.6-3.75 (2H, m), 3.85-3.95 (1H, m), 4.42 (1H, d, J = 9.4 Hz), 4.45-4.6 (1H, m), 5.34 (2H, s), 6.6-6.75 (1H, m), 6.75-6.85 (2H, m), 7.05-7.15 (2H, m), 7.25-7.35 (2H, m) |
| Example 158 | 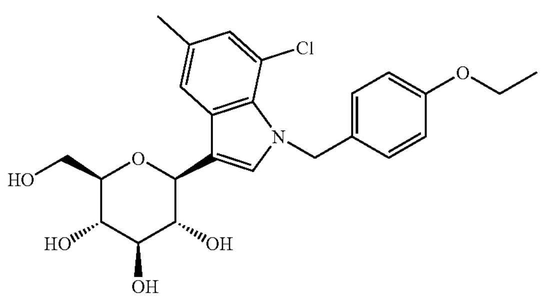 | 1.33 (3H, t, J = 6.9 Hz), 2.37 (3H, s), 3.4-3.55 (3H, m), 3.6-3.75 (2H, m), 3.85-3.95 (1H, m), 3.96 (2H, q, J = 6.9 Hz), 4.45 (1H, d, J = 9.5 Hz), 5.55-5.7 (2H, m), 6.7-6.85 (2H, m), 6.9-7.05 (3H, m), 7.29 (1H, s), 7.4-7.5 (1H, m) |
| Example 159 | 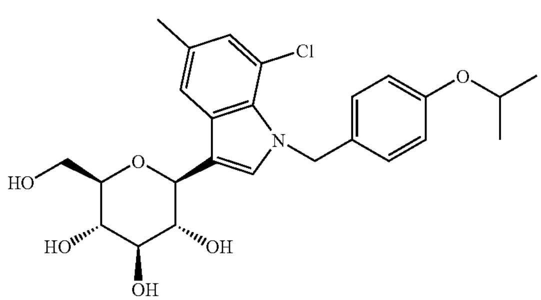 | 1.25 (6H, d, J = 6.0 Hz), 2.37 (3H, s), 3.4-3.55 (3H, m), 3.6-3.75 (2H, m), 3.85-3.95 (1H, m), 4.4-4.6 (2H, m), 5.55-5.7 (2H, m), 6.7-6.85 (2H, m), 6.9-7.05 (3H, m), 7.29 (1H, s), 7.4-7.5 (1H, m) |

TABLE 7-continued

| No. | Structure | $^1$H-NMR (CD$_3$OD) δ ppm: |
|---|---|---|
| Example 160 | 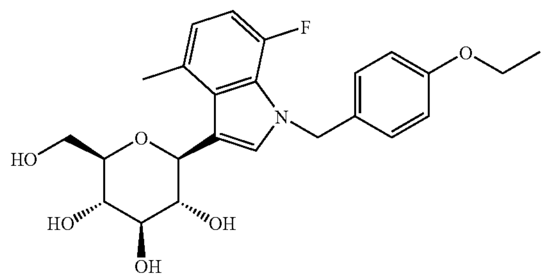 | 1.33 (3H, t, J = 6.9 Hz), 2.66 (3H, s), 3.35-3.55 (3H, m), 3.64 (1H, dd, J = 12.3, 5.9 Hz), 3.7-3.8 (1H, m), 3.86 (1H, dd, J = 12.3, 2.4 Hz), 3.97 (2H, q, J = 6.9 Hz), 4.76 (1H, d, J = 9.5 Hz), 5.34 (1H, d, J = 15.4 Hz), 5.43 (1H, d, J = 15.4 Hz), 6.65-6.75 (2H, m), 6.75-6.85 (2H, m), 7.05-7.15 (2H, m), 7.36 (1H, s) |

Example 161

3-(2,3,4,6-Tetra-O-acetyl-β-D-glucopyranosyl)-7-chloro-1-[4-(2-hydroxyethoxy)benzyl]-1H-indole 1-{4-[2-(tert-Butyldiphenylsilyloxy)ethoxy]benzyl}-7-chloro-3-(β-D-glucopyranosyl)-1H-indole was prepared in a similar manner to that described in Example 1 using the corresponding starting materials.

To a solution of 1-{4-[2-(tert-butyldiphenyl-silyloxy)ethoxy]benzyl}-7-chloro-3-(β-D-glucopyranosyl)-1H-indole (0.30 g) and pyridine (0.30 mL) in dichloromethane (2 mL) were added acetic anhydride (0.36 mL) and 4-dimethylaminopyridine (5 mg) at room temperature, and the mixture was stirred at room temperature overnight. To the reaction mixture was added water, and the resulting mixture was extracted with ethyl acetate. The extract was washed with 1 mol/L hydrochloric acid, water and brine successively, and dried over anhydrous sodium sulfate. The solvent was removed under reduced pressure. The residue was dissolved in tetra hydrofuran (5 mL). To the solution was added tetra (n-butyl)ammonium fluoride (1.0 mol/L tetra hydrofuran solution, 0.50 mL), and the mixture was stirred at room temperature for 1 hour. The reaction mixture was poured into 1 mol/L hydrochloric acid, and the resulting mixture was extracted with ethylacetate. The extract was washed with water and brine successively, and dried over anhydrous sodium sulfate. The solvent was removed under reduced pressure. The residue was washed with a mixed solvent of n-hexane and ethyl acetate (5/1), and dried under reduced pressure to give the title compound (0.23 g).

Example 162

3-(2,3,4,6-Tetra-O-benzyl-β-D-glucopyranosyl)-7-chloro-1-[4-(2-hydroxyethyl)benzyl]-1H-indole To a solution of 3-(2,3,4,6-tetra-O-benzyl-β-D-glucopyranosyl)-7-chloro-1H-indole (0.48 g) in N,N-dimethylformamide (5 mL) was added 55% sodium hydride (37 mg) under ice-cooling, and the mixture was stirred at the same temperature for 15 minutes. To this mixture was added a solution of 4-[2-(tert-butyldiphenylsilyloxy)ethyl]benzyl bromide (0.42 g) in tetra hydrofuran (2 mL) at the same temperature, and the mixture was stirred at the same temperature for 15 minutes, and stirred at room temperature for 1 hour. The reaction mixture was poured into water, and the resulting mixture was extracted with ethyl acetate. The extract was washed with water and brine successively, and dried over anhydrous sodium sulfate. The solvent was removed under reduced pressure. The residue was dissolved in tetra hydrofuran (5 mL). To the solution was added tetra(n-butyl)ammonium fluoride (1.0 mol/L tetra hydrofuran solution, 1.07 mL), and the mixture was stirred at room temperature for 30 minutes. The reaction mixture was poured into water, and the resulting mixture was extracted with ethyl acetate. The extract was washed with water and brine successively, and dried over anhydrous sodium sulfate. The solvent was removed under reduced pressure. The residue was washed with a mixed solvent of n-hexane and ethyl acetate (5/1), and dried under reduced pressure to give the title compound (0.50 g).

Example 163

3-(2,3,4,6-Tetra-O-benzyl-β-D-glucopyranosyl)-1-(4-carboxy-benzyl)-7-methyl-1H-indole To a solution of 3-(2,3,4,6-tetra-O-benzyl-β-D-glucopyranosyl)-7-methyl-1H-indole (0.28 g) in N,N-dimethyl-formamide (4 mL) was added 55% sodium hydride (22 mg) under ice-cooling, and the mixture was stirred at the same temperature for 15 minutes. To this mixture was added methyl 4-(bromo-methyl)benzoate (0.12 g) at the same temperature, and the mixture was stirred at the same temperature for 15 minutes, and stirred at room temperature for 1 hour. The reaction mixture was poured into 0.5 mol/L hydrochloric acid, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=5/1-3/1) to give 3-(2,3,4,6-tetra-O-benzyl-β-D-glucopyranosyl)-1-[4-(methoxycarbonyl)benzyl]-7-methyl-1H-indole (0.32 g). This material was dissolved in a mixed solvent of ethanol (5 mL) and tetra hydrofuran (2.5 mL). To the solution was added potassium hydroxide (0.45 g), and the mixture was stirred at 50° C. overnight. The reaction mixture was poured into 1 mol/L hydrochloric acid (10 mL), and the resulting mixture was extracted with ethyl acetate. The extract was washed with water and brine successively, and dried over anhydrous sodium sulfate. The solvent was removed under reduced pressure to give the title compound (0.31 g)

Example 164

3-(2,3,4,6-Tetra-O-benzyl-β-D-glucopyranosyl)-1-[4-((E)-2-carboxyvinyl)benzyl]-7-methyl-1H-indole To a solution of 3-(2,3,4,6-tetra-O-benzyl-β-D-glucopyranosyl)-7-methyl-1H-indole (1.18 g) in N,N-dimethylformamide (10 mL) was added 55% sodium hydride (87 mg) under ice-cooling, and the mixture was stirred at the same temperature for 15 minutes. To this mixture was added 4-iodobenzyl bromide (0.62 g) at the same temperature, and the mixture was stirred at the same temperature for 15 minutes, and stirred at room temperature for 1 hour. The reaction mixture was poured into 0.5 mol/L hydrochloric acid, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=5/1-3/1) to give 3-(2,3,4,6-tetra-O-benzyl-β-D-glucopyranosyl)-1-(4-iodo-benzyl)-7-methyl-1H-indole (1.48 g). A mixture of 3-(2,3,4,6-tetra-O-benzyl-β-D-glucopyranosyl)-1-(4-iodobenzyl)-7-methyl-1H-indole (1.06 g), acrylic acid (0.18 g), palladium(II) acetate (14 mg), tris(2-methylphenyl)phosphine (37 mg), triethylamine (2 mL) and acetonitrile (2 mL) was stirred at 80° C. under an argon atmosphere overnight. The reaction mixture was diluted with diethyl ether, and the mixture was stirred at room temperature for 10 minutes. The insoluble material was removed by filtration, and the solvent was removed under reduced pressure. The residue was purified by column chromatography on silica gel (eluent: n-hexane/ethyl acetate=1/1-1/3) to give the title compound (0.85 g).

Example 165

Example 165 was prepared in a similar manner to that described in Example 164 using the corresponding starting material.

The structures and NMR spectrum data of the compounds of Examples 161 to 165 are described in Table 8.

TABLE 8

| No. | Structure | $^1$H-NMR (CDCl$_3$) δ ppm: |
|---|---|---|
| Example 161 | 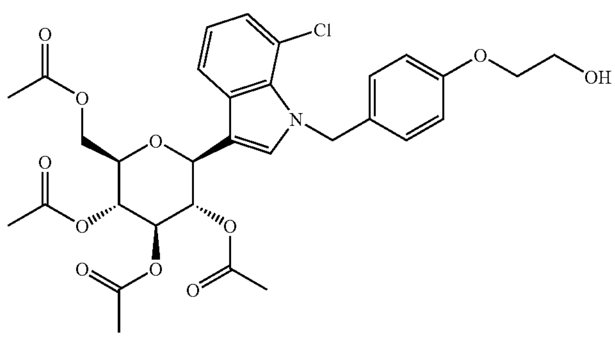 | 1.69 (3H, s), 1.96 (1H, t, J = 6.3 Hz), 2.01 (3H, s), 2.06 (3H, s), 2.07 (3H, s), 3.85-4.0 (3H, m), 4.0-4.1 (2H, m), 4.1-4.2 (1H, m), 4.25-4.35 (1H, m), 4.7-4.8 (1H, m), 5.15-5.4 (3H, m), 5.6-5.75 (2H, m), 6.8-6.9 (2H, m), 6.9-7.0 (2H, m), 7.0-7.2 (3H, m), 7.55-7.65 (1H, m) |
| Example 162 | 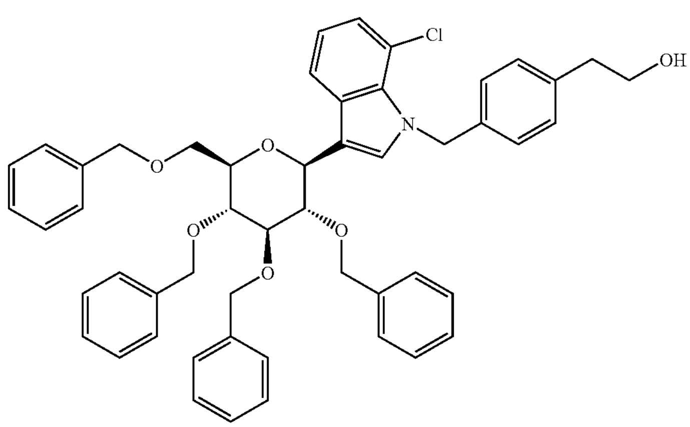 | 2.79 (2H, t, J = 6.4 Hz), 3.55-3.65 (1H, m), 3.7-3.95 (8H, m), 4.35 (1H, d, J = 10.7 Hz), 4.45-4.6 (2H, m), 4.6-4.7 (2H, m), 4.85-4.95 (3H, m), 5.66 (1H, d, J = 16.4 Hz), 5.72 (1H, d, J = 16.4 Hz), 6.75-6.85 (2H, m), 6.9-7.35 (25H, m), 7.7-7.8 (1H, m) |

TABLE 8-continued

| No. | Structure | $^1$H-NMR (CDCl$_3$) δ ppm: |
|---|---|---|
| Example 163 | 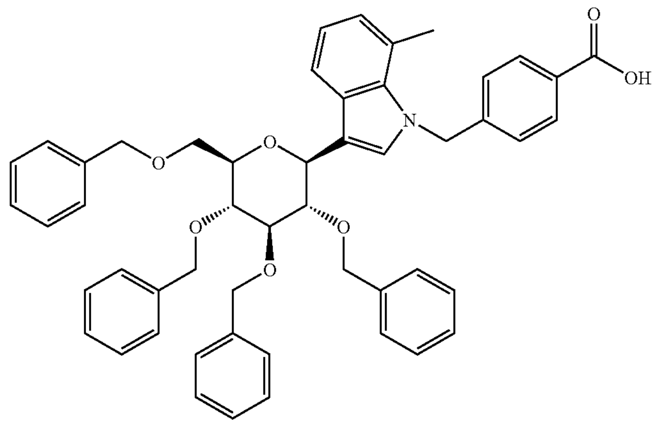 | 2.48 (3H, s), 3.6-3.7 (1H, m), 3.75-3.95 (6H, m), 4.4 (1H, d, J = 10.8 Hz), 4.5-4.6 (2H, m), 4.6-4.75 (2H, m), 4.85-5.0 (3H, m), 5.58 (2H, s), 6.85-6.95 (3H, m), 6.95-7.05 (3H, m), 7.05-7.4 (19H, m), 7.7-7.8 (1H, m), 7.8-7.9 (2H, m) |
| Example 164 | 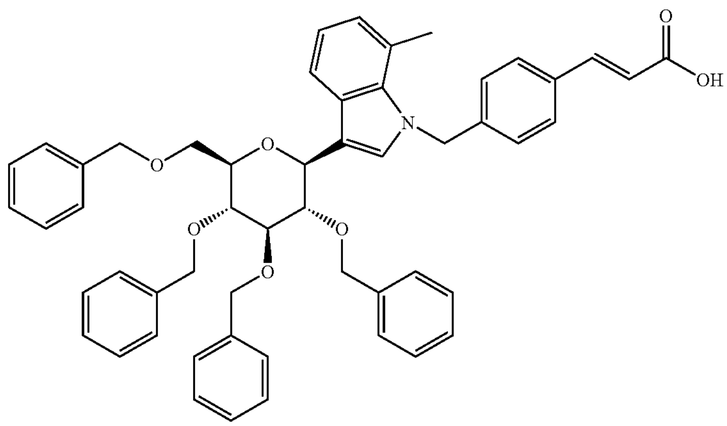 | 2.5 (3H, s), 3.6-3.7 (1H, m), 3.75-4.0 (6H, m), 4.39 (1H, d, J = 10.7 Hz), 4.5-4.75 (4H, m), 4.85-5.0 (3H, m), 5.5-5.6 (2H, m), 6.31 (1H, d, J = 16.3 Hz), 6.85-7.4 (27H, m), 7.65 (1H, d, J = 16.3 Hz), 7.7-7.8 (1H, m) |
| Example 165 | 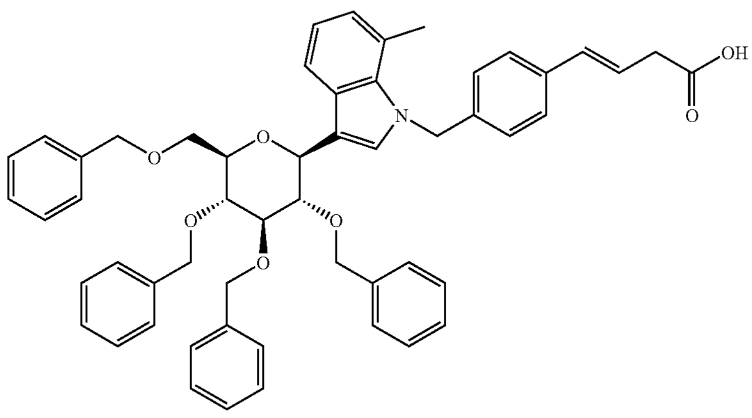 | 2.52 (3H, s), 3.2-3.3 (2H, m), 3.6-3.7 (1H, m), 3.75-3.95 (6H, m), 4.36 (1H, d, J = 11.0 Hz), 4.5-4.6 (2H, m), 4.6-4.75 (2H, m), 4.85-4.95 (3H, m), 5.45-5.55 (2H, m), 6.1-6.25 (1H, m), 6.35-6.45 (1H, m), 6.8-7.4 (27H, m), 7.7-7.75 (1H, m) |

Example 166

3-(β-D-Glucopyranosyl)-1-[4-(2-hydroxyethoxy)benzyl]-5-methyl-1H-indole

1-{4-[2-(Benzyloxy)ethoxy]benzyl}-3-(β-D-glucopyranosyl)-5-methyl-1H-indole (32 mg) was dissolved in a mixed solvent of methanol (1 mL) and ethyl acetate (2 mL). To the solution was added 10% palladium-carbon powder (10 mg), and the mixture was stirred at room temperature under a hydrogen atmosphere for 1 hour. The insoluble material was removed by filtration, and the solvent was removed under reduced pressure to give the title compound (17 mg).

Example 167

1-[4-(2-Aminoethoxy)benzyl]-7-chloro-3-(β-D-glucopyranosyl)-1H-indole

Step 1

To a solution of 3-(2,3,4,6-tetra-O-acetyl-β-D-glucopyranosyl)-7-chloro-1-[4-(2-hydroxyethoxy)benzyl]-1H-indole (0.23 g) and triethylamine (0.076 mL) in dichloromethane (4 mL) was added methanesulfonyl chloride (0.034 mL), and the mixture was stirred at room temperature for 1 hour. The reaction mixture was poured into 1 mol/L hydrochloric acid, and the resulting mixture was extracted with ethylacetate. The extract was washed with water and brine successively, and dried over anhydrous sodium sulfate. The solvent was removed under reduced pressure to give 3-(2,3,4,6-tetra-O-acetyl-β-D-glucopyranosyl)-7-chloro-1-{4-[2-(methanesulfonyloxy)ethoxy]-benzyl}-1H-indole (0.25 g).

Step 2

To a solution of 3-(2,3,4,6-tetra-O-acetyl-β-D-glucopyranosyl)-7-chloro-1-{4-[2-(methanesulfonyloxy)ethoxy]-benzyl}-1H-indole (85 mg) in N,N-dimethylformamide (2 mL) was added sodium azide (12 mg), and the mixture was stirred at 100° C. for 2 hours. The reaction mixture was poured into water, and the resulting mixture was extracted with diethyl ether. The extract was washed with water and brine successively, and dried over anhydrous sodium sulfate. The solvent was removed under reduced pressure. The residue was dissolved in a mixed solvent of methanol (2 mL) and tetra hydrofuran (3 mL). To the solution was added sodium methoxide (28% methanol solution, 0.30 mL), and the mixture was stirred at room temperature for 30 minutes. The reaction mixture was poured into a saturated aqueous sodium hydrogen carbonate solution, and the resulting mixture was extracted with ethylacetate. The extract was washed with brine, and dried over anhydrous sodium sulfate. The solvent was removed under reduced pressure. The residue was dissolved in tetra hydrofuran (3 mL). To the solution were added water (0.3 mL) and triphenylphosphine (36 mg), and the mixture was stirred at room temperature for 3 days. The solvent was removed under reduced pressure, and the residue was purified by preparative reverse phase column chromatography (Shiseido CAPCELL PAK C18 ODS, UG80, 5 μm, 20×50 mm, linear gradient water/methanol=90/10-10/90, flow rate 30 mL/min) to give the title compound (12 mg).

Example 168

7-Chloro-3-(β-D-glucopyranosyl)-1-{4-[2-(methylamino)-ethoxy]benzyl}-1H-indole 3-(2,3,4,6-Tetra-O-acetyl-β-D-glucopyranosyl)-7-chloro-1-{4-[2-(methanesulfonyloxy)ethoxy]benzyl}-1H-indole was prepared in a similar manner to that described in Step 1 of Example 167.

To a solution of 3-(2,3,4,6-tetra-O-acetyl-β-D-glucopyranosyl)-7-chloro-1-{4-[2-(methanesulfonyloxy)-ethoxy]benzyl}-1H-indole (85 mg) methanol (1 mL)-acetonitrile (1 mL) were added methylamine (40% methanol solution, 93 mg) and a catalytic amount of sodium iodide, and the mixture was stirred at 60° C. for 3 days. To the reaction mixture was added sodium methoxide (28% methanol solution, 0.092 mL) at room temperature, and the mixture was stirred at room temperature for 1 hour. The solvent was removed under reduced pressure, and the residue was purified by preparative reverse phase column chromatography (Shiseido CAPCELL PAK C18 ODS, UG80, 5 μm, 20×50 mm, linear gradient water/methanol=90/10-10/90, flow rate 30 mL/min) to give the title compound (11 mg).

Example 169

Example 169 was prepared in a similar manner to that described in Example 168 using the corresponding starting material.

Example 170

1-(4-Carboxybenzyl)-7-chloro-3-(β-D-glucopyranosyl)-1H-indole

To a solution of 7-chloro-3-(β-D-glucopyranosyl)-1-[4-(methoxycarbonyl)benzyl]-1H-indole (71 mg) in ethanol (1 mL) was added 2 mol/L aqueous sodium hydroxide solution (1 mL), and the mixture was stirred at room temperature for 2 hours. To the reaction mixture was added 2 mol/L hydrochloric acid (1 mL), and the solvent was removed under reduced pressure. The residue was purified by solid phase extraction on ODS (washing solvent: water, eluent: methanol) to give the title compound (68 mg).

Example 171

7-Chloro-3-(β-D-glucopyranosyl)-1-[4-(hydroxymethyl)-benzyl]-1H-indole

To a mixture of 1-(4-carboxybenzyl)-7-chloro-3-(β-D-glucopyranosyl)-1H-indole (68 mg), pyridine (0.11 mL) and dichloromethane (2 mL) were added acetic anhydride (0.13 mL) and 4-dimethylaminopyridine (2 mg), and the mixture was stirred at room temperature for 3 days. The reaction mixture was poured into 0.5 mol/L hydrochloric acid, and the resulting mixture was extracted with ethylacetate. The extract was washed with water and brine successively, and dried over anhydrous sodium sulfate. The solvent was removed under reduced pressure. The residue was washed with a mixed solvent of n-hexane and ethyl acetate (2/1), and dried under reduced pressure to give 3-(2,3,4,6-tetra-O-acetyl-β-D-glucopyranosyl)-1-(4-carboxybenzyl)-7-chloro-1H-indole (78 mg). This material was dissolved in tetra hydrofuran (5 mL). To the solution was added borane dimethylsulfide complex (0.018 mL) under ice-cooling, and the mixture was stirred at room temperature for 2 hours. To the reaction mixture was added 20% aqueous potassium carbonate solution under ice-cooling, and the resulting mixture was extracted with ethyl acetate. The extract was washed with brine, and dried over anhydrous sodium sulfate. The solvent was removed under reduced pressure. The residue was dissolved in a mixed solvent of methanol (3 mL) and tetra hydrofuran (3 mL). To the solution was added sodium methoxide (28% methanol solution, 0.040 mL), and the mixture was stirred at room temperature for 1 hour. The reaction mixture was purified by column chromatography on amino-propylated silica gel (eluent: methanol) and preparative reverse phase column chromatography (Shiseido CAPCELL PAK C18 ODS, UG80, 5 μm, 20×50 mm, linear gradient water/methanol=90/10-10/90, flow rate 30 mL/min) successively to give the title compound (34 mg).

Example 172

7-Chloro-3-(β-D-glucopyranosyl)-1-[4-(2-methoxyethyl)-benzyl]-1H-indole

To a solution of 3-(2,3,4,6-tetra-O-benzyl-β-D-glucopyranosyl)-7-chloro-1-[4-(2-hydroxyethyl)benzyl]-1H-indole (0.13 g) in N,N-dimethylformamide (3 mL) was added 55% sodium hydride (9 mg) under ice-cooling, and the mixture was stirred at the same temperature for 15 minutes. To this mixture was added a solution of methyl iodide (0.020 mL) in tetra hydrofuran (1 mL) at the same temperature, and the mixture was stirred at the same temperature for 15 minutes, and stirred at room temperature for 1 hour. The reaction mixture was poured into water, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=4/1) to give 3-(2,3,4,6-tetra-O-benzyl-β-D-glucopyranosyl)-7-chloro-1-[4-(2-methoxy-ethyl)benzyl]-1H-indole (0.13 g). This material was dissolved in a mixed solvent of methanol (1 mL) and ethyl acetate (4 mL). To the solution was added 10% palladium-carbon powder (60 mg), and the mixture was stirred at room temperature under a hydrogen atmosphere for 30 minutes. To the reaction mixture was added sodium hydrogen carbonate (200 mg), and the mixture was stirred at room temperature for 10 minutes. The insoluble material was removed by filtration, and the solvent was removed under reduced pressure. The residue was purified by preparative reverse phase column chromatography (Shiseido CAPCELL PAK C18 ODS, UG80, 5 μm, 20×50 mm, linear gradient water/methanol=90/10-10/90, flow rate 30 mL/min) to give the title compound (39 mg).

Example 173

Example 173 was prepared in a similar manner to that described in Example 172 using the corresponding starting material.

Example 174

7-Chloro-3-(β-D-glucopyranosyl)-1-[4-(3-hydroxypropyl)-benzyl]-1H-indole 3-(2,3,4,6-Tetra-O-benzyl-β-D-glucopyranosyl)-7-chloro-1-[4-(3-hydroxypropyl)benzyl]-1H-indole was prepared in a similar manner to that described in Example 162 using the corresponding starting material. The title compound was prepared in a similar manner to that described in Example 166 using this material instead of 1-{4-[2-(benzyloxy)ethoxy]-benzyl}-3-(β-D-glucopyranosyl)-5-methyl-1H-indole.

Examples 175 to 178

Examples 175 to 178 were prepared in a similar manner to that described in Example 174 using the corresponding starting materials.

The structures and NMR spectrum data of the compounds of Examples 166 to 178 are described in Table 9.

TABLE 9

| No. | Structure | $^1$H-NMR (CD$_3$OD) δ ppm: |
|---|---|---|
| Example 166 | 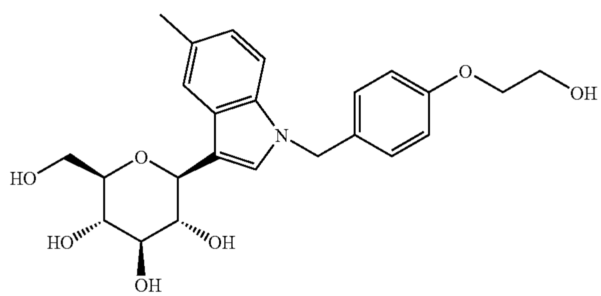 | 2.39 (3H, s), 3.4-3.55 (3H, m), 3.65-3.95 (5H, m), 3.95-4.05 (2H, m), 4.45 (1H, d, J = 10.0 Hz), 5.23 (2H, s), 6.8-6.9 (2H, m), 6.9-7.0 (1H, m), 7.05 7.15 (2H, m), 7.15-7.25 (1H, m), 7.28 (1H, s), 7.45-7.55 (1H, m) |
| Example 167 | 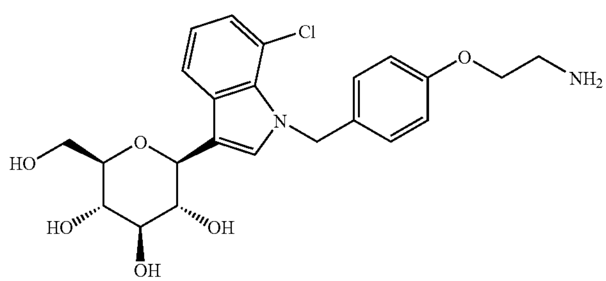 | 2.97 (2H, t, J = 5.3 Hz), 3.4-3.55 (3H, m), 3.6-3.75 (2H, m), 3.85-3.95 (1H, m), 3.96 (2H, t, J = 5.3 Hz), 4.48 (1H, d, J = 9.7 Hz), 5.65-5.75 (2H, m), 6.8-6.9 (2H, m), 6.95-7.15 (4H, m), 7.35 (1H, s), 7.65-7.75 (1H, m) |
| Example 168 | 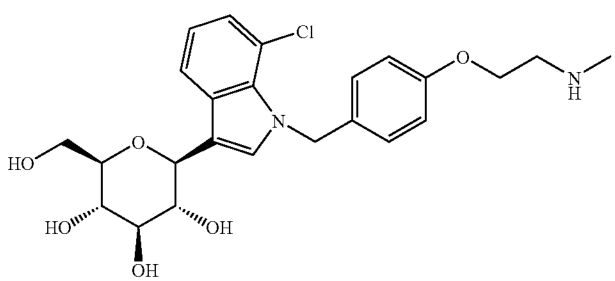 | 2.41 (3H, s), 2.89 (2H, t, J = 5.1 Hz), 3.4-3.55 (3H, m), 3.6-3.75 (2H, m), 3.85-3.95 (1H, m), 4.02 (2H, t, J = 5.1 Hz), 4.48 (1H, d, J = 9.3 Hz), 5.6-5.75 (2H, m), 6.8-6.9 (2H, m), 6.95-7.15 (4H, m), 7.34 (1H, s), 7.65-7.75 (1H, m) |

TABLE 9-continued

| No. | Structure | $^1$H-NMR (CD$_3$OD) δ ppm: |
|---|---|---|
| Example 169 | 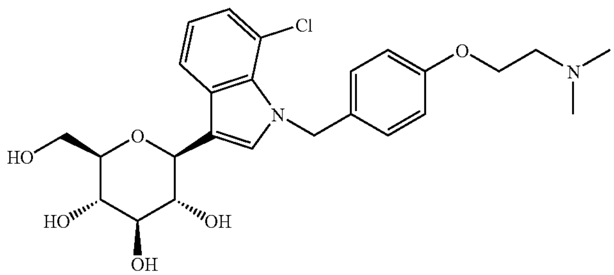 | 2.3 (6H, s), 2.71 (2H, t, J = 5.4 Hz), 3.4-3.55 (3H, m), 3.6-3.75 (2H, m), 3.85-3.95 (1H, m), 4.03 (2H, t, J = 5.4 Hz), 4.48 (1H, d, J = 9.9Hz), 5.6-5.75 (2H, m), 6.8-6.9 (2H, m), 6.95-7.15 (4H, m), 7.34 (1H, s), 7.65-7.75 (1H, m) |
| Example 170 | 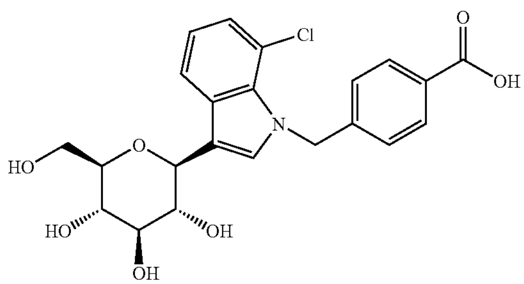 | 3.4-3.55 (3H, m), 3.65-3.75 (2H, m), 3.85-3.95 (1H, m), 4.51 (1H, d, J = 9.3 Hz), 5.84 (2H, s), 6.95-7.05 (1H, m), 7.05-7.15 (3H, m), 7.4 (1H, s), 7.7-7.75 (1H, m), 7.85-7.95 (2H, m) |
| Example 171 | 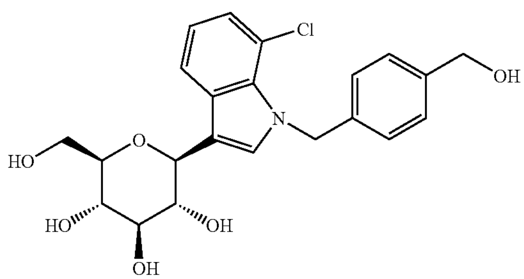 | 3.4-3.55 (3H, m), 3.65-3.75 (2H, m), 3.85-3.95 (1H, m), 4.49 (1H, d, J = 9.7 Hz), 4.54 (2H, s), 5.7-5.85 (2H, m), 6.95-7.1 (4H, m), 7.2-7.3 (2H, m), 7.37 (1H, s), 7.65-7.75 (1H, m) |
| Example 172 | 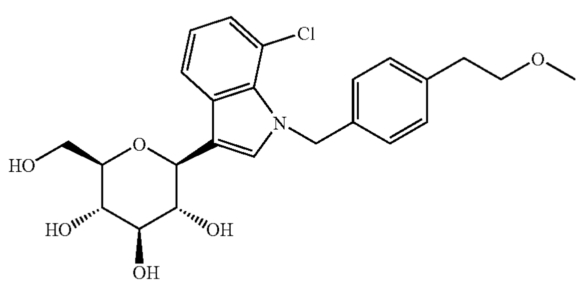 | 2.8 (2H, t, J = 6.8 Hz), 3.25-3.6 (8H, m), 3.6-3.75 (2H, m), 3.85-3.95 (1H, m), 4.49 (1H, d, J = 9.3 Hz), 5.65-5.8 (2H, m), 6.9-7.05 (3H, m), 7.05-7.2 (3H, m), 7.35 (1H, s), 7.65-7.75 (1H, m) |
| Example 173 | 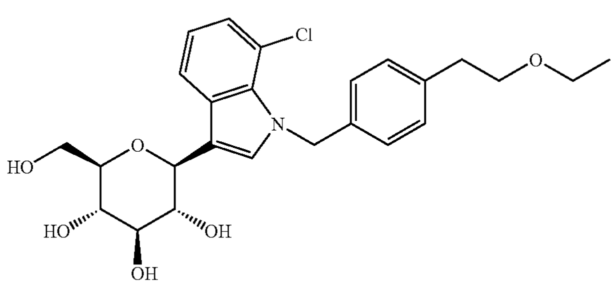 | 1.13 (3H, t, J = 6.9 Hz), 2.8 (2H, t, J = 6.9 Hz), 3.4-3.55 (5H, m), 3.59 (2H, t, J = 6.9 Hz), 3.65-3.75 (2H, m), 3.85-3.95 (1H, m), 4.49 (1H, d, J = 9.4 Hz), 5.65-5.8 (2H, m), 6.9-7.05 (3H, m), 7.05-7.2 (3H, m), 7.35 (1H, s), 7.65-7.75 (1H, m) |

TABLE 9-continued

| No. | Structure | $^1$H-NMR (CD$_3$OD) δ ppm: |
|---|---|---|
| Example 174 | 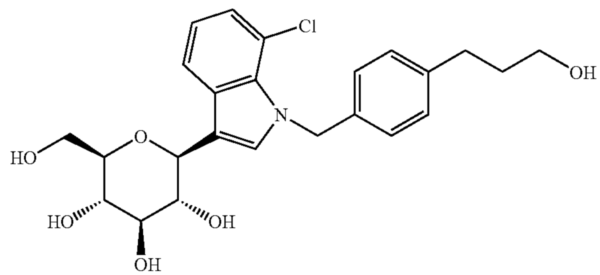 | 1.7-1.85 (2H, m), 2.61 (2H, t, J = 7.7 Hz), 3.4-3.6 (5H, m), 3.65-3.75 (2H, m), 3.85-3.95 (1H, m), 4.49 (1H, d, J = 9.3 Hz), 5.65-5.8 (2H, m), 6.9-7.15 (6H, m), 7.35 (1H, s), 7.65-7.75 (1H, m) |
| Example 175 | 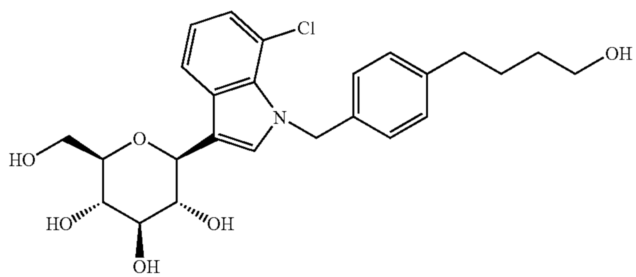 | 1.45-1.7 (4H, m), 2.57 (2H, t, J = 7.6 Hz), 3.4-3.6 (5H, m), 3.65-3.75 (2H, m), 3.85-3.95 (1H, m), 4.49 (1H, d, J = 9.8 Hz), 5.65-5.8 (2H, m), 6.9-7.15 (6H, m), 7.34 (1H, s), 7.65-7.75 (1H, m) |
| Example 176 | 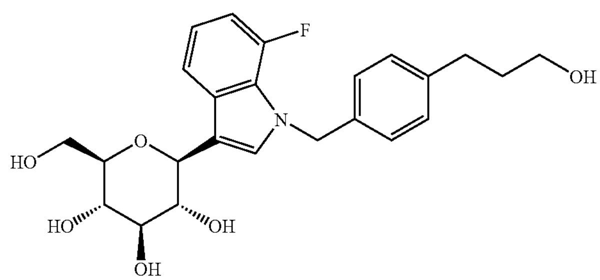 | 1.7-1.85 (2H, m), 2.62 (2H, t, J = 7.7 Hz), 3.4-3.6 (5H, m), 3.65-3.75 (2H, m), 3.85-3.95 (1H, m), 4.46 (1H, d, J = 9.9 Hz), 5.44 (2H, s), 6.75-6.85 (1H, m), 6.9-7.0 (1H, m), 7.05-7.15 (4H, m), 7.34 (1H, s), 7.45-7.55 (1H, m) |
| Example 177 | 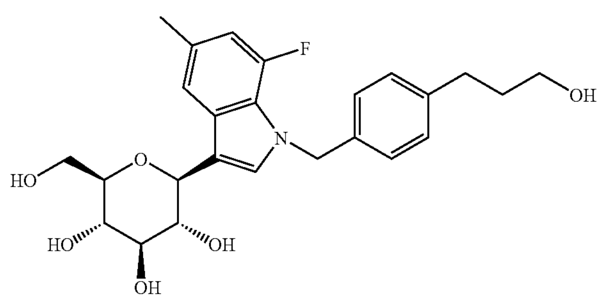 | 1.7-1.85 (2H, m), 2.38 (3H, s), 2.62 (2H, t, J = 7.8 Hz), 3.4-3.6 (5H, m), 3.65-3.75 (2H, m), 3.85-3.95 (1H, m), 4.43 (1H, d, J = 9.5 Hz), 5.35 5.45 (2H, m), 6.6-6.7 (1H, m), 7.0-7.15 (4H, m), 7.25-7.35 (2H, m) |
| Example 178 | 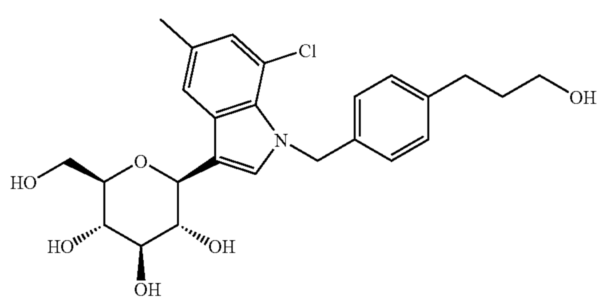 | 1.7-1.85 (2H, m), 2.37 (3H, s), 2.61 (2H, t, J = 7.8 Hz), 3.4-3.6 (5H, m), 3.65-3.75 (2H, m), 3.85-3.95 (1H, m), 4.45 (1H, d, J = 9.3 Hz), 5.6-5.75 (2H, m), 6.9-7.0 (3H, m), 7.05-7.15 (2H, m), 7.3 (1H, s), 7.45-7.5 (1H, m) |

Examples 179 and 180

Examples 179 and 180 were prepared in a similar manner to that described in Example 166 using the corresponding starting materials.

Example 181

3-(β-D-Glucopyranosyl)-1-[4-(2-hydroxyethoxycarbonyl)-benzyl]-7-methyl-1H-indole A suspension of 3-(2,3,4,6-tetra-O-benzyl-β-D-glucopyranosyl)-1-(4-carboxybenzyl)-7-methyl-1H-indole (90 mg), benzyl 2-bromoethyl ether (37 mg), cesium carbonate (74 mg) and sodium iodide (3 mg) in N,N-dimethylformamide (1 mL) was stirred at room temperature for 1 day. The reaction mixture was poured into 0.5 mol/L hydrochloric acid, and the resulting mixture was extracted with ethylacetate. The extract was washed with water and brine successively, and dried over anhydrous sodium sulfate. The solvent was removed under reduced pressure, and the residue was purified by column chromatography on silica gel (eluent: n-hexane/ethyl acetate=3/1-3/2) to give 3-(2,3,4,6-tetra-O-benzyl-β-D-glucopyranosyl)-1-{4-[2-(benzyloxy)ethoxycarbonyl]benzyl}-7-methyl-1H-indole (0.10 g). This material was dissolved in a mixed solvent of methanol (2 mL) and tetra hydrofuran (2 mL). To the solution was added 10% palladium-carbon powder (50 mg), and the mixture was stirred at room temperature under a hydrogen atmosphere for 4 hours. The insoluble material was removed by filtration, and the solvent was removed under reduced pressure. The residue was purified by column chromatography on silica gel (eluent: dichloromethane/methanol=8/1-5/1) to give the title compound (42 mg).

Examples 182 to 184

Examples 182 to 184 were prepared in a similar manner to that described in Example 181 using the corresponding starting materials.

Example 185

3-(β-D-Glucopyranosyl)-1-{4-[3-(2-hydroxyethoxycarbonyl)-propyl]benzyl}-7-methyl-1H-indole To a mixture of 3-(2,3,4,6-tetra-O-benzyl-β-D-glucopyranosyl)-1-[4-((1E)-3-carboxyprop-1-enyl)benzyl]-7-methyl-1H-indole (0.10 g), 2-(benzyloxy)ethanol (22 mg), 4-dimethylaminopyridine (7 mg) and dichloromethane (0.5 mL) was added dicyclohexylcarbodiimide (37 mg), and the mixture was stirred at room temperature overnight. The reaction mixture was directly purified by column chromatography on silica gel (eluent: n-hexane/ethylacetate=4/1-2/1) to give 3-(2,3,4,6-tetra-O-benzyl-β-D-glucopyranosyl)-1-(4-{(1E)-3-[2-(benzyl-oxy)ethoxycarbonyl]prop-1-enyl}benzyl)-7-methyl-1H-indole (48 mg). This material was dissolved in a mixed solvent of methanol (1 mL) and tetra hydrofuran (1 mL). To the solution was added 10% palladium-carbon powder (50 mg), and the mixture was stirred at room temperature under a hydrogen atmosphere for 4 hours. The insoluble material was removed by filtration, and the solvent was removed under reduced pressure. The residue was purified by column chromatography on silica gel (eluent: dichloromethane/methanol=12/1-8/1) to give the title compound (14 mg).

Example 186

3-(β-D-Glucopyranosyl)-1-{4-[3-((S)-2,3-dihydroxypropoxy-carbonyl)propyl]benzyl}-7-methyl-1H-indole To a mixture of 3-(2,3,4,6-tetra-O-benzyl-β-D-glucopyranosyl)-1-[4-((1E)-3-carboxyprop-1-enyl)benzyl]-7-methyl-1H-indole (0.30 g), (R)-(−)-2,2-dimethyl-1,3-dioxolane-4-methanol (62 mg), 4-dimethylaminopyridine (22 mg) and dichloromethane (1 mL) was added dicyclohexylcarbodiimide (0.11 g), and the mixture was stirred at room temperature overnight. The reaction mixture was directly purified by column chromatography on silica gel (eluent: n-hexane/ethyl acetate=3/1-3/2) to give 3-(2,3,4,6-tetra-O-benzyl-β-D-gluco-pyranosyl)-1-(4-{(1E)-3-[((S)-2,2-dimethyl-1,3-dioxolan-4-yl)methoxycarbonyl]prop-1-enyl}benzyl)-7-methyl-1H-indole (0.23 g). To a suspension of this material in dichloromethane (2 mL)-methanol (4 mL) was added Amberlyst 15 (0.40 g), and the mixture was stirred at 50° C. for 4 hours. The insoluble material was removed by filtration, and the solvent was removed under reduced pressure. The residue was purified by column chromatography on silica gel (eluent: n-hexane/ethyl acetate=1/2-1/4) to give 3-(2,3,4,6-tetra-O-benzyl-β-D-gluco-pyranosyl)-1-{4-[(1E)-3-((S)-2,3-dihydroxypropoxycarbonyl)-prop-1-enyl]benzyl}-7-methyl-1H-indole (0.12 g). This material was dissolved in a mixed solvent of methanol (2 mL) and tetra hydrofuran (2 mL). To the solution was added 10% palladium-carbon powder (0.10 g), and the mixture was stirred at room temperature under a hydrogen atmosphere for 4 hours. The insoluble material was removed by filtration, and the solvent was removed under reduced pressure. The residue was purified by column chromatography on silica gel (eluent: dichloromethane/methanol=8/1-5/1) to give the title compound (58 mg).

Example 187

Example 187 was prepared in a similar manner to that described in Example 186 using the corresponding starting material.

Example 188

3-(β-D-Glucopyranosyl)-1-[4-(3-{1-[(4-isopropylpiperazin-1-yl)carbonyl]-1-(methyl) ethylcarbamoyl}propyl)benzyl]-7-methyl-1H-indole A suspension of 3-(2,3,4,6-tetra-O-benzyl-β-D-glucopyranosyl)-1-[4-((1E)-3-carboxyprop-1-enyl)benzyl]-7-methyl-1H-indole (0.10 g), 1-(2-amino-2-methylpropionyl)-4-isopropylpiperazine (31 mg), 1-hydroxybenzotriazole (18 mg), 1-ethyl-3-(3-dimethylaminopropyl)carbodiimide hydrochloride (35 mg) and triethylamine (0.034 mL) in N,N-dimethylformamide (2 mL) was stirred at 50° C. overnight. The reaction mixture was poured into water, and the resulting mixture was extracted with ethyl acetate. The extract was washed with an aqueous potassium carbonate solution and brine successively, and dried over anhydrous sodium sulfate. The solvent was removed under reduced pressure, and the residue was purified by column chromatography on silica gel (eluent: dichloromethane/methanol=20/1-12/1) to give 3-(2,3,4,6-tetra-O-benzyl-β-D-glucopyranosyl)-1-[4-((1E)-3-{1-[(4-isopropylpiperazin-1-yl)carbonyl]-1-(methyl) ethylcarbamoyl}prop-1-enyl)benzyl]-7-methyl-1H-indole (0.11 g). This material was dissolved in a mixed solvent of methanol (3 mL) and tetra hydrofuran (3 mL). To the solution was added 10% palladium-carbon powder (0.50 g), and the mixture was stirred at room temperature under a hydrogen atmosphere for 4 hours. The insoluble material was removed by filtration, and the solvent was removed under reduced pressure. The residue was purified by column chromatography on silica gel (eluent: dichloromethane/methanol=5/1-3/1) to give the title compound (19 mg).

The structures and NMR spectrum data of the compounds of Examples 179 to 188 are described in Table 10.

TABLE 10

| No. | Structure | $^1$H-NMR (CD$_3$OD) δ ppm: |
|---|---|---|
| Example 179 | 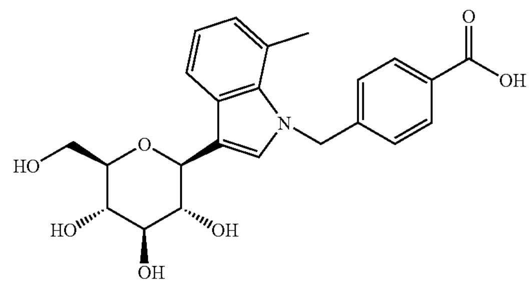 | 2.43 (3H, s), 3.4-3.55 (3H, m), 3.65-3.8 (2H, m), 3.85-3.95 (1H, m), 4.51 (1H, d, J = 9.7 Hz), 5.68 (2H, s), 6.8-6.85 (1H, m), 6.9-7.05 (3H, m), 7.3 (1H, s), 7.55-7.65 (1H, m), 7.85-7.95 (2H, m) |
| Example 180 | 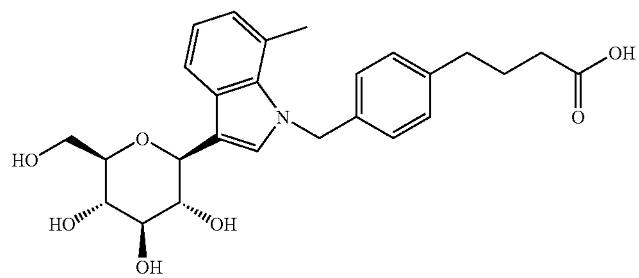 | 1.8-1.9 (2H, m), 2.23 (2H, t, J = 7.3 Hz), 2.46 (3H, s), 2.59 (2H, t, J = 7.6 Hz), 3.4-3.55 (3H, m), 3.65-3.8 (2H, m), 3.85-3.95 (1H, m), 4.5 (1H, d, J = 9.8 Hz), 5.58 (2H, s), 6.75-6.95 (4H, m), 7.05-7.15 (2H, m), 7.27 (1H, s), 7.55-7.65 (1H, m) |
| Example 181 | 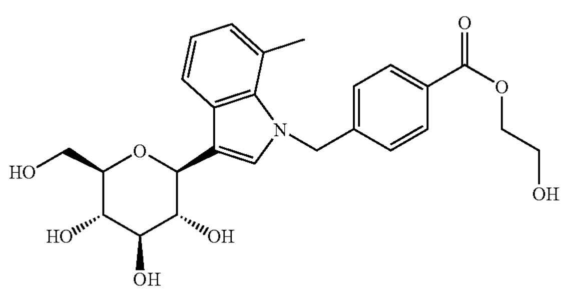 | 2.42 (3H, s), 3.4-3.55 (3H, m), 3.65-3.95 (5H, m), 4.34 (2H, t, J = 4.8 Hz), 4.51 (1H, d, J = 9.5 Hz), 5.7 (2H, s), 6.75-6.85 (1H, m), 6.85-7.05 (3H, m), 7.31 (1H, s), 7.55-7.65 (1H, m), 7.9-8.0 (2H, m) |
| Example 182 | 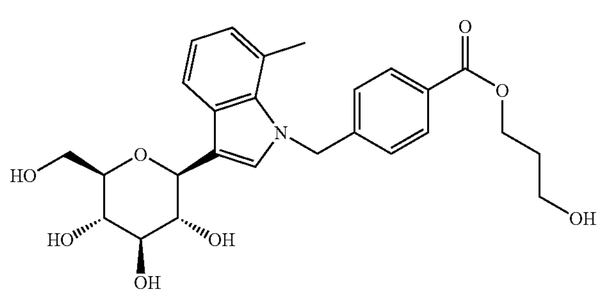 | 1.9-2.0 (2H, m), 2.42 (3H, s), 3.4-3.55 (3H, m), 3.65-3.8 (4H, m), 3.85-3.95 (1H, m), 4.37 (2H, t, J = 6.2 Hz), 4.51 (1H, d, J = 9.6 Hz), 5.69 (2H, s), 6.75-6.85 (1H, m), 6.9-7.05 (3H, m), 7.3 (1H, s), 7.55-7.65 (1H, m), 7.85-7.95 (2H, m) |
| Example 183 | 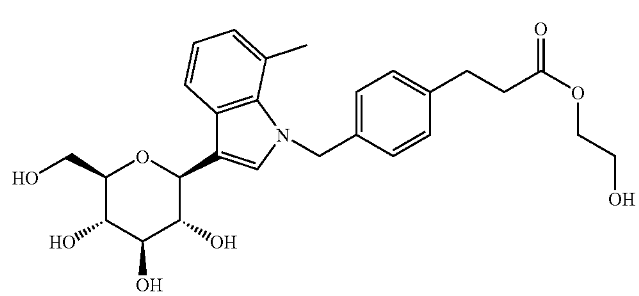 | 2.46 (3H, s), 2.61 (2H, t, J = 7.7 Hz), 2.88 (2H, t, J = 7.7 Hz), 3.4-3.55 (3H, m), 3.6-3.8 (4H, m), 3.85-3.95 (1H, m), 4.05-4.15 (2H, m), 4.5 (1H, d, J = 9.7 Hz), 5.58 (2H, s), 6.75-6.95 (4H, m), 7.1-7.15 (2H, m), 7.26 (1H, s), 7.55-7.65 (1H, m) |

TABLE 10-continued

| No. | Structure | $^1$H-NMR (CD$_3$OD) δ ppm: |
|---|---|---|
| Example 184 | 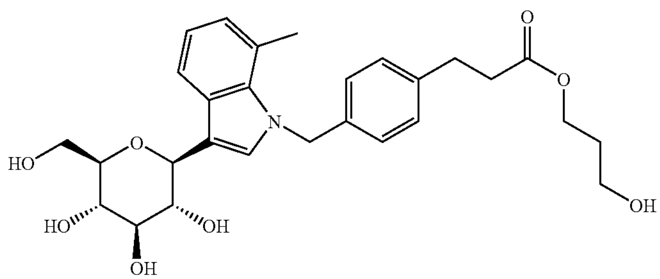 | 1.7-1.8 (2H, m), 2.46 (3H, s), 2.58 (2H, t, J = 7.4 Hz), 2.86 (2H, t, J = 7.4 Hz), 3.4-3.6 (5H, m), 3.65-3.8 (2H, m), 3.85-3.95 (1H, m), 4.1 (2H, t, J = 6.3 Hz), 4.5 (1H, d, J = 9.5 Hz), 5.58 (2H, s), 6.75-6.95 (4H, m), 7.05-7.15 (2H, m), 7.27 (1H, s), 7.55-7.65 (1H, m) |
| Example 185 | 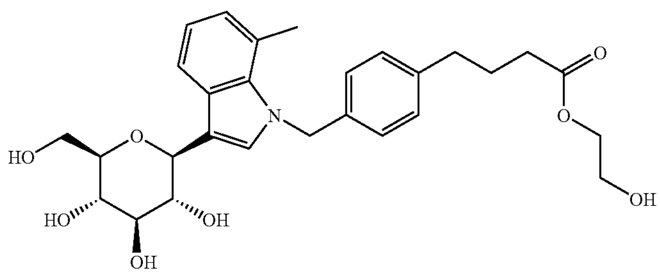 | 1.8-1.95 (2H, m), 2.32 (2H, t, J = 7.3 Hz), 2.47 (3H, s), 2.6 (2H, t, J = 7.5 Hz), 3.4-3.55 (3H, m), 3.65-3.8 (4H, m), 3.85-3.95 (1H, m), 4.05-4.15 (2H, m), 4.5 (1H, d, J = 9.6 Hz), 5.57 (2H, s), 6.75-6.95 (4H, m), 7.05-7.15 (2H, m), 7.27 (1H, s), 7.55-7.65 (1H, m) |
| Example 186 | 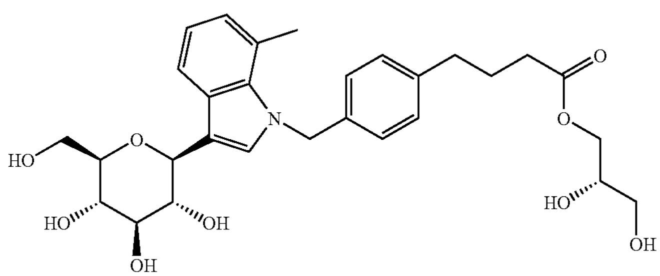 | 1.8-1.95 (2H, m), 2.32 (2H, t, J = 7.4 Hz), 2.47 (3H, s), 2.6 (2H, t, J = 7.3 Hz), 3.4-3.55 (5H, m), 3.6-3.85 (3H, m), 3.85-3.95 (1H, m), 4.02 (1H, dd, J = 11.4, 6.0 Hz), 4.11 (1H, dd, J = 11.4, 4.6 Hz), 4.5 (1H, d, J = 9.8 Hz), 5.58 (2H, s), 6.75-6.95 (4H, m), 7.05-7.15 (2H, m), 7.27 (1H, s), 7.55-7.65 (1H, m) |
| Example 187 | 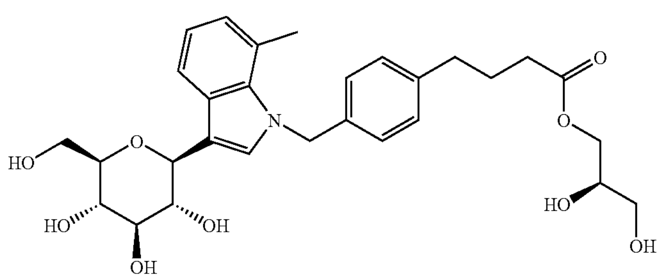 | 1.8-1.95 (2H, m), 2.32 (2H, t, J = 7.3 Hz), 2.47 (3H, s), 2.6 (2H, t, J = 7.6 Hz), 3.4-3.55 (5H, m), 3.6-3.85 (3H, m), 3.85-3.95 (1H, m), 4.02 (1H, dd, J = 11.5, 6.0 Hz), 4.11 (1H, dd, J = 11.5, 4.0 Hz), 4.5 (1H, d, J = 10.0 Hz), 5.58 (2H, s), 6.75-6.95 (4H, m), 7.05-7.15 (2H, m), 7.27 (1H, s), 7.55-7.65 (1H, m) |
| Example 188 | 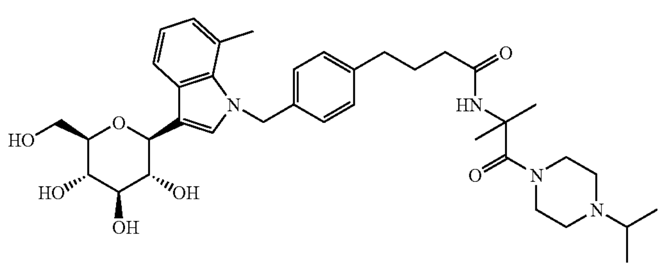 | 1.02 (6H, d, J = 6.9 Hz), 1.41 (6H, s), 1.75-1.9 (2H, m), 2.16 (2H, t, J = 7.5 Hz), 2.4-2.7 (10H, m), 3.4-3.55 (3H, m), 3.55-3.8 (6H, m), 3.85-3.95 (1H, m), 4.5 (1H, d, J = 9.6 Hz), 5.57 (2H, s), 6.75-6.95 (4H, m), 7.05-7.15 (2H, m), 7.26 (1H, s), 7.55-7.65 (1H, m) |

The following compounds can be prepared in a similar manner to that described above.
TABLE 11
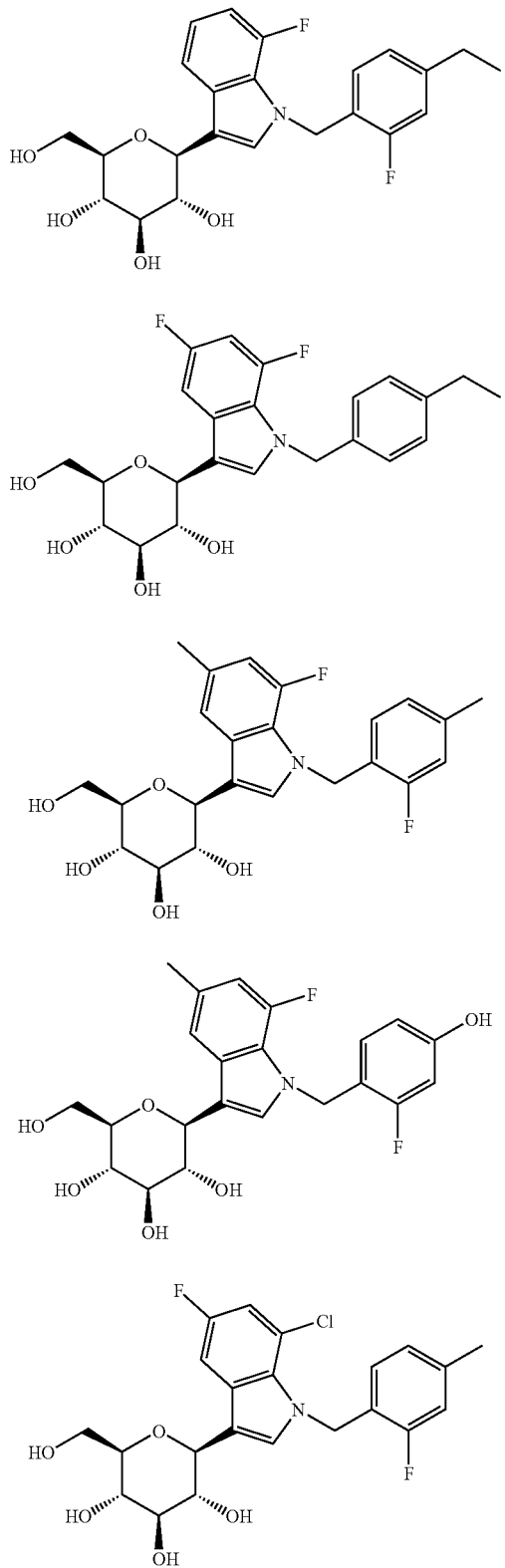

TABLE 11-continued
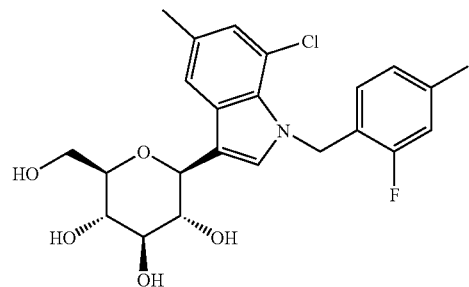
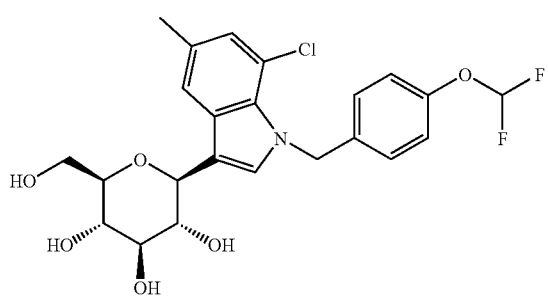
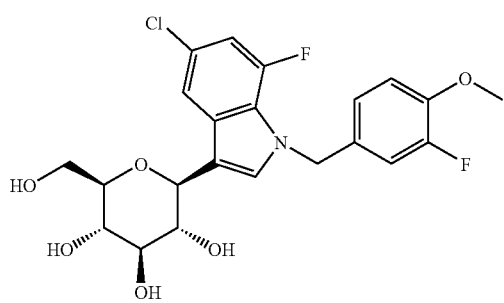
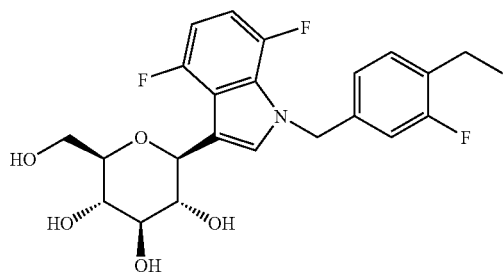
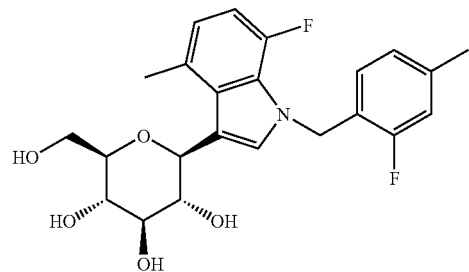

TABLE 11-continued
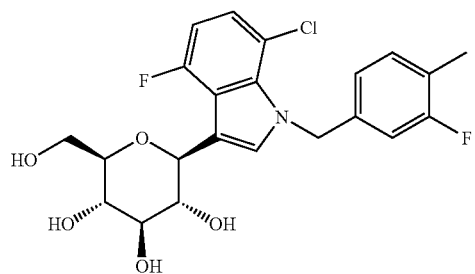
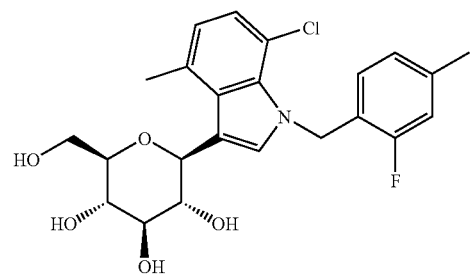
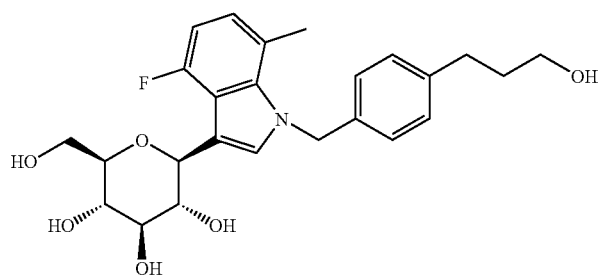
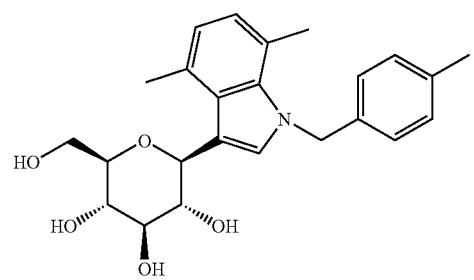
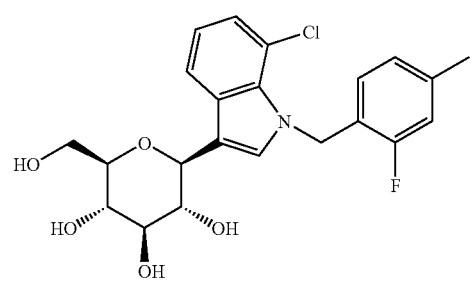

TABLE 11-continued
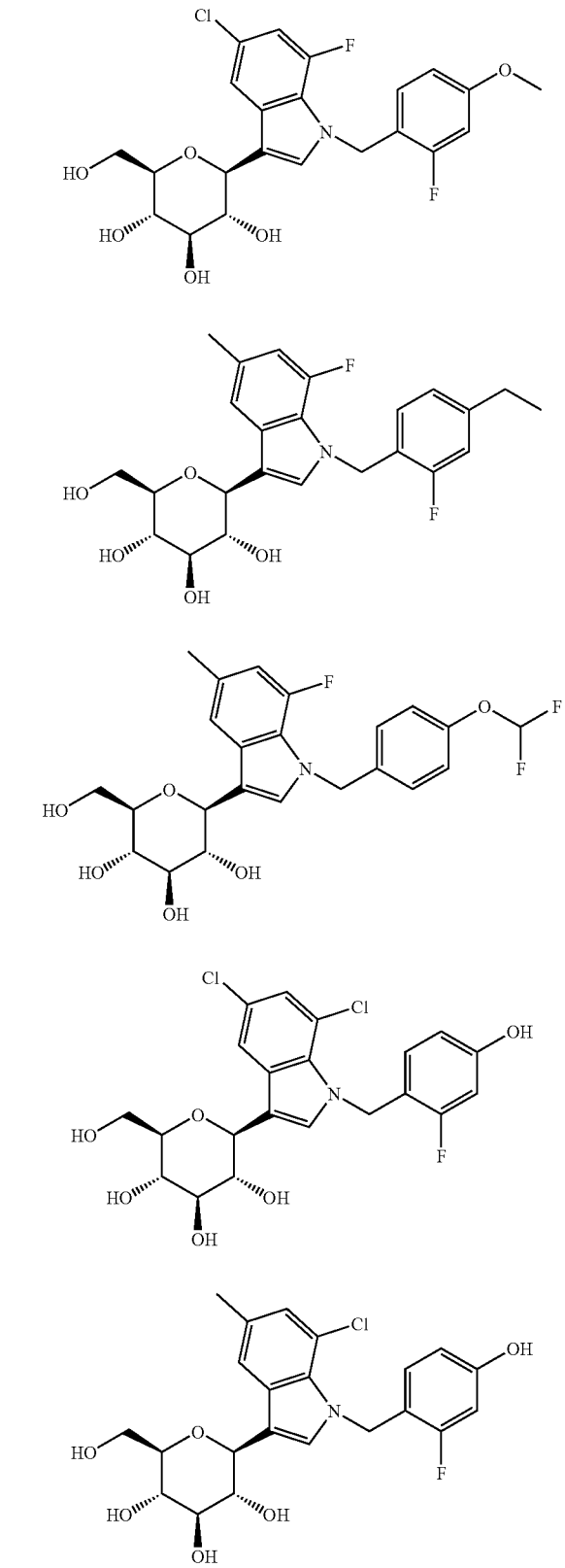

TABLE 11-continued
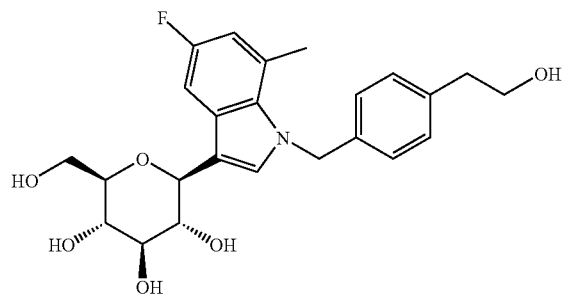
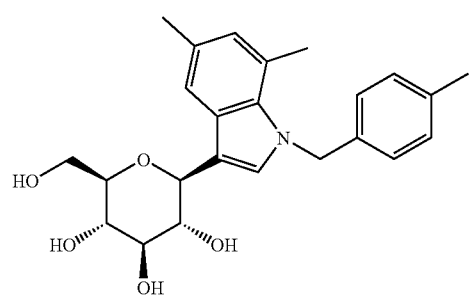
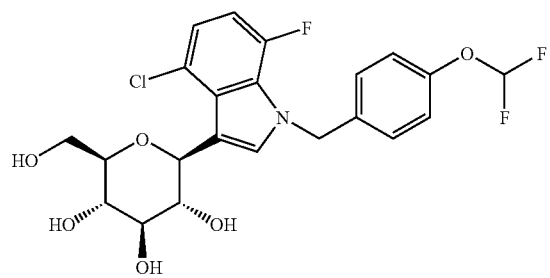
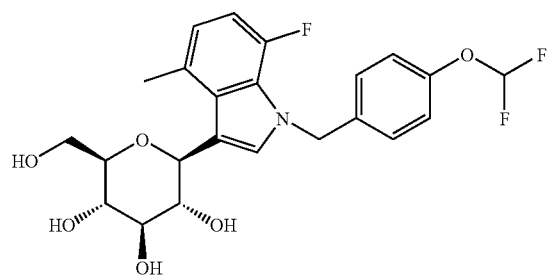
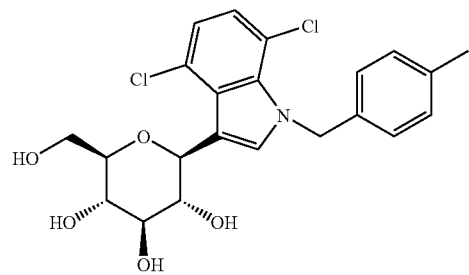

TABLE 11-continued
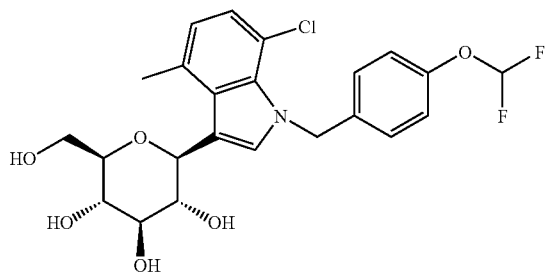
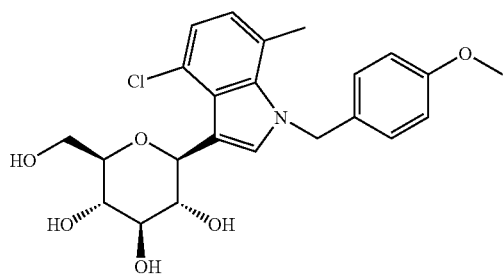
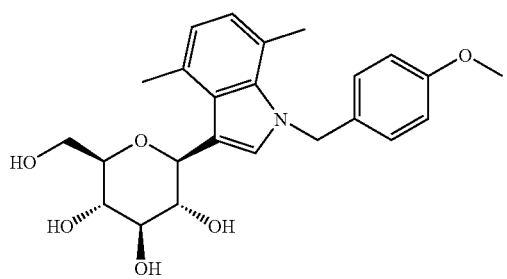
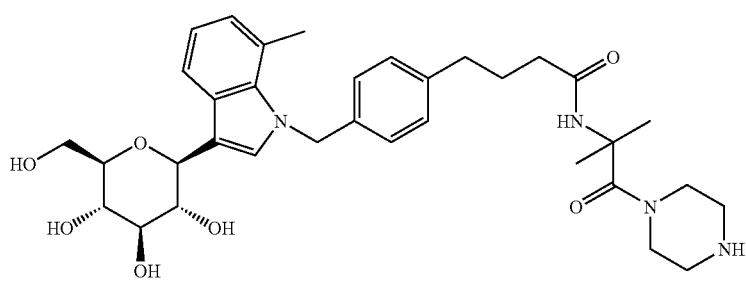
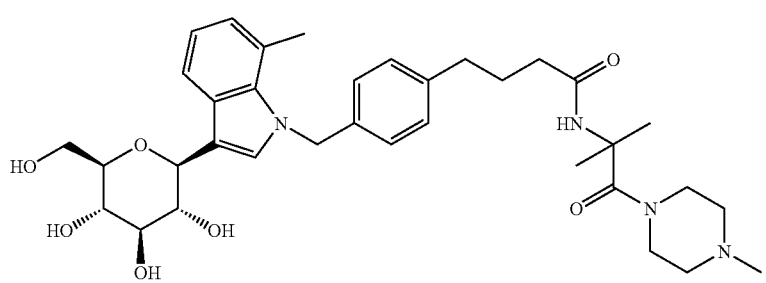

TABLE 11-continued
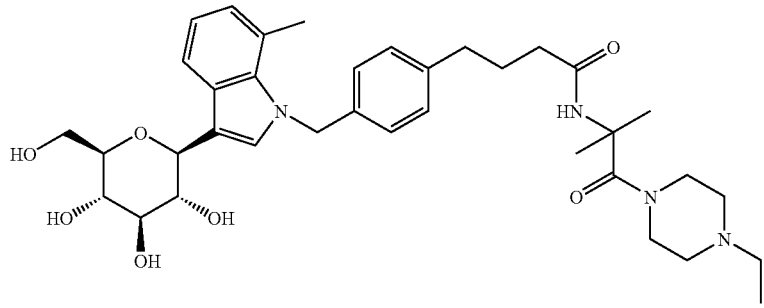
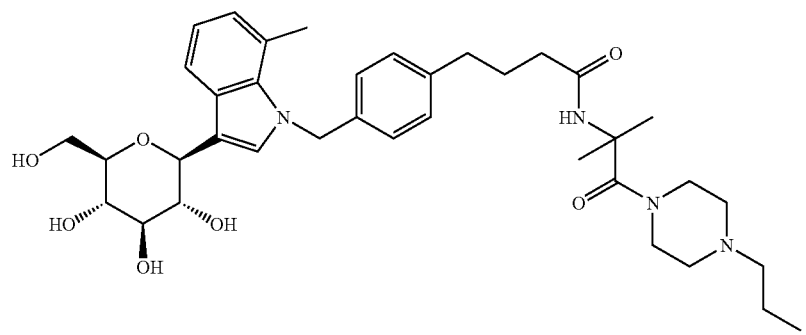
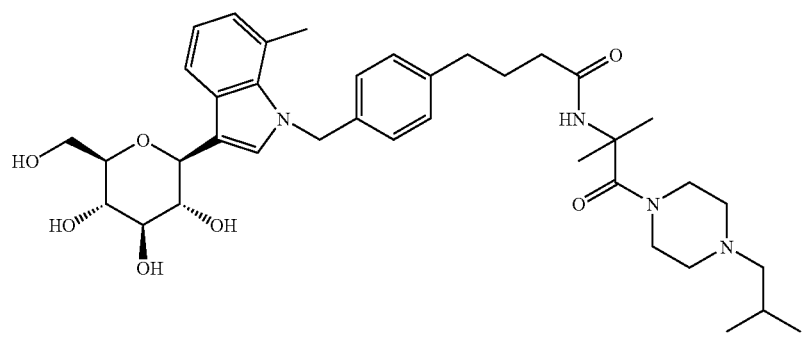
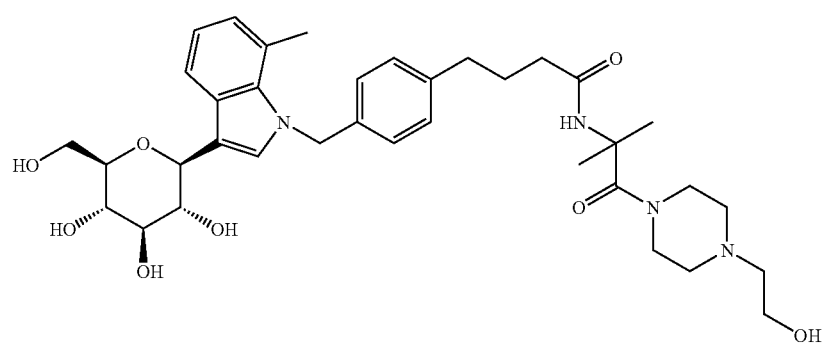
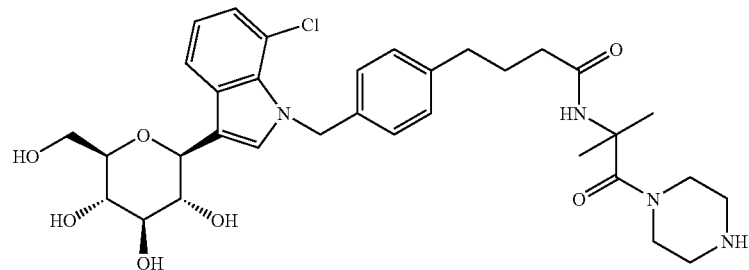

TABLE 11-continued
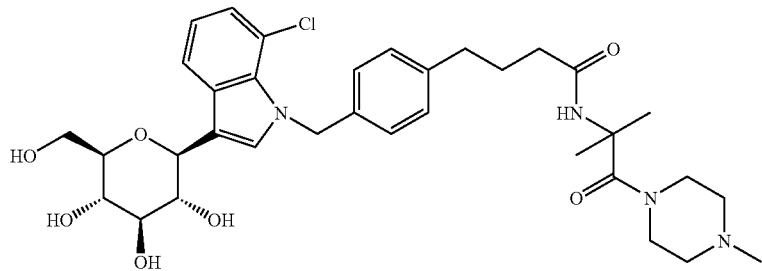
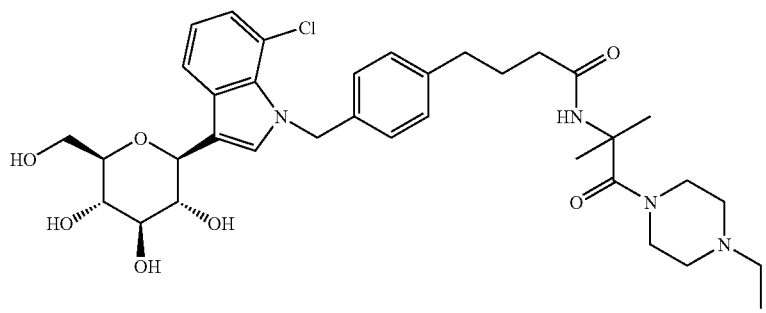
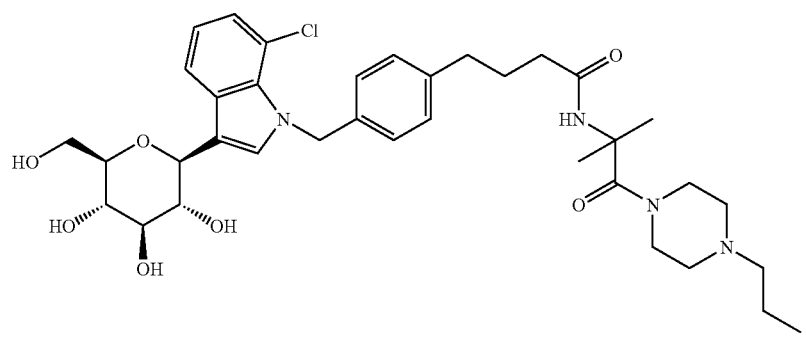
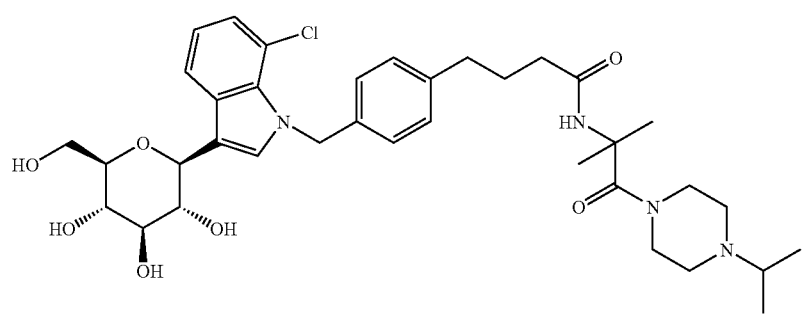
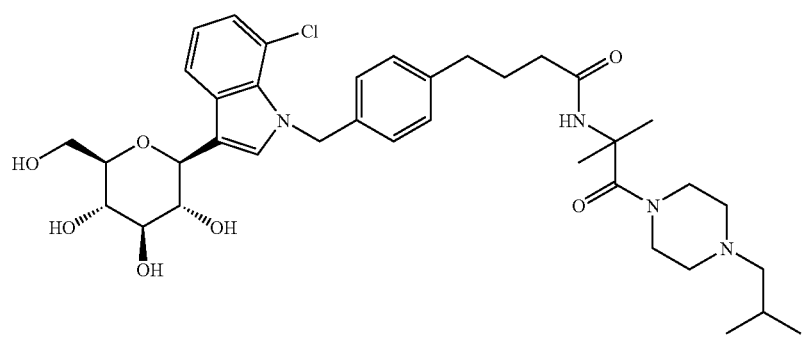

TABLE 11-continued

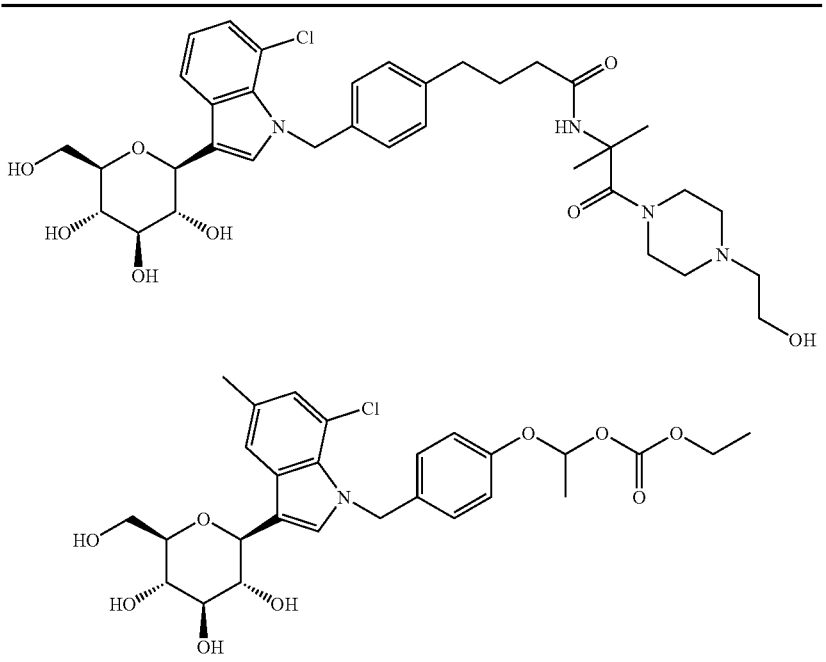

Test Example 1

Assay for Inhibitory Effects on Human SGLT Activity

1) Cloning and Construction of the Vector Expressing Human SGLT1

The cDNA library was prepared for PCR amplification by reverse transcription from total RNA derived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1(−) (Invitrogen). The DNA sequence inserted was perfectly matched to the previously reported sequence.

2) Cloning and Construction of the Vector Expressing Human SGLT2

The cDNA library was prepared for PCR amplification by reverse transcription from total RNA derived from human kidney (Ori gene) using oligo-dT as a primer. Using this cDNA library as a template, the DNA fragment coding 2 to 2039 bp of human SGLT2 (ACCESSION: M95549, M95299), which was reported by R. G. Wells et al., was amplified by PCR method and inserted into the multi-cloning site of pcDNA3.1(−) (Invitrogen). The DNA sequence inserted was perfectly matched to the previously reported sequence.

3) Preparation of the Cells Expressing Human SGLT1 or SGLT2

The vector expressing human SGLT1 or SGLT2 was transfected into COS-7 cells by lipofection method (Lipofectamine 2000: Invitrogen). First, COS-7 cells were plated $5 \times 10^4$ cells/100 µL/well on 96-wells plate and incubated at 37° C. for 2 hours. In addition, per 50 µL medium, 0.3 µg of human SGLT1 or SGLT2 expression vector was mixed with 0.5 µL of Lipofectamine 2000 and the complex solution was prepared. Fifty µL/well of this complex solution was added to COS-7 cells, previously described, and the plate was mixed gently and was used for uptake assay after 2 days culture.

4) Measurement of the Inhibitory Activity Against the Uptake of methyl-α-D-glucopyranoside (1-MG)

A mixture of non-labeled (Sigma) and $^{14}$C-labeled α-MG (Amersham Pharmacia Biotech) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl] ethane sulfonic acid and 5 mM tris(hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal up take measurement buffer, which contains 140 mM choline chloride instead of sodium chloride, was prepared. After removing the culture medium of cells expressing human SGLT1 or human SGLT2, 180 µL of the pre-treatment buffer (the basal uptake buffer without α-MG) was added to each well and incubated at 37° C. for 10 minutes. After repeating the same treatment, the pre-treatment buffer was removed, and then 75 µL per well of the measurement buffer or the basal uptake buffer was added and the cells were incubated at 37° C. After 1 hour incubation, the measurement buffer was removed and the cells were washed twice with 180 µL per well of the washing buffer (the basal uptake buffer containing 10 mM non-labeled α-MG). The cells were solubilized by 75 µL per well of 0.2 mol/L sodium hydroxide, and then the cell lysates were transferred into PicoPlates (Packard). One hundred fifty µL of Microscint-40 (Packard) was added to the wells and mixed. Radioactivity was measured by means of micro-scintillation counter TopCount (Packard). One hundred % was set to the difference between the uptake in the control group and the basal uptake, and the uptake of methyl α-D-glucopyranoside at each drug concentration was calculated. The drug concentration, at which 50% uptake of methyl α-D-glucopyranoside was inhibited ($IC_{50}$ value), was calculated using logit plot. The results are shown in Table 12. Meanwhile, for a pyrrole compound described in patent reference 7 as Example 188 valid $IC_{50}$ value was not obtained. That is to say, the pyrrole compound did not inhibit a human SGLT1 activity at a concentration of $10^{-4}$ M and inhibited only 7% of a human SGLT2 activity at the same concentration.

TABLE 12

| Test compound | hSGLT1 $IC_{50}$(nM) | Test compound | hSGLT2 $IC_{50}$(nM) |
|---|---|---|---|
| Example 6 | 83 | Example 8 | 6 |

As shown in Table 12, 1-substituted-3-(β-D-glyco-pyranosyl)nitrogen-containing heterocyclic compounds (I) of the present invention have an excellent inhibitory activity of a human SGLT1 and/or human SGLT2. On the other hand, a monocyclic pyrrole compound with a substituent having a phenyl group at 1-position and a β-D-glycopyranosyl group at 2-position, that is described in patent reference 7 showed almost no inhibitory activity at the same measuring conditions. Consequently, bicyclic heterocyclic compounds with a substituent having a (hetero) aryl group at 1-position and a β-D-glycopyranosyl group at 3-position are extremely excellent compounds as a human SGLT1 and/or human SGLT2 inhibitor.

Test Example 2

Assay for the Effect on Urinary Glucose Excretion

As experimental animals, overnight fasted SD rats (CHARLES RIVER LABORATORIES JAPAN. Inc., Crj: CD(SD)IGS, male, 7-8 weeks of age, 180-300 g) were used. The test compound was suspended with 0.5% methylcellulose solution and the suspension was used for administration. On the day before drug administration, the rats were transferred in metabolic cages and fasted from the evening. Throughout the study, the rats were given water ad libitum. The test compound was orally administered at the dose of 1 mg/kg and urine collection was performed for 24 hours after the compound administration. The rats were fed ad libitum from 4 hours after the compound administration. The volume of urine collected was measured and a part of urine was used as a sample for glucose concentration measurement. The samples were diluted as appropriate and the glucose concentrations were measured with Glucose CII-Test WAKO (Wako Pure Chemical Industries, Ltd.) and the amount of urinary glucose excretion per 200 g of body weight was calculated.

The results are shown in Table 13.

TABLE 13

| Test Compound | Amount of urinary excretion of glucose in 24 hours (mg/200 g body weight) |
|---|---|
| Example 1 | 182 |
| Example 2 | 27 |
| Example 3 | 15 |
| Example 5 | 76 |
| Example 7 | 122 |

TABLE 13-continued

| Test Compound | Amount of urinary excretion of glucose in 24 hours (mg/200 g body weight) |
|---|---|
| Example 11 | 33 |
| Example 28 | 36 |
| Example 61 | 98 |
| Example 63 | 213 |
| Example 66 | 24 |
| Example 67 | 17 |
| Example 70 | 173 |
| Example 71 | 517 |
| Example 73 | 532 |
| Example 74 | 629 |
| Example 75 | 18 |
| Example 78 | 54 |
| Example 93 | 275 |
| Example 94 | 945 |
| Example 95 | 40 |
| Example 96 | 588 |
| Example 97 | 507 |
| Example 99 | 47 |
| Example 102 | 933 |
| Example 104 | 349 |
| Example 105 | 1693 |
| Example 106 | 1910 |
| Example 108 | 1229 |
| Example 114 | 520 |
| Example 116 | 24 |
| Example 118 | 12 |
| Example 124 | 37 |
| Example 125 | 50 |
| Example 144 | 251 |
| Example 145 | 11 |
| Example 146 | 733 |
| Example 147 | 295 |
| Example 156 | 784 |
| Example 158 | 1708 |

As shown in Table 13, 1-substituted-3-(β-D-glyco-pyranosyl)nitrogen-containing heterocyclic compounds (I) of the present invention have an excellent effect excreting urinary glucose.

INDUSTRIAL APPLICABILITY

The 1-(β-D-glycopyranosyl)-3-substituted nitrogen-containing heterocyclic compound (I) of the present invention or a prodrug thereof, or a pharmaceutically acceptable salt thereof, or a hydrate or a solvate thereof has an SGLT inhibitory activity and can suppress postprandial increase of blood glucose and/or normalize blood glucose by inhibiting absorption of carbohydrates such as glucose at the small intestine and/or by inhibiting reabsorption of glucose at the kidney. Therefore, the present invention can provide agents for the prevention or treatment of diabetes, postprandial hyperglycemia, impaired glucose tolerance, diabetic complications, obesity or the like.

The invention claimed is:
1. A 1-substituted-3-(β-D-glycopyranosyl) nitrogen-containing heterocyclic compound represented by the following general formula (I), or a prodrug thereof wherein a group selected from a group consisting of an acyl group, an alkoxy (acyl) group, an alkoxycarbonyl(acyl) group, an alkoxycarbonyl group, an aryl(alkoxycarbonyl) group, an alkoxy (alkoxycarbonyl) group, an (acyloxy)methyl group, a 1-(acyloxy)ethyl group, an (alkoxycarbonyloxy)methyl group, a 1-(alkoxycarbonyloxy)ethyl group, a [(cycloalkyloxy)carbonyloxy]methyl group and a 1-[(cycloalkyloxy) carbonyloxy]ethyl group is introduced into any one or more hydroxy groups selected from a hydroxy group of a glycopy- ranosyl group and/or any hydroxy group which exists on a (hetero)aryl group of C as a substituent, or a pharmaceutically acceptable salt thereof

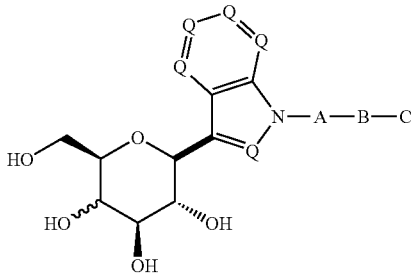

(I)

wherein A represents an alkylene group;

B represents a single bond, —O—, —S— or —NH—;

C represents an aryl group or a heteroaryl group each of which may have a halogen atom, a hydroxy group and a cyano group; an alkyl group, an alkoxyalkyl group, an alkenyl group, an alkynyl group, an alkoxy group, an acyloxy group, an alkylthio group, an alkylsulfinyl group and an alkylsulfonyl group, each of which may have any substituent α described below; a (hetero)aryl group and a (hetero)cycloalkyl group, each of which may have any substituent α and optionally bind to a (hetero)aryl group via an alkylene group, —O—, —NH— or —S—; a —U—V—W—N($R^A$)—Y—Z group, or a —U—V—COO—Y—$R^B$ group, wherein U means a single bond, —O— or —S—, V means a single bond, or an alkylene or alkenylene group, each of which may have a hydroxy group, W means a single bond, —CO—, —$SO_2$— or —C(=NH)—, $R^A$ means a hydrogen atom, or an alkyl group, a (hetero)aryl group or a (hetero)cycloalkyl group, each of which may have any substituent α, Y means a single bond or an alkylene group which may have an oxo group, Z means a hydrogen atom; a formyl group; or an alkyl group, a (hetero)aryl group or a (hetero)cycloalkyl group, each of which may have any substituent α; an acyl group which may have any substituent α; an alkoxy group or an arylalkoxycarbonyl group, each of which may have any substituent α; —CON($R^1$)($R^2$), —CSN($R^1$)($R^2$), —$SO_2$N($R^1$)($R^2$) or —C(=N$R^1$)N($R^2$)($R^3$); one to three amino acid residues, wherein the terminal carboxyl group is an alkoxycarbonyl group optionally having a hydroxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an amino group or a (di)alkylamino group; or a carboxamide group; or an aliphatic, (hetero)cycloalkyl or (hetero)aryl carboxylic acid residue having an alicyclic amine which may have an alkyl group, a (hetero)cycloalkyl group, an alkoxycarbonyl group or an acyl group, each of which may have a hydroxy group an amino group or a (di)alkylamino group, $R^1$, $R^2$ and $R^3$ independently mean a hydrogen atom, a nitro group, a cyano group, a sulfamoyl group, an acyl group, an alkoxycarbonyl group, an aryl group, an alkylsulfonyl group or an alkyl group optionally having any substituent α, $R^A$ and a part of a group forming Z, each of which binds to a nitrogen atom, may bind together to form an alicyclic amine optionally having any substituent α, $R^B$ means a hydrogen atom; an alkoxyalkyl group having a carboxy group or an alkoxycarbonyl group; an alkyl group, a (hetero)aryl group or a (hetero)cycloalkyl group, each of which may have any substituent α; one to three amino acid residues, wherein the terminal carboxyl group may be an alkoxycarbonyl group optionally having a hydroxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an amino group or a (di)alkylamino group; or a carboxamide group; or an aliphatic, (hetero)cycloalkyl or (hetero)aryl carboxylic acid residue having an alicyclic amine which may have an alkyl group, a (hetero)cycloalkyl group, an alkoxycarbonyl group or an acyl group, each of which may have a hydroxy group an amino group or a (di)alkylamino group, the substituent α means a group selected from a group consisting of a halogen atom, a hydroxy group, an acyloxy group, an alkoxycarbonyloxy group, an amino group, a cyano group, a carboxyl group, a carbamoyl group, an alkoxy group, a (di)alkylamino group, an alkoxycarbonyl group, a hydroxyalkoxycarbonyl group, a (hetero)aryl group and a (hetero)cycloalkyl group, in case that any groups have substituents, these substituents may be the same or different, provided that when U is —O— or —S—, V and W are not a single bond at the same time;

Q independently represents a carbon atom which a hydrogen atom or a substituent binds to, or a nitrogen atom.

2. A 1-substituted-3-(β-D-glycopyranosyl) nitrogen-containing heterocyclic compound as claimed in claim 1, wherein the nitrogen-containing heterocyclic compound is an indole compound, or a prodrug thereof, or a pharmaceutically acceptable salt thereof.

3. A 1-substituted-3-(β-D-glycopyranosyl) nitrogen-containing heterocyclic compound as claimed in claim 1, wherein B represents a single bond, or a prodrug thereof, or a pharmaceutically acceptable salt thereof.

4. A 1-substituted-3-(β-D-glycopyranosyl) nitrogen-containing heterocyclic compound as claimed in claim 1, wherein C represents an optionally substituted aryl group, or a prodrug thereof, or a pharmaceutically acceptable salt thereof.

5. An SGLT inhibitor which comprises a 1-substituted-3-(β-D-glycopyranosyl) nitrogen-containing heterocyclic compound as claimed in claim 1, or a prodrug thereof, or a pharmaceutically acceptable salt thereof.

6. A pharmaceutical composition which comprises a 1-substituted-3-(β-D-glycopyranosyl) nitrogen-containing heterocyclic compound as claimed in claim 1, or a prodrug thereof, or a pharmaceutically acceptable salt thereof.

7. A pharmaceutical composition as claimed in claim 6, which is a glucose or galactose absorption inhibitor.

8. A pharmaceutical composition as claimed in claim 6, which is a glucose reabsorption inhibitor.

9. A pharmaceutical composition as claimed in claim 6, which is an agent for the treatment of a disease selected from a group consisting of postprandial hyperglycemia, diabetes, impaired glucose tolerance, diabetic complications, obesity, hyperinsulinemia, hyperlipidemia, hypercholesterolemia, galactosemia, hypertriglyceridemia, lipid metabolism disorder, atherosclerosis, hypertension, metabolic syndrome, congestive heart failure, edema, hyperuricemia and gout.

10. A combination of a pharmaceutical composition as claimed in claim 6 and at least one drug selected from a group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroid-dehydrogenaze inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, an antidiarrhoics, a cathartics, a hydroxymethyl-glutaryl coenzyme A reductase inhibitor, a fibrate, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a squalene epoxidase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

* * * * *